(12) United States Patent
Murdock et al.

(10) Patent No.: US 8,153,170 B2
(45) Date of Patent: *Apr. 10, 2012

(54) JUCARA AND ACAI FRUIT-BASED DIETARY SUPPLEMENTS

(75) Inventors: Kenneth A. Murdock, Springville, UT (US); Alexander G. Schauss, Tacoma, WA (US)

(73) Assignee: K2A LLC, Springville, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/760,395

(22) Filed: Apr. 14, 2010

(65) Prior Publication Data

US 2010/0239694 A1    Sep. 23, 2010

Related U.S. Application Data

(63) Continuation of application No. 12/498,269, filed on Jul. 6, 2009, now Pat. No. 7,799,354, which is a continuation of application No. 10/550,502, filed as application No. PCT/US2004/008739 on Mar. 22, 2004, now Pat. No. 7,563,465.

(60) Provisional application No. 60/456,882, filed on Mar. 21, 2003.

(51) Int. Cl.
*A61K 36/88* (2006.01)
*A61K 36/00* (2006.01)

(52) U.S. Cl. ........................................ 424/727; 424/777

(58) Field of Classification Search .................. None
See application file for complete search history.

(56) References Cited

U.S. PATENT DOCUMENTS

| 3,920,815 A | 11/1975 | Harvey et al. |
|---|---|---|
| 6,231,866 B1 | 5/2001 | Mann |
| 7,182,935 B2 * | 2/2007 | Ribeiro de Nazare et al. ............................ 424/9.71 |
| 7,563,465 B2 * | 7/2009 | Murdock et al. .............. 424/727 |
| 7,700,138 B2 | 4/2010 | Murdock et al. |
| 7,727,564 B2 | 6/2010 | Murdock et al. |
| 7,799,354 B2 | 9/2010 | Murdock et al. |
| 2001/0002407 A1 | 5/2001 | Nair et al. |
| 2001/0020009 A1 | 9/2001 | Nair et al. |
| 2003/0077343 A1 | 4/2003 | Martin et al. |
| 2006/0210609 A1 | 9/2006 | Mower |
| 2006/0210688 A1 | 9/2006 | Mower |
| 2006/0210692 A1 | 9/2006 | Mower |
| 2006/0210697 A1 | 9/2006 | Mower |
| 2006/0216251 A1 | 9/2006 | Morariu |
| 2006/0251750 A1 | 11/2006 | Tabor |
| 2007/0065396 A1 | 3/2007 | Morariu |
| 2007/0071836 A1 | 3/2007 | McCausland et al. |
| 2007/0116838 A1 | 5/2007 | Prakash et al. |
| 2007/0166253 A1 | 7/2007 | Kostick et al. |
| 2007/0166275 A1 | 7/2007 | Gan et al. |
| 2007/0196298 A1 | 8/2007 | Kostick et al. |
| 2007/0292560 A1 | 12/2007 | Quan et al. |
| 2008/0050498 A1 | 2/2008 | Sherwood et al. |
| 2009/0074860 A1 | 3/2009 | Borba |
| 2009/0196921 A1 | 8/2009 | Ebel et al. |

OTHER PUBLICATIONS

Kitagawa et al. J. Food Sci. 1994. vol. 59, No. 4, pp. 844-848.
Bobbio et al. Acta Alimentaria. 2002. vol. 31, No. 4, pp. 371-377.
Chaves et al. Anais Assoc. Quim. Brasil. 1945. vol. 4, No. 3, pp. 169-172.
Harborne, et al. Anthocyanins of Cephaelis. Biochemical Systematics and Ecology. 1994. vol. 22, No. 8, pp. 835-836.
Chaves, et al. Assai, One of the Basic Foods of Amazonia. 1946. vol. 14, No. 159, pp. 23-25.
Chaves, et al. Assai, One of the Basic Foods of Amazonia. 1945. vol. 4, No. 3, pp. 169-172.

* cited by examiner

*Primary Examiner* — Christopher R. Tate
(74) *Attorney, Agent, or Firm* — Steve P. Hassid; Silicon Edge Law Group, LLP

(57) ABSTRACT

The present invention relates to stable, palatable, freeze-dried, fruit-based compositions. Specifically, the inventions relates to compositions of Açai fruit and Jucara fruit with high antioxidant capability and cyclooxygenase-inhibitory activity, and their uses. The invention further provides for methods of making stable, palatable, freeze-dried, fruit-based compositions from Açai fruit and Jucara fruit.

10 Claims, 24 Drawing Sheets

I: CYANIDIN-3-GLUCOSIDE

II: CYANIDIN-3-GLUCOSIDE-COUMARATE

I: CYANIDIN -3- GLUCOSIDE

II: CYANIDIN -3- GLUCOSIDE-COUMARATE

JUCARA AND ACAI FRUIT-BASED DIETARY SUPPLEMENTS

RELATED APPLICATION

This application is a continuation of U.S. application Ser. No. 12/498,269, filed Jul. 6, 2009, which is a continuation of U.S. Pat. No. 7,563,465, granted Jul. 21, 2009, which claims priority to international Patent Application Serial No. PCT/US04/08739, filed Mar. 22, 2004, which claims the benefit of and priority to U.S. Application Ser. No. 60/456,882, filed Mar. 21, 2003, the contents of all of which are incorporated by reference herein in their entireties.

BACKGROUND

1. Field

The present disclosure relates to methods of making stable, palatable, freeze-dried, fruit-based dietary supplements, and uses thereof.

2. General Background

Over the past few decades, free radicals have come to be appreciated increasingly for their importance to human health and disease. Many common and life-threatening diseases, including atherosclerosis, cancer, and aging, have free radical reactions as an underlying mechanism of injury. Over this period of time, our conceptual understanding of the interaction of free radicals with living organisms has evolved and provided unprecedented opportunities for improving the quality and even length of human life.

One of the most common types of free radicals is the reactive oxygen species (ROS). These are the products of normal cell respiration and metabolism and are generally regulated by antioxidants produced in the body. Due to environmental agents such as pollution, and lifestyle factors such as smoking or exercising, the production of free radicals is increased. Such increase may bring the body out of balance, especially as the body ages and the mechanisms that produce antioxidants lose their ability to produce these compounds at their necessary rate, resulting in oxidative stress. The resulting damage can range from disruption of biological processes, killing of cells, and mutation of genetic material, which may lead to the occurrence of cancer.

The potential use of dietary supplements for protection against the effects of oxidative stress and the progression of degenerative diseases and aging has been the subject of an increasing number of studies during the past two decades. In the market today there are many products that contain antioxidants at various levels. These come in the form of foods, liquids and nutritional supplements. The richest sources of these vital nutrients commonly are found in fruits and vegetables having compounds such as Vitamin C, Vitamin E, beta-carotene and others.

The antioxidant hypothesis postulates that supplementation with dietary antioxidants can alleviate the redox imbalance associated with disease. Antioxidants function to bind these free radicals and stabilize and scavenge them out of the system, thereby reducing the amount of damage free radicals may cause.

Synthetic antioxidants such as BHA (butylated hydroxy anisole), BHT (butylated hydroxy toluene) and NDGA (nordihydro-guaiaretic acid) have been developed to date. By way of examples of natural antioxidants, there are antioxidant enzymes such as superoxide dismutase, peroxidase, catalase and glutathione peroxidase, and non-enzymatic antioxidant substances such as tocopherol (vitamin E), ascorbic acid (vitamin C), cartenoid and glutathione.

However, synthetic antioxidants may cause allergic reactions and oncogenesis due to their strong toxicity in the body, and be easily disrupted by heat due to temperature sensitivity. On the other hand, natural antioxidants are safer than synthetic antioxidants in the body but have the problem of weak effect. Therefore, the development of a new natural antioxidant having no problem with safety in use and also having excellent antioxidant activity has been required.

Many studies have demonstrated the protective properties of the polyphenolic flavonoids. Antimutagenic, anticarcinogenic and immune stimulating properties of flavonoids have been reported. The flavonoids are a large group of naturally occurring polyphenols found in fruits, vegetables, grains, bark, tea and wine that have proven in vitro free-radical scavenging potential.

Anthocyanins are naturally occurring compounds that are responsible for the red, purple, and blue colors of many fruits, vegetables, cereal grains, and flowers. For example, the colors of berry fruits, such as blueberries, bilberries, strawberries, raspberries, boysenberries, Marion berries, cranberries, are due to many different anthocyanins. Over 300 structurally distinct anthocyanins have been identified in nature. Because anthocyanins are naturally occurring, they have attracted much interest for use as colorants for foods and beverages. Proanthocyanins are another class of flavonoid compounds that are found in fruits and vegetables and, while being colorless, have antioxidant activities.

Recently, the interest in anthocyanin pigments has intensified because of their possible health benefits as dietary antioxidants. For example, anthocyanin pigments of bilberries (*Vaccinium myrtillus*) have long been used for improving visual acuity and treating circulatory disorders. There is experimental evidence that certain anthocyanins and flavonoids have anti-inflammatory properties. In addition, there are reports that orally administered anthocyanins are beneficial for treating diabetes and ulcers and may have antiviral and antimicrobial activities. The chemical basis for these desirable properties of flavonoids is believed to be related to their antioxidant capacity. Thus, the antioxidant characteristics associated with berries and other fruits and vegetables have been attributed to their anthocyanin content.

In the market today there are many products that contain antioxidants at various levels. These come in the form of foods, liquids and nutritional supplements. The richest sources of these vital nutrients commonly are found in fruits and vegetables having compounds such as Vitamin C, Vitamin E, anthocyanins, beta-carotene, and others. Antioxidants function to bind these free radicals and stabilize and scavenge them out of the system, thereby reducing the amount of damage free radicals may cause.

Since many fruits and vegetables contain these vital nutrients, it is very important to be able to assess the ability of antioxidants in these foods to absorb free radicals. USDA Researchers at Tufts University developed a laboratory test know as ORAC (Oxygen Radical Absorbance Capacity) which rates different foods according to their antioxidant content and its ability to bind these free radicals. Through this test, different foods may be compared and analyzed for their antioxidant ability.

There is a need for the identification of fruits or vegetables with high ORAC scores and the development and production of dietary supplements based thereon.

SUMMARY

The present disclosure relates to the identification of Açai fruit and Jucara fruit with high ORAC scores and cyclooxygenase-inhibitory activity. In one aspect the present disclosure provides for a composition comprising freeze-dried fruit pulp wherein the total anthocyanin concentration is greater than about 1 milligram per gram total weight, the composition has an $ORAC_{FL}$ value greater than about 350 micromole TE per gram total weight and a residual water content less than about 3 percent of the total weight. In one embodiment, the freeze-dried fruit pulp of the composition is freeze-dried Açai fruit pulp. In another embodiment, the freeze-dried fruit pulp of the composition is freeze-dried Jucara fruit pulp. In one embodiment the composition of the disclosure further comprises a pharmaceutically acceptable carrier. In an embodiment, the total anthocyanin concentration of the composition of the disclosure is from about 1 milligram per gram total weight to about 500 milligram per gram total weight. In another embodiment, the total anthocyanin concentration of the composition is from about 1 milligram per gram to about 100 milligram per gram total weight. In yet another embodiment the total anthocyanin concentration of the composition is from about 1 milligram per gram to about 10 milligram per gram total weight. In another embodiment, the composition has an $ORAC_{FL}$ value from about 350 micromole TE per gram total weight to about 10 millimole TE per gram. In another embodiment, the composition has an $ORAC_{FL}$ value from about 350 micromole TE per gram total weight to about 5 millimole TE per gram. In yet another embodiment, the composition has an $ORAC_{FL}$ value from about 350 micromole TE per gram total weight to about 1 millimole TE per gram. In another embodiment, the residual water content of the composition is from about 0.01 percent to about 3 percent of the total weight. In another embodiment, the residual water content of the composition is from about 0.1 percent to about 3 percent of the total weight. In yet another embodiment, the residual water content of the composition is from about 1 percent to about 3 percent of the total weight.

In another aspect, the present disclosure provides for a composition comprising freeze-dried fruit pulp wherein the composition has a cyclooxygenase inhibition value greater than about 15 Aspirin® mg equivalent per gram total weight and a residual water content less than about 3 weight percent of the total weight. In one embodiment, the freeze-dried fruit pulp of the composition is freeze-dried Açai fruit pulp. In another embodiment, the freeze-dried fruit pulp of the is freeze-dried Jucara fruit pulp. In one embodiment the dietary supplement composition of the disclosure further comprises a pharmaceutically acceptable carrier. In another embodiment, the cyclooxygenase inhibition value of the composition is from about 15 Aspirin® mg equivalent per gram total weight to about 10,000 Aspirin® mg equivalent per gram total weight. In another embodiment, the cyclooxygenase inhibition value of the composition is from about 15 Aspirin® mg equivalent per gram total weight to about 1,000 Aspirin® mg equivalent per gram total weight. In yet another embodiment, the cyclooxygenase inhibition value of the composition is from about 15 Aspirin® mg equivalent per gram total weight to about 100 Aspirin® mg equivalent per gram total weight. In another embodiment, the residual water content of the composition is from about 0.01 percent to about 3 percent of the total weight. In another embodiment, the residual water content of the composition is from about 0.1 percent to about 3 percent of the total weight. In yet another embodiment, the residual water content of the composition is from about 1 percent to about 3 percent of the total weight.

In another aspect the disclosure provides for a method of producing a stable and palatable fruit-based composition, comprising harvesting the fruits; weighing the fruits; cleaning the fruits with water; washing the fruits with water at a temperature about 75 degrees C. to 100 degrees C. for a period of time of about 5 seconds to 10 minutes; hulling the fruits to isolate the fruit pulp from the fruit; freezing the fruit pulp to a temperature below about −5 degrees C.; and freeze-drying the fruit pulp under conditions to yield a granular, freeze-dried pulp powder with residual water content of less than 3 weight percent wherein the freeze-dried fruit pulp powder is more stable and palatable than an fruit pulp preparation. In one embodiment, the fruit is Açai fruit. In another embodiment, the fruit is Jucara fruit. In one embodiment, the cleaning step consists of cleaning the fruits with hygienic water at 0.1% (v/v). In another embodiment, citric acid is added to the fruit pulp preparation prior to freezing. In another embodiment, the washing step consists of washing the fruits in water at a temperature of about 80 degrees C. for a period of time of about 10 seconds. In yet another embodiment, the hulling step consists of mechanically hulling the fruits for a time period of between about 2 minutes to 5 about minutes and the hulling step is carried out using about 1 liter of water per 2 kg of fruits. In yet another embodiment, the method of making the dietary supplement composition yields a fruit-based dietary supplement composition that has an $ORAC_{FL}$ value of greater than about 350 micromole TE per gram total weight. In another embodiment, the method of making the composition yields a fruit-based composition that has an $ORAC_{FL}$ value from about 350 micromole TE per gram total weight to about 10 millimole TE per gram. In another embodiment, the method of making the dietary supplement composition yields a fruit-based composition that has an $ORAC_{FL}$ value from about 350 micromole TE per gram total weight to about 5 millimole TE per gram. In yet another embodiment, the method of making the composition yields a fruit-based composition that has an $ORAC_{FL}$ value from about 350 micromole TE per gram total weight to about 1 millimole TE per gram. In another embodiment, the method of making the dietary supplement composition yields a fruit-based composition that has a cyclooxygenase inhibition value greater than about 15 Aspirin® mg equivalent per gram total weight. In a embodiment, the method of making the composition yields a fruit-based dietary supplement composition that has a cyclooxygenase inhibition value from about 15 Aspirin® mg equivalent per gram total weight to about 10,000 Aspirin® mg equivalent per gram total weight. In another embodiment, the method of making the composition yields a fruit-based dietary supplement composition that has a cyclooxygenase inhibition value from about 15 Aspirin® mg equivalent per gram total weight to about 1,000 Aspirin® mg equivalent per gram total weight. In yet another embodiment, the method of making the composition yields a fruit-based composition that has a cyclooxygenase inhibition value from about 15 Aspirin® mg equivalent per gram total weight to about 100 Aspirin® mg equivalent per gram total weight.

In yet another aspect, the disclosure provides a method of preventing or treating a disease or an injury induced by pathological free radical reactions in a mammal, the method comprising administering to the mammal an effective amount of a fruit-based composition of the disclosure, wherein the composition quenches free radicals and reduces the damage induced by pathological free radicals. In one embodiment, the disease or injury is selected from the group consisting of: cancer, colon cancer, breast cancer, inflammatory bowel disease, Crohn's disease, vascular disease, arthritis, ulcer, acute respiratory distress syndrome, ischemia-reperfusion injury, neurodegenerative disorders, autism, Parkinson's Disease, Alzheimer's Disease, gastrointestinal disease, tissue injury induced by inflammation, and tissue injury induced by an environmental toxin.

In yet another aspect, the present disclosure provides a method for alleviating the deleterious effects of pathological free radical reactions in a mammal afflicted with a disease or an injury induced by pathological free radical reactions in a mammal, the method comprising administering to the mammal an effective amount of a fruit-based composition of the disclosure, wherein the composition quenches free radicals and reduces the damage induced by pathological free radicals. In one embodiment, the disease or injury is selected from the group consisting of: cancer, colon cancer, breast cancer, inflammatory bowel disease, Crohn's disease, vascular disease, arthritis, ulcer, acute respiratory distress syndrome, ischemia-reperfusion injury, neurodegenerative disorders, autism, Parkinson's Disease, Alzheimer's Disease, gastrointestinal disease, tissue injury induced by inflammation, and tissue injury induced by an environmental toxin.

In yet another aspect, the present disclosure provides a method of inhibiting cyclooxygenase enzyme activity in a mammal, the method comprising administering to the mammal an effective amount of a composition comprising a fruit-based composition of the disclosure. In one embodiment, the fruit-based dietary supplement composition further comprises a pharmaceutically acceptable carrier. In another embodiment, the a fruit-based composition is administered by a route of administration selected from the group consisting of: oral, intravenous, intraperitoneal, subcutaneous, intramuscular, intraarticular, intraarterial, intracerebral, intracerebellar, intrabronchial, intrathecal, topical, and aerosol route.

In another aspect, the present disclosure provides a method of preventing or treating a disease or an injury associated with increased cyclooxygenase enzyme activity in a mammal, the method comprising administering to the mammal an effective amount of a composition comprising the fruit-based composition of the disclosure. In one embodiment, the fruit-based composition further comprises a pharmaceutically acceptable carrier. In another embodiment, the fruit-based composition is administered by a route of administration selected from the group consisting of: oral, intravenous, intraperitoneal, subcutaneous, intramuscular, intraarticular, intraarterial, intracerebral, intracerebellar, intrabronchial, intrathecal, topical, and aerosol route. In another embodiment, the disease or injury is selected from the group consisting of: cancer, colon cancer, breast cancer, inflammatory bowel disease, Crohn's disease, vascular disease, arthritis, ulcer, acute respiratory distress syndrome, ischemia-reperfusion injury, neurodegenerative disorders, autism, Parkinson's Disease, Alzheimer's Disease, gastrointestinal disease, tissue injury induced by inflammation, and tissue injury induced by an environmental toxin.

These and other objects of the present disclosure will be apparent from the detailed description of the disclosure provided below.

DRAWINGS

The disclosure will be more fully understood by reference to the following drawings which are for illustrative purposes only:

DETAILED DESCRIPTION

Figure 1:
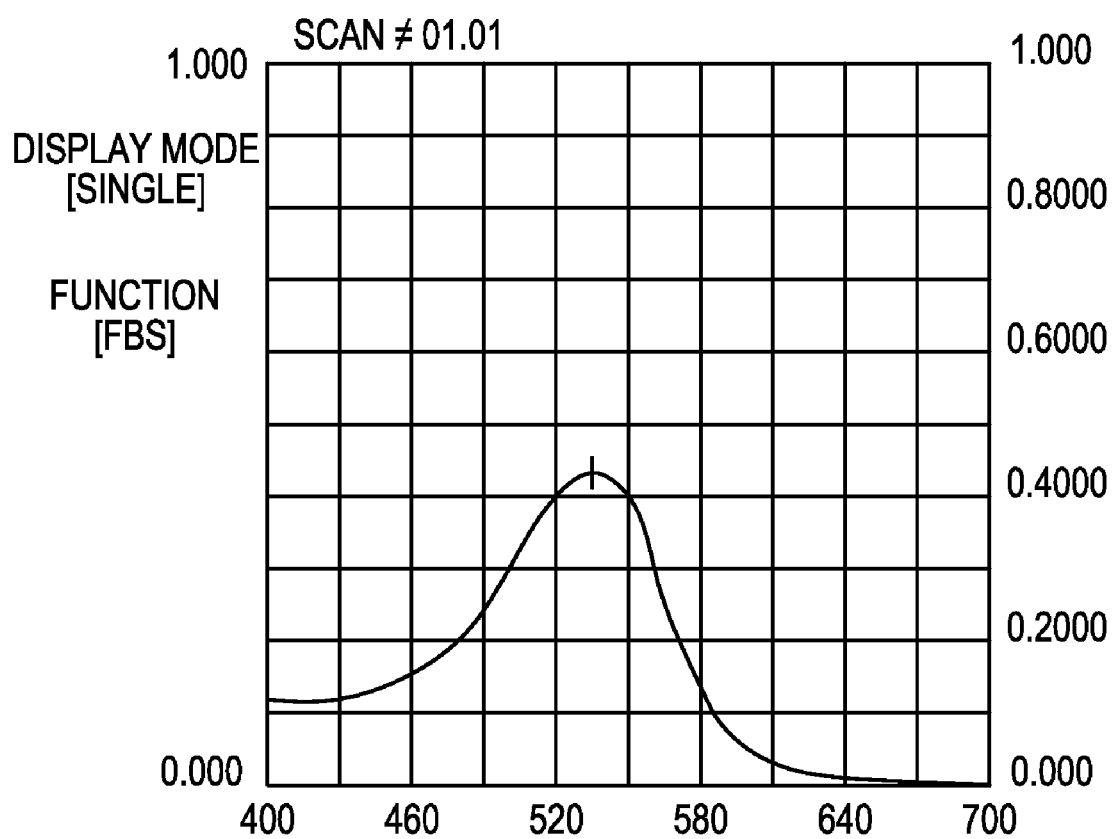
FIG. 1 is a graph showing a representative absorption spectrum of freeze-dried Açai powder.

It is to be appreciated therefore that certain aspects, modes, embodiments, variations and features of the disclosure described below in various levels of detail in order to provide a substantial understanding of the present disclosure. In general, such disclosure provides beneficial dietary supplement compositions, combinations of such compositions with other dietary supplement compositions, and related methods of producing and using same.

Accordingly, the various aspects of the present disclosure relate to therapeutic or prophylactic uses of certain particular dietary supplement compositions in order to prevent or treat a disease or an injury induced by pathological free radical reactions. The various aspects of the present disclosure further relate to therapeutic or prophylactic uses of certain particular dietary supplement compositions in order to prevent or treat a disease or an injury associated with increased cyclooxygenase enzyme activity. Accordingly, various particular embodiments that illustrate these aspects follow.

It is to be appreciated that the various modes of treatment or prevention of medical conditions as described are intended to mean "substantial", which includes total but also less than total treatment or prevention, and wherein some biologically or medically relevant result is achieved.

DEFINITIONS

A "subject," as used herein, is preferably a mammal, such as a human, but can also be an animal, e.g., domestic animals (e.g., dogs, cats and the like), farm animals (e.g., cows, sheep, pigs, horses and the like) and laboratory animals (e.g., rats, mice, guinea pigs and the like).

An "effective amount" of a compound, as used herein, is a quantity sufficient to achieve a desired therapeutic and/or prophylactic effect, for example, an amount which results in the prevention of or a decrease in the symptoms associated with a disease that is being treated. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compounds of the present disclosure, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. The compounds of the present disclosure can also be administered in combination with each other, or with one or more additional therapeutic compounds.

"Açai" is a well-known species of palm tree characteristic of the northern region of Brazil known as Para. The Açai is characterized by a thin trunk and round egg-shaped clustered fruits that are dark purple, sometimes even verging on black when ripe. The Latin name for Açai is *Euterpe oleracea*, Martius; family, Palmaceae. It is also known in English as "Cabbage Palm." In Brazil it is known as: Açai-do-para, Açai-do-baixo Amazonas, palmito Açai, Açaizeiro, Açai, assai, jicara, jucara, palmiteiro, piria; in Colombia it is known as: assai and manaca; and uAçai; and in Surinam it is known as: manaka, pinapalm, prasara, wapoe, and wasei. The term Açai also includes another *Euterpe* sub-species, *E. cating a* Wallace, which also found in Brazil and referred to as "açai". Finally, term Açai also includes another *Euterpe* subspecies, *E. precatoria* Martius, which is found in Bolivia and known to the South American regions and also called "açai" and "jucara".

"Jucara" is another species of palm tree. The Latin name for jucara is: *Euterpe edulis*, Martius; family, Palmaceae. It is also known in Brazil as: assai, Açai, plamito, palmito doce, iucara, palmito jucara, ripeira, icara, jucara, ensarova, palmiteiro. The term Jucara also includes another *Euterpe* subspecies, *E. espiritosantensis* Fernandes, which also found in Brazil, referred to as "jucara". Finally, the term Açai also includes another *Euterpe* subspecies, *E. precatoria Martius*, which is found in Bolivia and known to the South American regions and also called "Açai" and "jucara".

The references cited throughout this application are incorporated herein by reference in their entireties.

Antioxidant Properties and Uses Thereof

The present disclosure identified the fruits of two families of palm trees, Açai and jucara, as having ORAC scores significantly higher than any other fruits or vegetables tested.

The Açai fruits were known to contain a high proportion of mono-unsaturated and polyunsaturated fatty acids, and a relatively low concentration of saturated fat and trans fatty acids. The Açai fruits were also known to be rich in lipids, fibers and protein, and to contain Vitamin E and anthocyanins, two known antioxidants. However, these fruits have been underutilized in the past because the Açai fruits are very prone to rapid deterioration due to oxidation and microbial contamination by bacteria, fungi and yeast. Accordingly, the fruit and juice made from the Açai fruits deteriorate rapidly, and quickly lose their palatability and antioxidant properties—almost half of the anthocyanins degrade within two days after the fruit is picked. In an effort to overcome the rapid deterioration of Açai fruit and juice, and thereby expose the product to broader markets, some companies have tried freezing the fruit pulp. However, simply freezing the Açai fruit pulp in this manner requires careful monitoring of the temperature—with even relatively slight deviations in temperature resulting in the activation of deteriorating enzymes and fermenting agents. Moreover, when thawing such frozen fruit pulp for use, these agents also become activated resulting in grittiness to the pulp.

The foregoing problems, among others, have been resolved by the present disclosure. Specifically, as described in the Examples below, the present disclosure provides a stable and palatable Açai-based dietary supplement composition with significantly higher anthocyanin concentration and higher ORAC scores than any other freeze-dried fruit or vegetable compositions tested.

As a result of the present disclosure, it is now apparent that the Açai fruit provides a very good source for a dietary supplement. Prior to the present disclosure, the fruit was used primarily as an energy drink or as part of a frozen treat with a short shelf life. The Açai-based dietary supplement compositions of the present disclosure provide a stable and palatable product that has a significantly longer shelf life, while significantly increasing the antioxidant properties of the Açai fruit. The present disclosure allows the highly nutritious features of the fruit to not only be preserved, but to be significantly enhanced, and to be enjoyed without the associated concerns of rapid degradation.

While the foregoing discussion focuses primarily on the Açai fruit and dietary supplements derived therefrom, the present disclosure also provide Jucara-based dietary supplement compositions that also contain significantly higher anthocyanin concentration and produced higher ORAC scores than any other freeze-dried fruit or vegetable compositions tested. As will be described below, the Jucara fruit, and dietary supplements derived therefrom, were also found to very high levels of proanthocyanidins and exhibited high antioxidant activities against hydroxy radical and peroxynitrite.

According to the present disclosure, the Açai fruit and the Jucara fruit, juice, dietary supplements, and other compositions derived from the Açai fruit and the Jucara fruit be used to treat, reverse, and/or protect against the deleterious effects of free radicals and oxidative stress.

Free Radicals and Oxidative Stress

Over the past few decades, free radicals, highly reactive and thereby destructive molecules, have come to be appreciated increasingly for their importance to human health and disease. Many common and life-threatening human diseases, including atherosclerosis, cancer, and aging, have free radical reactions as an underlying mechanism of injury.

A free radical is a molecule with one or more unpaired electrons in its outer orbital. Many of these molecular species are oxygen (and sometimes nitrogen) centered. Indeed, the molecular oxygen we breathe is a free radical. These highly unstable molecules tend to react rapidly with adjacent molecules, donating, abstracting, or even sharing their outer orbital electron(s). This reaction not only changes the adjacent, target molecule, sometimes in profound ways, but often passes the unpaired electron along to the target, generating a second free radical or other ROS, which can then go on to react with a new target. In fact, much of the high reactivity of ROS is due to their generation of such molecular chain reactions, effectively amplifying their effects many fold. Antioxidants afford protection because they can scavenge ROS before they cause damage to the various biological molecules, or prevent oxidative damage from spreading, e.g., by interrupting the radical chain reaction of lipid peroxidation.

ROS and Human Health

Because our bodies are continuously exposed to free radicals and other ROS, from both external sources (sunlight, other forms of radiation, pollution) and generated endogenously, ROS-mediated tissue injury is a final common pathway for a number of disease processes.

Radiation Injury

Radiation injury represents an important cause of ROS-mediated disease. Extreme examples include the physical-chemical reactions within the center of the sun and at the center of a thermonuclear blast. With respect to more commonly encountered levels of radiation, depending upon the situation, about two-thirds of the sustained injury is mediated not by the radiation itself, but by the ROS generated secondarily. This applies not only to the acutely toxic forms of radiation injury, but the long-term, mutagenic (and hence carcinogenic) effects as well.

An important clinical application of this principle is encountered regularly in the treatment of cancer by radiation therapy. Large tumors often outgrow their blood supplies and tumor cells die within the center, despite being well oxygenated at the periphery. Between these two regions is an area of tumor that is poorly oxygenated, yet remains viable. Radiation therapy of such tumors is particularly effective at the periphery, where an abundant concentration of oxygen is available to form tumorcidal ROS. The poorly oxygenated center is injured to a significantly smaller degree. While the dead cells in the center don't survive anyway, the poorly oxygenated, yet viable, cells between these two areas can survive a safe dose of radiation therapy, and thereby seed a later local recurrence of the tumor. This is a major reason why many large tumors are treated by a combination of radiation therapy (to kill the tumor at its advancing edges) and surgical removal of the bulk of the tumor, including these particularly dangerous remaining cells.

Cancer and Other Malignancies

Cancer and other malignancies all entail unconstrained cell growth and proliferation based upon changes in the cell's genetic information. In most cases, for example, one or more genes that normally constrain cell growth and replication is/are mutated or otherwise inactivated. These genetic deficiencies correspond directly with deletions and sequence changes in the genetic code, resident in the cell's DNA. A frequently seen final common cause of such DNA damage is free radical injury. Of the myriad injuries sustained by our DNA on a daily basis, most are repaired by normal DNA repair mechanisms within the cell, while some result in cell death. Since such injuries are sporadic and distributed somewhat randomly across the genome, most lethal DNA injuries are clinically inconsequential, resulting in the loss of a few cells among millions. However, when a single cell sustains an injury that impairs growth regulation, it can proliferate disproportionately and grow rapidly to dominate the cell population by positive natural selection. The result is a tumor, frequently a malignant one, where the constraint of growth and proliferation is particularly deficient. Therefore, free radical injury to the genetic material is a major final common pathway for carcinogenesis.

ROS can be generated within the cell not only by external sources of radiation, but also within the body as a byproduct of normal metabolic processes. An important source of endogenous free radicals is the metabolism of some drugs, pollutants, and other chemicals and toxins, collectively termed xenobiotics. While some of these are directly toxic, many others generate massive free radical fluxes via the very metabolic processes that the body uses to detoxify them. One example is the metabolism of the herbicide paraquat. At one time, drug enforcement authorities used this herbicide to kill marijuana plants. Growers realized they could harvest the sprayed crop before it wilted, and still sell the paraquatlaced product. Many who smoked this product subsequently died of a fulminant lung injury. Fortunately, this approach has been abandoned as a particularly inhumane way to solve the drug problem.

While the paraquat story is a particularly striking example of a metabolic mechanism of free radical toxicity, many commonly encountered xenobiotics, including cigarette smoke, air pollutants, and even alcohol are toxic, and often carcinogenic to a large degree by virtue of the free radicals generated by their catabolism within our bodies. Moreover, there is accumulating evidence that a diet rich in fruits and vegetables, which are high in natural antioxidants, and low in saturated fat (a particularly vulnerable target for damage by ROS), reduces the risk of atherosclerosis and cancer.

Atherosclerosis

Atherosclerosis remains the major cause of death and premature disability in developed societies. Moreover, current predictions estimate that by the year 2020 cardiovascular diseases, notably atherosclerosis, will become the leading global cause of total disease burden, defined as the years subtracted from healthy life by disability or premature death. Atherosclerosis is a complex process that leads to heart attack, stroke, and limb loss by the plugging of the arteries with atherosclerotic plaque. This plaque is a form of oxidized fat. When free radicals react with lipids, the consequence is lipid peroxidation, the same process by which butter turns rancid when exposed to the oxygen in the air. While a number of factors influence the development and severity of atherosclerosis, a major factor is the ROS-mediated peroxidation of our low-density lipoproteins (LDLs, or "bad cholesterol". The dietary approach to the prevention of heart disease and stroke is based partially on adding dietary antioxidants to limit LDL oxidation, as well as decreasing the intake of fat itself. These approaches already have made significant inroads into the mortality from heart disease, but the compositions of the present disclosure may offer a safe pharmacological prevention in the future that is not as dependent upon willpower as are diet and exercise.

Neurological and Neurodegenerative Diseases

Neurological and neurodegenerative diseases affect millions of Americans. These include depression, obsessive-compulsive disorder, Alzheimer's, allergies, anorexia, schizophrenia, as well as other neurological conditions resulting from improper modulation of neurotransmitter levels or improper modulation of immune system functions, as well as behavioral disorders such as ADD (Attention Deficit Disorder) and ADHD (Attention Deficit Hyperactivity Disorder). A number of these diseases appear to have ROS toxicity as a central component of their underlying mechanism of nerve cell destruction, including, but not limited to, amyotrophic lateral sclerosis (ALS, or Lou Gehrig's disease), Parkinson's disease, and Alzheimer's disease.

Ischemia/Reperfusion Injury

When an organ is deprived of its blood supply (ischemia) it is injured, not just by the temporary loss of oxygen, but also by the ROS that are generated by reaction with the oxygen that is reintroduced at reperfusion, when the blood supply is restored. In some clinical situations, this injury can prevented by giving antioxidants, sometimes even after the period of ischemia, but just prior to reperfusion. For example, the preservation of kidneys, livers, and other organs in solutions that contain antioxidants, as well as other agents, is now routine prior to their transplantation. Another example is the use of drugs that block the function of free radical generating enzymes prior to stopping the heart for cardiac surgery. These drugs help prevent reperfusion injury when the heart is restarted and flow is restored. This reperfusion injury mechanism also has been found to play an important role in patients suffering from multiple organ failure after trauma, massive surgery, or shock. Multiple organ failure is now the leading cause of death in intensive care units, and extensive efforts are under way to understand better how ROS contribute to this syndrome.

Aging

Aging is a remarkably complex process that has managed to remain relatively opaque to scientific understanding. There is now evidence that aging is a series of processes, i.e., a series of controlled mechanisms, and not just the passive accumulation of wear and tear over the years. If aging is a series of processes, some of these processes are potentially controllable, or at least modifiable. One of the most important of these processes is comprised of an accumulation of the molecular injuries that are mediated by free radicals and other ROS. Recent studies indicate that the therapeutic manipulation of ROS metabolism can actually extend the total life span of mice to a significant degree.

Autistic Disorder

Autism is a disabling neurological disorder that affects thousands of Americans and encompasses a number of sub-types, with various putative causes and few documented ameliorative treatments. The disorders of the autistic spectrum may be present at birth, or may have later onset, for example, at ages two or three. There are no clear-cut biological markers for autism. Diagnosis of the disorder is made by considering the degree to which the child matches the behavioral syndrome, which is characterized by poor communicative abilities, peculiarities in social and cognitive capacities, and maladaptive behavioral patterns.

A number of different treatments for autism have been developed. Many of the treatments, however, address the symptoms of the disease, rather than the causes. For example, therapies ranging from psychoanalysis to psychopharmacology have been employed in the treatment of autism. Although some clinical symptoms may be lessened by these treatments, modest improvement, at best, has been demonstrated in a minor fraction of the cases. Only a small percentage of autistic persons become able to function as self-sufficient adults.

In a preliminary study, an Açai-based dietary supplement was provided to an autistic child with very limited speech and the child was subsequently reported to have significantly enhanced speech.

Properties and Uses Cyclooxygenase Inhibitor

The present disclosure identified the fruits of two families of palm trees, Açai and jucara, as having significant inhibitory properties of both isoforms of cyclooxygenase, COX-1 and COX-2. Cyclooxygenases (sometimes called prostaglandin endoperoxide synthase) are involved in prostaglandin synthesis. COX-1 expression is considered to be constitutive, as basal levels of COX-1 mRNA and protein are observed to be present and generate prostaglandins for normal physiological functions. In contrast, COX-2 expression is inducible.

According to the present disclosure, the Açai fruit and the Jucara fruit, juice, dietary supplements, and other compositions derived from the Açai fruit and the Jucara fruit be used to treat, reverse, and/or prevent diseases or injuries associated with increased cyclooxygenase activity.

Gastroduodenal Mucosal Defense

The gastric epithelium is under a constant assault by a series of endogenous noxious factors including HCl, pepsinogen/pepsin, and bile salts. In addition, a steady flow of exogenous substances such as medications, alcohol, and bacteria encounter the gastric mucosa. A highly intricate biologic system is in place to provide defense from mucosal injury and to repair any injury that may occur.

Prostaglandins play a central role in gastric epithelial defense/repair. The gastric mucosa contains abundant levels of prostaglandins. These metabolites of arachidonic acid regulate the release of mucosal bicarbonate and mucus, inhibit parietal cell secretion, and are important in maintaining mucosal blood flow and epithelial cell restitution. Prostaglandins are derived from esterified arachidonic acid, which is formed from phospholipids (cell membrane) by the action of phospholipase $A_2$. A key enzyme that controls the rate-limiting step in prostaglandin synthesis is cyclooxygenase (COX), which is present in two isoforms (COX-1, COX-2), each having distinct characteristics regarding structure, tissue distribution, and expression. COX-1 is expressed in a host of tissues including the stomach, platelets, kidneys, and endothelial cells. This isoform is expressed in a constitutive manner and plays an important role in maintaining the integrity of renal function, platelet aggregation, and gastrointestinal mucosal integrity. In contrast, the expression of COX-2 is inducible by inflammatory stimuli, and it is expressed in macrophages, leukocytes, fibroblasts, and synovial cells. The beneficial effects of nonsteroidal anti-inflammatory drugs (NSAIDs) on tissue inflammation are due to inhibition of COX-2. COX-2-inhibitors have the potential to provide the beneficial effect of decreasing tissue inflammation while minimizing toxicity in the gastrointestinal tract.

Rheumatoid Arthritis

Rheumatoid arthritis (RA) is a chronic multisystem disease of unknown cause. Although there are a variety of systemic manifestations, the characteristic feature of RA is persistent inflammatory synovitis, usually involving peripheral joints in a symmetric distribution. The potential of the synovial inflammation to cause cartilage destruction and bone erosions and subsequent changes in joint integrity is the hallmark of the disease.

The first line of medical management of RA the use of nonsteroidal anti-inflammatory drugs (NSAIDs) and simple analgesics to control the symptoms and signs of the local inflammatory process. These agents are rapidly effective at mitigating signs and symptoms, but they appear to exert minimal effect on the progression of the disease. NSAIDs block the activity of the Cox enzymes and therefore the production of prostaglandins, prostacyclin, and thromboxanes. As a result, they have analgesic, anti-inflammatory, and antipyretic properties. In addition, the agents may exert other anti-inflammatory effects. Since these agents are all associated with a wide spectrum of toxic side effects, the natural dietary supplement compositions of the present disclosure could provide a non-toxic alternative to NSAIDs.

Cancer

Cyclooxygenases have been studied in various cancers, and COX-1 or COX-2 appear to have a role in several forms of cancer. For example, both COX-1 and COX-2 have been shown to be highly expressed in lung cancer in the mouse. (Bauer et al., 2000, *Carcinogenesis* 21, 543-550). COX-1 was reported to be induced by tobacco carcinogens in human macrophages and is correlated with NFκB activation. (Rioux and Castonguay, 2000, *Carcinogenesis* 21, 1745-1751). COX-1 but not COX-2 was reported to be expressed in human ovarian adenocarcinomas. (Dor et al., 1998, *J. Histochem. Cytochem.* 46, 77-84). According to Ryu et al. (2000, *Gynecologic Oncology* 76, 320-325), COX-2 expression is high in stage 1D cervical cancer. COX-2 was reported to be over expressed in human cervical cancer. (Kulkami et al., 2001, *Clin. Cancer Res.* 7, 429-434). Finally, COX-1 was reported to be upregulated in cervical carcinoma and inhibitors of COX-1 were proposed for the treatment of neoplastic condition of the cervix. Sales et al., US Patent Application 20030220266.

According to the present disclosure, the Açai fruit and the Jucara fruit, juice, dietary supplements, and other compositions derived from the Açai fruit and the Jucara fruit be used to treat, reverse, and/or prevent cancers associated with increased cyclooxygenase activity.

Pharmaceutical Compositions and Formulations

The fruit-based dietary supplements of the present disclosure can be used in beverages, tonics, infusions, or foodstuffs alone, or in combination with other dietary supplements or therapeutics. The fruit-based dietary supplements of the disclosure can be used alone or further formulated with pharmaceutically acceptable compounds, vehicles, or adjuvants with a favorable delivery profile, i.e., suitable for delivery to a subject. Such compositions typically comprise the fruit-based dietary supplement of the disclosure and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include oral, intravenous, intraperitoneal, subcutaneous, intramuscular, intraarticular, intraarterial, intracerebral, intracerebellar, intrabronchial, intrathecal, topical, and aerosol route. The pH can be adjusted with acids or bases, such as hydrochloric acid or sodium hydroxide.

Oral compositions generally include an inert diluent or an edible carrier. They can be enclosed in gelatin capsules, caplets or compressed into tablets. For the purpose of oral therapeutic administration, the fruit-based dietary supplements of the disclosure can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

The fruit-based dietary supplements of the disclosure can also be prepared as pharmaceutical compositions in the form of suppositories (e.g., with conventional suppository bases such as cocoa butter and other glycerides) or retention enemas for rectal delivery.

In one embodiment, the fruit-based dietary supplements of the disclosure are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the fruit-based dietary supplement and the particular therapeutic effect to be achieved, and the limitations inherent in the art of compounding such an active compound for the treatment of individuals. The pharmaceutical compositions can be included in a container, pack, or dispenser together with instructions for administration.

The disclosure is further defined by reference to the following examples, which are not meant to limit the scope of the present disclosure. It will be apparent to those skilled in the art that many modifications, both to the materials and methods, may be practiced without departing from the purpose and interest of the disclosure.

EXAMPLES

Example 1

Composition Analysis of Freeze-Dried Açai

Composition analysis of freeze-dried Açai OPTAçAI; Lot #: 231003/0410-C is detailed below in Table 1 and Table 2.

TABLE 1

| Specifications | | |
|---|---|---|
| Product: Açai powder | Appearance | Powder (Conforms) |
| Common Name: Açai | Color | Dark purple (Conforms) |
| Botanical Name: *Euterpe oleracea* M | | |
| Botanical Family: Palmae | Odor | Characteristic (Conforms) |
| Plant Part Used: Frozen Fruit Pulp | | |
| Harvest Method: Wildcrafted | Flavor | Characteristic (Conforms) |
| Identification Method: HPLC | | |
| | Excipient | None |
| | Drying Method | Vacuum freeze-dried |
| | Mesh size | 100% through 80 mesh |
| | Packaging | Plastic & fiberboard |
| | Shelf life | 2 yrs under proper conditions |
| | Moisture Content | 1% |
| | Re-hydration | 1:13 water |

| Food Analysis | | Impurities | |
|---|---|---|---|
| Calories | 534 | Total heavy metals | <10 ppm |
| Calories from fat | 292 | Lead | 22 ppb |
| Total fat | 32.5 g | Pesticide residue | Wildcrafted |
| Saturated fat | 8.1 g | Solvent residue | None |
| Cholesterol | 13.5 mg | | |
| Sodium | 30.4 mg | | |
| Total carbohydrate | 52.2 g | | |
| Fiber | 44.2 g | | |
| Sugars | 1.3 g | | |
| Protein | 8.1 g | | |
| Moisture | 3.4 g | | |
| Ash | 3.8 g | | |

| Microbiology | |
|---|---|
| Total aerobic bacterial count | <10,000 CFU/g |
| Total fungal count (mold/yeast) | 440 |
| *Escherichia coli* (45° C./g) | Absent |
| *Salmonella* | Absent |
| *Staphylococcus* | Absent |

TABLE 2

| ANALYTE | RESULT/ UNIT | UNIT/ GRAM |
|---|---|---|
| Beta carotene | 34,800 IU | 348 IU |
| Vitamin C (ascorbate ion) | 1,183 mg | 11.83 mg |
| Vitamin E (d-alpha tocopherol) | 648 IU | 6.48 IU |
| Vitamin D | 1,252 IU | 12.52 IU |
| Vitamin Bi (thiamin) | 17.5 mg | 0.175 mg |
| Vitamin B2 (riboflavin) | 22.9 mg | 0.229 mg |
| Vitamin B3 (niacin/niacinamide) | 129.1 mg | 1.291 mg |
| Vitamin B6 (pyridoxine) | 31.9 mg | 0.319 mg |
| Folic acid | 600 mcg | 0.006 mg |
| Vitamin B12 (cyanocobalamin) | 400 mcg | 0.004 mg |
| Biotin | 1.8 mg | 0.006 mg |
| Inositol | 254.2 mg | 2.452 mg |
| Calcium | 55.1 mg | 0.551 mg |

TABLE 2-continued

| ANALYTE | RESULT/ UNIT | UNIT/ GRAM |
|---|---|---|
| Iron | 0.1 mg | 0.001 mg |
| Iodine | 700 mcg | 0.007 mg |
| Magnesium | 730 mg | 7.302 mg |
| Zinc | 0.6 mg | 0.006 mg |
| Selenium | 200 mcg | 0.002 mg |
| Copper | 500 mcg | 0.005 mg |
| Manganese | 19 mg | 0.190 mg |
| Chromium | 6200 mcg | 0.062 mg |
| Molybdenum | 0.00 mg | 0.000 mg |
| Potassium | 3310 mg | 33.10 mg |
| Boron | 5.6 mg | 0.056 mg |

| Heavy Metal | Result |
|---|---|
| Lead (Pb) | 22.0 ppb |

Unless otherwise specified, all methods were performed as described in the Official Methods of Analysis of AOAC International, 17th Edition, 2000 (hereinafter, AOAC). Moisture content of test sample was measured using AOAC method reference #926.08. Protein content of test sample was measured using AOAC method reference #991.20E. Fat content of test sample was measured using AOAC method reference #933.05. Ash content of test sample was measured using AOAC method reference #935.42. Carbohydrate content of test sample was calculated by difference. Caloric content of test sample was calculated using Atwarter Factors. Sugars were measured using AOAC method reference #982.14. Total dietary fiber was measured in test sample using AOAC method reference #991.43. Cholesterol content of test sample was measured using AOAC method reference #994.10. The fatty acid profile of test sample was measured using AOAC method reference #969.33. The sodium, calcium and iron content of test sample was measured using AOAC method reference #984.27. The vitamin C content of test sample was measured using AOAC method reference #967.22. The vitamin A content of test sample was measured by the method of Reynolds and Judds, Analyst, 109:489, 1984. Microbiological testing was conducted essentially as detailed in Example 36 (infra). Trace minerals/metals were analyzed by IPC/MS (Aligent HP-7500a) method by IBC Labs (Integrated Biomolecule Corporation, Tucson, Ariz.).

Example 2

Composition Analysis of Freeze-Dried Açai

Composition analysis of freeze-dried Açai FD berry powder (lot#231003/0410-C) was performed by IBC Labs (Integrated Biomolecule Corporation, Tucson, Ariz.). The results are detailed below in Table 3.

TABLE 3

| ANALYTE | RESULT | UNIT |
|---|---|---|
| Vitamin A (as beta-carotene) | 348 | IU/g |
| Vitamin C (as ascorbate ion) | 11.83 | mg/g |
| Vitamin E (as d-alpha tocopherol) | 6.48 | IU/g |
| Vitamin D (as chotecalciferol) | 12.52 | IU/g |
| Vitamin B-1 (as thiamin) | 0.175 | mg/g |
| Vitamin B-2 (as riboflavin) | 0.229 | mg/g |
| Vitamin B-3 (as niacin/niacinamide) | 1.291 | mg/g |
| Vitamin &-6 (as pyridoxine) | 0.319 | mg/g |
| Vitamin B-12 (as cyanocobalamin) | 0.004 | mg/g |
| Pantothenic acid (as free anion) | 0.561 | mg/g |
| Biotin | 0.018 | mg/g |

TABLE 3-continued

| ANALYTE | RESULT | UNIT |
| --- | --- | --- |
| Folic Add | 0.006 | mg/g |
| Inositol | 2.452 | mg/g |
| Calcium | 0.551 | mg/g |
| Magnesium ion | 7.302 | mg/g |
| Copper ion | 0.005 | mg/g |
| Chromium ion | 0.062 | mg/g |
| Zinc ion | 0.006 | mg/g |
| Iron ion | 0.001 | mg/g |
| Sodium ion | 0.290 | mg/g |
| Manganese ion | 0.190 | mg/g |
| Selenium ion | 0.002 | mg/g |
| Boron ion | 0.056 | mg/g |
| Potassium ion | 33.10 | mg/g |
| Molybdenum ion | 0.000 | mg/g |
| Iodine ion | 0.007 | mg/g |
| Lead ion | 22.0 | ppb |

Unless otherwise specified, all methods were performed as described in the Official Methods of Analysis of AOAC International, 17th Edition, 2000 (hereinafter, AOAC). Moisture content of test sample was measured using AOAC method reference #926.08. Protein content of test sample was measured using AOAC method reference #991.20E. Fat content of test sample was measured using AOAC method reference #933.05. Ash content of test sample was measured using AOAC method reference #935.42. Carbohydrate content of test sample was calculated by difference. Caloric content of test sample was calculated using Atwarter Factors. Sugars were measured using AOAC method reference #982.14. Total dietary fiber was measured in test sample using AOAC method reference #991.43. Cholesterol content of test sample was measured using AOAC method reference #994.10. The fatty acid profile of test sample was measured using AOAC method reference #969.33. The sodium, calcium and iron content of test sample was measured using AOAC method reference #984.27. The vitamin C content of test sample was measured using AOAC method reference #967.22. The vitamin A content of test sample was measured by the method of Reynolds and Judds, Analyst, 109:489, 1984. Trace minerals/metals were analyzed by IPC/MS (Aligent HP-7500a) method by IBC Labs (Integrated Biomolecule Corporation, Tucson, Ariz.).

Example 3

Nutritional Analysis of Freeze-Dried Açai

Nutritional analysis for a 10 g serving of freeze-dried Açai was performed by Silliker, Inc. Illinois Laboratory (Chicago Heights, Ill.; laboratory ID No. 170547501). The results are detailed below in Table 4.

TABLE 4

| | | ANALYTICAL DATA PER 100 G | ANALYTICAL DATA PER SERVING | ROUNDED DATA PER SERVING | % DAILY VALUE |
| --- | --- | --- | --- | --- | --- |
| LABEL ANALYTES | | | | | |
| Calories | | 533.9 | 533.9 | 530 | |
| Calories from Fat | | 292.6 | 292.6 | 290 | |
| Total Fat | (G) | 32.51 | 32.51 | 33 | 51 |
| Saturated Fat | (G) | 8.09 | 8.09 | 8 | 40 |
| Cholesterol | (MG) | 13.5 | 13.5 | 15 | 5 |
| Sodium | (MG) | 30.4 | 30.4 | 30 | 1 |
| Total Carbohydrate | (G) | 52.2 | 52.2 | 52 | 17 |
| Dietary Fiber | (G) | 44.23 | 4.23 | 44 | 176 |
| Sugars | (G) | 1.26 | 1.26 | 1 | |
| Protein (F = 6.25) | (G) | 8.11 | 8.11 | 8 | |
| Vitamin A | (IU) | 1002 | 1002 | | 20 |
| Vitamin C | (MG) | <1.0 | <1.0 | | * |
| Calcium | (MG) | 260 | 260 | | 25 |
| Iron | (MG) | 4.4 | 4.4 | | 25 |
| CONTRIBUTING ANALYTES | | | | | |
| Moisture | (G) | 3.39 | 3.39 | | |
| Ash | (G) | 3.78 | 3.78 | | |
| Beta Carotene | (IU) | <5 | <5 | | |
| Retinol | (IU) | 1002 | 1002 | | |
| Vit. A % Beta Carotene | | * | | | |
| SUGAR PROFILE | | | | | |
| Fructose | | 0.39 | Glucose | | 0.76 |
| Lactose | | <0.10 | Maltose | | 0.11 |
| Sucrose | | <0.10 | | | |

* Contains less than 2% of the Daily Value of this nutrient.
To calculate the values contained in a 25 g serving size, divide all the above values by a factor of 4. A typical beverage serving is 25 g.

Unless otherwise specified, all methods were performed as described in the Official Methods of Analysis of AOAC International, 17th Edition, 2000 (hereinafter, AOAC). Moisture content of test sample was measured using AOAC method reference #926.08. Protein content of test sample was measured using AOAC method reference #991.20E. Fat content of test sample was measured using AOAC method reference #933.05. Ash content of test sample was measured using AOAC method reference #935.42. Carbohydrate content of test sample was calculated by difference. Caloric content of test sample was calculated using Atwarter Factors. Sugars were measured using AOAC method reference #982.14. Total dietary fiber was measured in test sample using AOAC method reference #991.43. Cholesterol content of test sample was measured using AOAC method reference #994.10. The fatty acid profile of test sample was measured using AOAC method reference #969.33. The sodium, calcium and iron content of test sample was measured using AOAC method reference #984.27. The vitamin C content of test sample was measured using AOAC method reference #967.22. The vitamin A content of test sample was measured by the method of Reynolds and Judds, Analyst, 109:489, 1984.

Example 4

Nutritional Analysis of Freeze-Dried Jucara Fruit

Nutritional analysis for a 100 g serving of freeze-dried Jucara fruit was performed by Silliker, Inc. Illinois Laboratory (Chicago Heights, Ill.; laboratory ID No. 171378581). The results are detailed below in Table 5.

TABLE 5

| | | ANALYTICAL DATA PER 100 G | ANALYTICAL DATA PER SERVING | ROUNDED DATA PER SERVING | % DAILY VALUE |
|---|---|---|---|---|---|
| LABEL ANALYTES | | | | | |
| Calories | | 370.2 | 370.2 | 370 | |
| Calories from Fat | | 22.4 | 22.4 | 20 | |
| Total Fat | (g) | 2.48 | 2.48 | 2.5 | 4 |
| Saturated Fat | (g) | 0.68 | 0.68 | 0.5 | 2 |
| Cholesterol | (mg) | <1.0 | <1.0 | 0 | 0 |
| Sodium | (mg) | 25.5 | 25.5 | 25 | 1 |
| Total Carbohydrate | (g) | 86.3 | 86.3 | 86 | 29 |
| Dietary Fiber | (g) | 0.83 | 0.83 | <1 | 4 |
| Sugars | (g) | <0.10 | <0.10 | 0 | |
| Protein (F = 6.25) | (g) | 0.68 | 0.68 | <1 | |
| Vitamin A | (IU) | 179 | 179 | | 4 |
| Vitamin C | (mg) | <1.0 | <1.0 | | * |
| Calcium | (mg) | 33.0 | 33.0 | | 4 |
| Iron | (mg) | 0.53 | 0.53 | | 2 |
| CONTRIBUTING ANALYTES | | | | | |
| Moisture | (g) | 8.62 | 8.62 | | |
| Ash | (g) | 1.93 | 1.93 | | |
| Beta Carotene | IU) | 179 | 179 | | |
| Retinol | (IU) | <5 | <5 | | |
| Vit. A % Beta Carotene | | 100 | | | |
| SUGAR PROFILE | | | | | |
| Dextrose | <0.10 (g/100 g) | | Fructose | <0.10 (g/100 g) | |
| Lactose | <0.10 (g/100 g) | | Maltose | <0.10 (g/100 g) | |
| Sucrose | <0.10 (g/100 g) | | | | |

* Contains less than 2% of the Daily Value of this nutrient.

Unless otherwise specified, all methods were performed as described in the Official Methods of Analysis of AOAC International, 17th Edition, 2000 (hereinafter, AOAC). Moisture content of test sample was measured using AOAC method reference #926.08. Protein content of test sample was measured using AOAC method reference #991.20E. Fat content of test sample was measured using AOAC method reference #933.05. Ash content of test sample was measured using AOAC method reference #935.42. Carbohydrate content of test sample was calculated by difference. Caloric content of test sample was calculated using Atwarter Factors. Sugars were measured using AOAC method reference #982.14. Total dietary fiber was measured in test sample using AOAC method reference #991.43. Cholesterol content of test sample was measured using AOAC method reference #994.10. The fatty acid profile of test sample was measured using AOAC method reference #969.33. The sodium, calcium and iron content of test sample was measured using AOAC method reference #984.27. The vitamin C content of test sample was measured using AOAC method reference #967.22. The vitamin A content of test sample was measured by the method of Reynolds and Judds, Analyst, 109:489, 1984.

Example 5

Quantitative Analysis of Sterols in Freeze-Dried Açai Powder

The sterol composition of freeze-dried Açai powder (#001 Açai Powder; Flora ID No. 210823003) was determined by High Resolution Gas Chromatography (HRGC) (Flora Research Laboratories, Grants Pass, Oreg.) as summarized in Table 6.

TABLE 6

| ANALYTE | PERCENT BY WEIGHT |
|---|---|
| B-Sitosterol | 0.044 = 0.44 mg/g |
| Campesterol | <0.003 = 0.3 mg/g |
| Sigmasterol | 0.004 = 0.04 mg/g |
| Total Sterols | 0.048 |

Example 6

Analysis of the Residual Humidity Analysis of Freeze-Dried Açai

The residual humidity of Açai preparations were determined before and after freeze-drying by the method of Instituto Adolfo Lutz (1976) (UNIVERSIDADE DE SAO PAULO, Faculdade do Clencias Farmaceuticas Departamento de Alimentos e Nutricillo Experimental Laboratorio de Analiste de Alimentos). The percent humidity of raw Açai pulp was 85.37+/−0.14%. The percent residual humidity of freeze-dried Açai pulp was 1.06%. The antocianinas totals (mg/100 g Açai pulp) was 239.32+/−0.74 as determined by the method of Francis and Fuleki, (J. Food Sci, v. 33, p. 72-77, 1968) FIG. 1 shows a representative absorption spectrum observed for Freeze-dried Açai powder.

Example 7

Analysis of Anthocyanins and Phenolic Compounds in Jucara and Açai Preparations

I. General
A. Proanthocyanidins

Proanthocyanidins may help explain the "French Paradox," or why low coronary heart disease rates exist in French provinces known for high-fat foods and red wine consumption. Red wine could be considered an alcohol tincture of several potent flavonoids, including proanthocyanidins from grape seeds. In a provocative study, Fulvio Ursini, M.D., from the University of Padova, Italy, fed volunteers a high-fat meal with and without red wine. He found post-meal plasma peroxide levels were much lower in those who drank wine. (Ursini F, et al. Post-prandial plasma peroxides: a possible link between diet and atherosclerosis. Free Rad Biol Med 1998; 25:250-2.)

A steady stream of animal and in vitro studies supplemented by epidemiological evidence and a smattering of preliminary human studies reveal numerous health benefits associated with these compounds. Chief among the benefits is antioxidant protection against heart disease and cancer.

Proanthocyanidins—more technically oligomeric proanthocyanidins and, hence, the OPC moniker—are a class of flavonoids. Formerly called "condensed tannins," all proanthocyanidins are chemically similar, the only differences being slight changes in shape and attachments of their polyphenol rings. In nature, a jumble of different proanthocyanidins is always found together, ranging from individual units to complex molecules of many linked units (oligomers).

Proanthocyanidins are a highly specialized group of bioflavonoids that have been extensively studied since the late 1960's for their vascular wall strengthening properties and free radical scavenging activity. Proanthocyanidins are one of the most potent free radical scavengers known, possessing an antioxidant effect up to 50 times more potent then vitamin E and up to 20 times greater than vitamin C. Proanthocyanidins also have an affinity for cell membranes, providing nutritional support to reduce capillary permeability and fragility. Although bioflavonoids are widespread in nature, the powerful proanthocyanidin compound is most abundant and available from the bark of the maritime pine and grape seeds, or pips.

Bilberry extract contains anthocyanidins with claimed visual and demonstrated vascular enhancing properties. Bilberry is claimed to reduce visual fatigue and improve light to dark adjustment through its affinity for the rhodopsin-opsin system, the pigment system which mediates both light and dark vision and visual adaptation to dimly lit spaces. However, two military studies done in Israel and the United States have failed to find any such benefit from bilberry extract. The extract may, however promote the retina's own enzymatic antioxidant defenses.

In the vascular system the anthocyanidin extract supports the integrity of vascular walls by increasing vitamin C levels within cells, decreasing the permeabilizing effect of certain proteolytic/lysosomal enzymes, stabilizing cell membranes, and stimulating the synthesis of collagen and connective ground substance tissue.

Grape pips (seeds) are a potent source of proanthocyanidins, or pycnogenols. Jacques Masquelier, Ph.D., who pioneered proanthocyanidin research and coined the term "pycnogenol," used the grape seed extract in his second phase of proanthocyanidin investigations.

In vitro studies suggest OPCs also provide cancer protection. OPCs in *Vaccinium*-family berries, including blueberry, lingonberry and cranberry, block tumor growth by preventing protein synthesis in tumor cells, which prevents them from multiplying. (Bomser J, and Madhavi D. L. In vitro anticancer activity of fruit extracts from *Vaccinium* species. Planta Med, 1996; 62:212-6.) Also in the laboratory, barley bran OPCs transformed human myeloid leukemia cells into cells that were no longer cancerous. (Tamagawa K, and Fukushima S. Proanthocyanidins from barley bran potentiate retinoic acid-induced granulocytic and sodium butyrate-induced monocytic differentiation of HL6O cells. Biosci Biotechnol Biochem, 1998; 62:1483-7.) Another in vitro study found that a patented grape seed extract killed cancer cells; inhibited growth of human breast, lung, stomach and myelogenous leukemia cells by up to 73 percent; and enhanced normal cell growth. (Ye, X. and Krohn. R. L. The cytotoxic effects of a novel 1H636 grape seed proanthocyanidin extract on cultured human cancer cells. Mol Cell Biochem, 1999; 196:99-108.)

Proanthocyanidins may protect the body from a number of potentially toxic agents. Acetaminophen, the active ingredient in Tylenol™, is a potent liver toxin, annually causing 75,000 cases of poisoning requiring hospitalization in the United States. Animal experiments have shown that a week of pretreatment with 100 mg/kg of a patented grape seed extract prevented liver damage from acetaminophen. Organ damage was assessed by studying liver cells for damage and also by monitoring the animal's health. (Ray S D, et al., A novel proanthocyanidin 1H636 grape seed extract increases in vivo bcl-XI expression and prevents acetaminophen-induced programmed and unprogrammed cell death in mouse liver. Arch Biochem Biophys., 1999; 369(1):42-58.)

Proanthocyanidins may do even more than prevent disease; they may help slow the aging process and reduce visible signs of aging. Oxidation damage causes most visible signs of aging in our skin. By preventing this damage, skin will stay younger looking. One way to achieve this is to reduce the damaging effects of ultraviolet (UV) light. Sunscreen products have incorporated a variety of antioxidants with the intent that they will prevent sun injury to the skin. In one study, grape seed OPCs exerted a solo antioxidant effect at a level of potency on a par with vitamin E—protecting different polyunsaturated fatty acids from UV light-induced lipid peroxidation. (Carini M., et al. The protection of polyunsaturated fatty acids in micellar systems against UVB-induced photooxidation by procyanidins from *Vitis vinifera* L., and the protective synergy with vitamin E. Intl J Cosmetic Sci., 1998; 20:203-15.) In this same study, the grape OPCs synergistically interacted with vitamin E, recycling the inactivated form of the vitamin into the active form and thus acting as a virtual vitamin E extender.

Part of the aging process is the degradation of skin by the enzyme elastase, which is released with the inflammatory response. OPCs specifically block elastase, thus maintaining the integrity of elastin. (Meunier M T, and Villie F. The interaction of *Cupressus sempervirens* L. proanthocyanidolic oligomers with elastase and elastins. J Pharm Beig., 1994; 49: 453-61.)

OPCs may even help growth of a thicker head of hair, if the results of animal experiments apply to humans. Japanese researchers shaved mice and found that 40 percent of their hair grew back naturally. When a 1 percent solution of any of three proanthocyanidins was applied to the skin, however, between 70 and 80 percent of the hair grew back. Test tube studies confirm that OPCs actually stimulate the hair keratinocytes to produce three times more hair than the controls. (Takahashi T, et al. Procyanidin oligomers selectively and intensively promote proliferation of mouse hair epithelial cells in vitro and activate hair follicle growth in vivo. J Invest Dermatol., 1999; 112:310-6.)

B. Phenolic Compounds: Luteolin-4'-glucoside

Inhibits proinflammatory cytokine production in macrophages. An anti-cancer flavonoid: poisons eukaryotic DNA topoisomerase I.

II. Measurement of Anthocyanins in Freeze-Dried Jucara Powder

Figure 2:
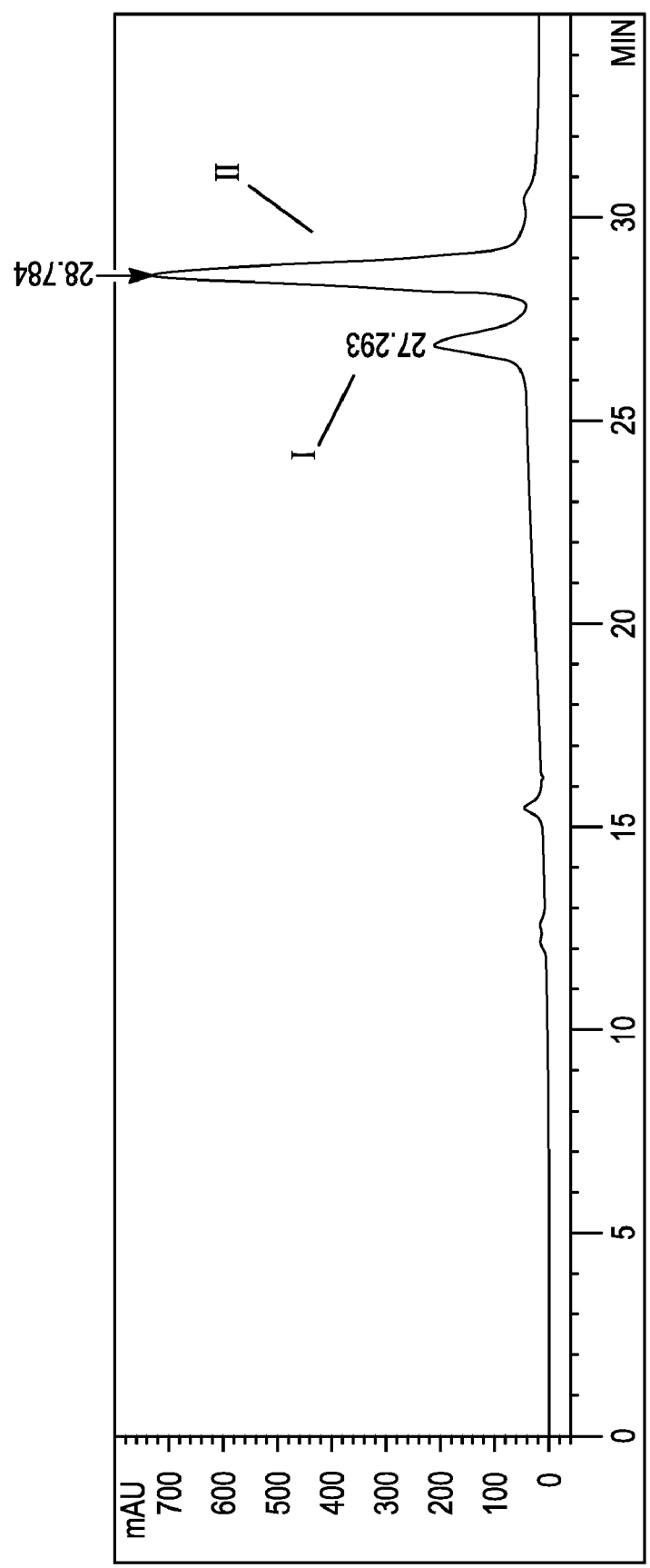
FIG. 2 is a graph showing the anthocyanin profile of freeze-dried Jucara powder as determined by LC/MS/MS chromatographic technique.

The anthocyanin profile of freeze-dried Jucara powder was measured by LC/MS/MS and is shown in FIG. 2. The LC/MS/MS results for peaks shown in FIG. 2 are summarized below in Table 7.

Anthocyanin and OPC analysis (phenolic compounds) was performed as detailed below. Briefly, powdered sample was simultaneously differentially extracted into water and ethyl acetate. Each layer was collected and filtered void of solids. Intact anthocyanins were analyzed from the water layer by HPLC on a column of C-18 Zorbax 5 µm 150×4.6 mm using a gradient mobile phase (1 ml/min. flow) consisting of A (0.5% phosphoric acid) B (water:acetonitrile:acetic acid: phosphoric acid—50:48.5:1:0.5) and the following program—initial 100% A, 20 min 80% A, 30 min 40% A, 36 min 80% A. Identification/quantification performed by external standards. Oligomeric proanthocyanins were analyzed from the ethyl acetate layer following evaporational drying, and reconstitution in anhydrous methanol. Chromatography performed on a Phenyl-hexyl Luna 3 µm 250×3.5 mm using a gradient mobile phase (1 ml/min flow) consisting of A (water: acetonitrile:acetic acid—89:9:2) B (water acetonitrile—20: 80) and the following program—initial 100% A, 25 min 60% A, 32 min 100% B, 40 min 100% A. Identification/quantification performed by first principles based on extinction coefficients of parent epicatachin and catachin ring structures.

TABLE 7

| Peak | Retention Time | Molecular Ion | Product Ion |
|------|----------------|---------------|-------------|
| I    | 27.29          | 449           | 287         |
| II   | 28.78          | 595           | 449, 287    |

Figure 3:
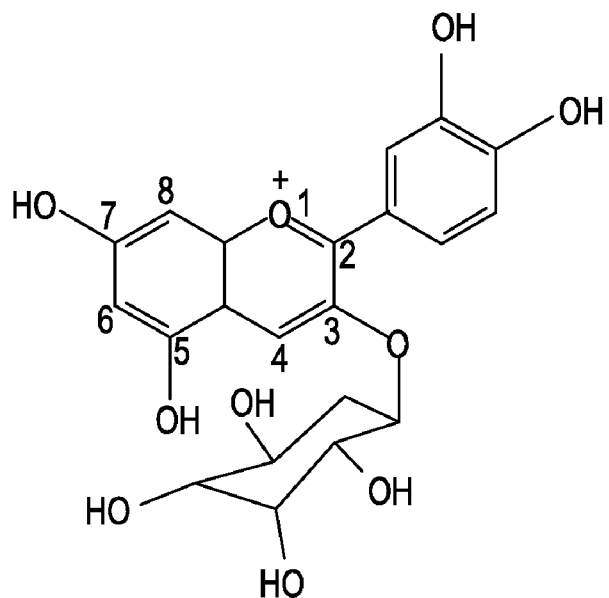
FIG. 3 is a schematic diagram showing the chemical structures of anthocyanins in freeze-dried Jucara powder.
Figure 3:
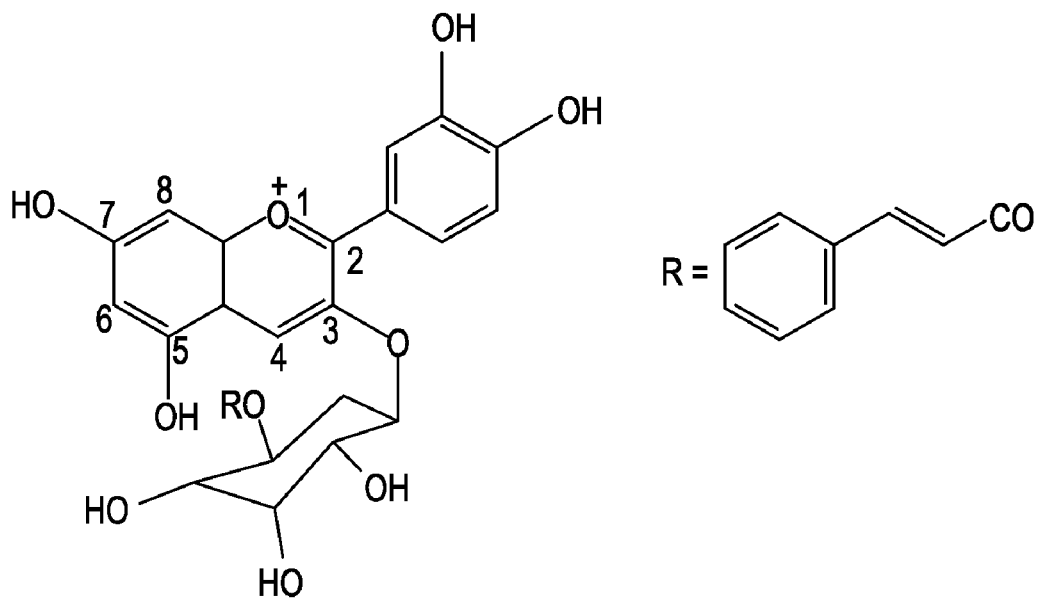

The structures of anthocyanins from freeze-dried Jucara powder are shown in FIG. 3.

III. Measurement of Anthocyanins in Freeze-Dried Açai Powder

Figure 4:
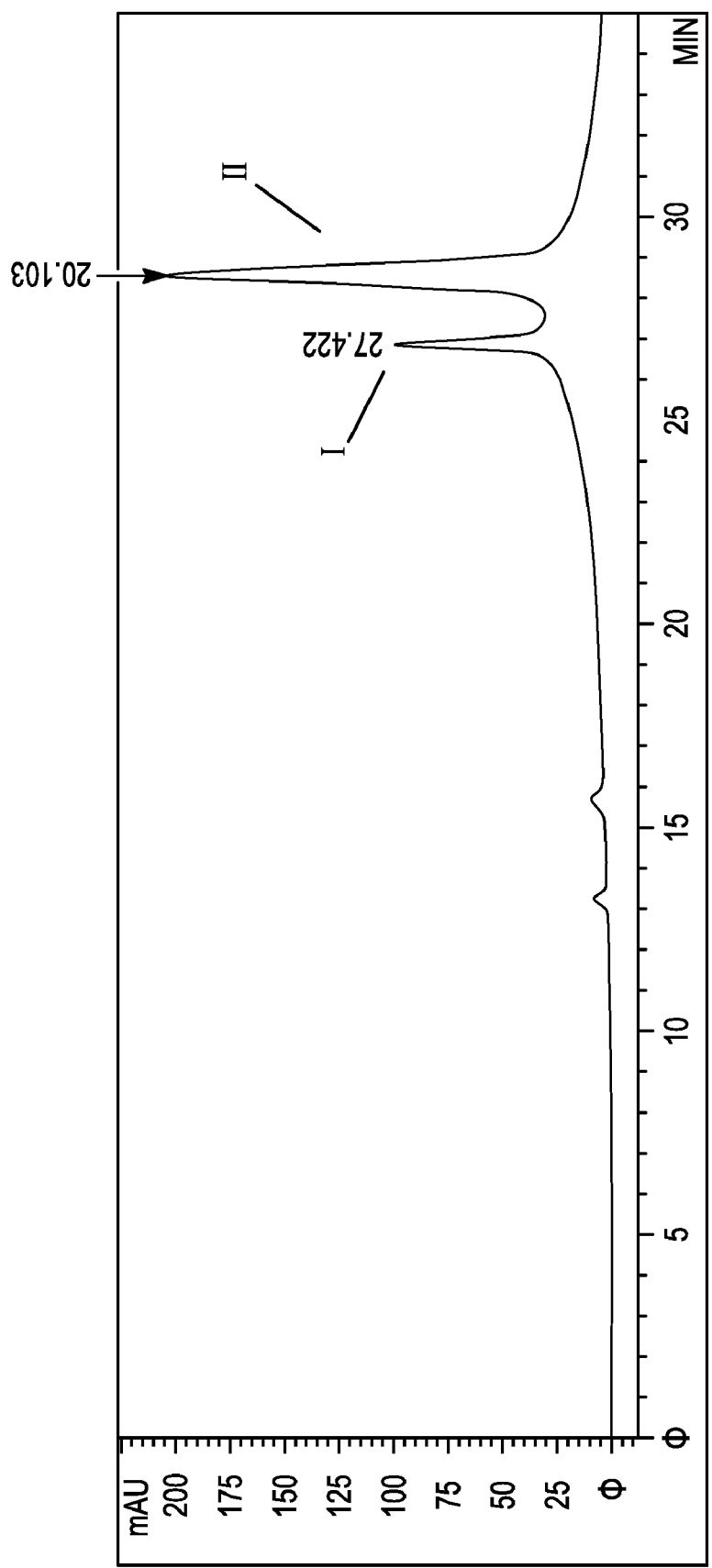
FIG. 4 is a graph showing the anthocyanin profile of freeze-dried Açai powder as determined by LC/MS/MS chromatographic technique.

The anthocyanin profile of freeze-dried Açai powder was measured by LC/MS/MS and is shown in FIG. 4. The LC/MS/MS results for peaks shown in FIG. 4 are summarized below in Table 8.

TABLE 8

| Peak | Retention Time | Molecular Ion | Product Ion |
|------|----------------|---------------|-------------|
| I    | 27.42          | 449           | 287         |
| II   | 29.19          | 595           | 449, 287    |

Analysis performed as detailed above.

Figure 5:
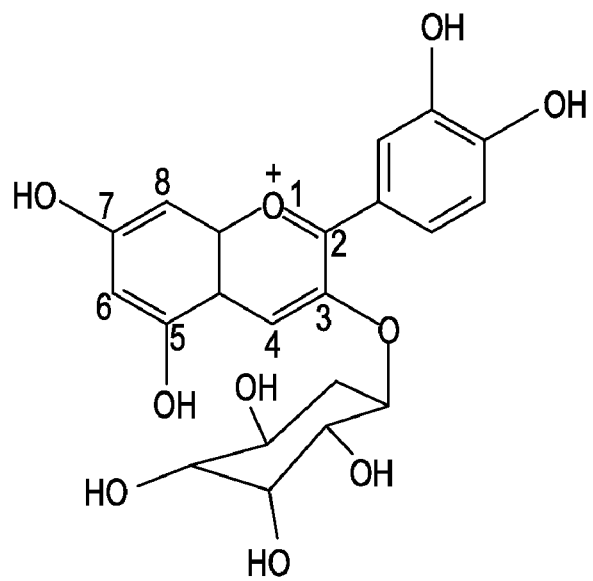
FIG. 5 is a schematic diagram showing the chemical structures of anthocyanins in freeze-dried Açai powder.
Figure 5:
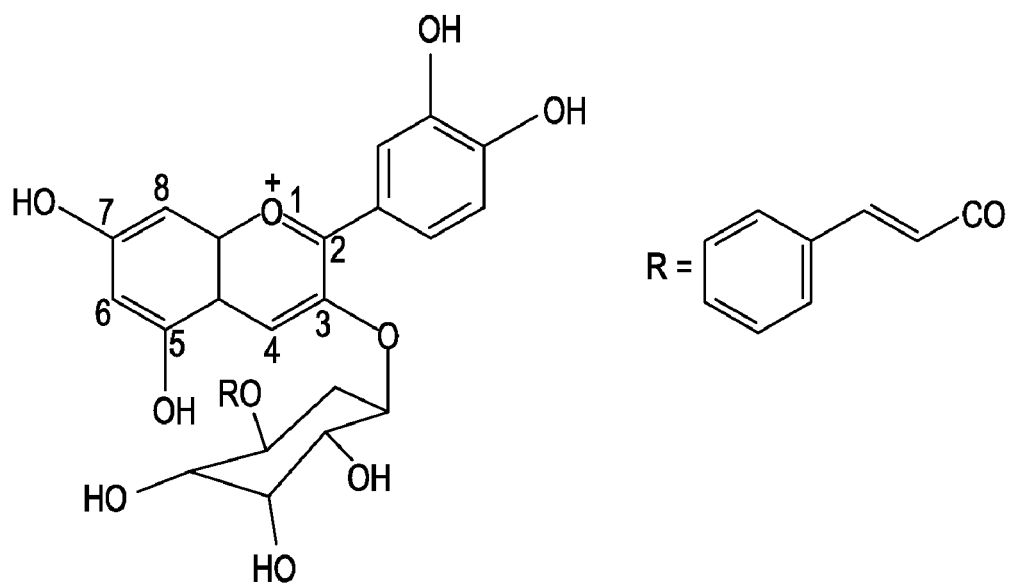
Figure 6:
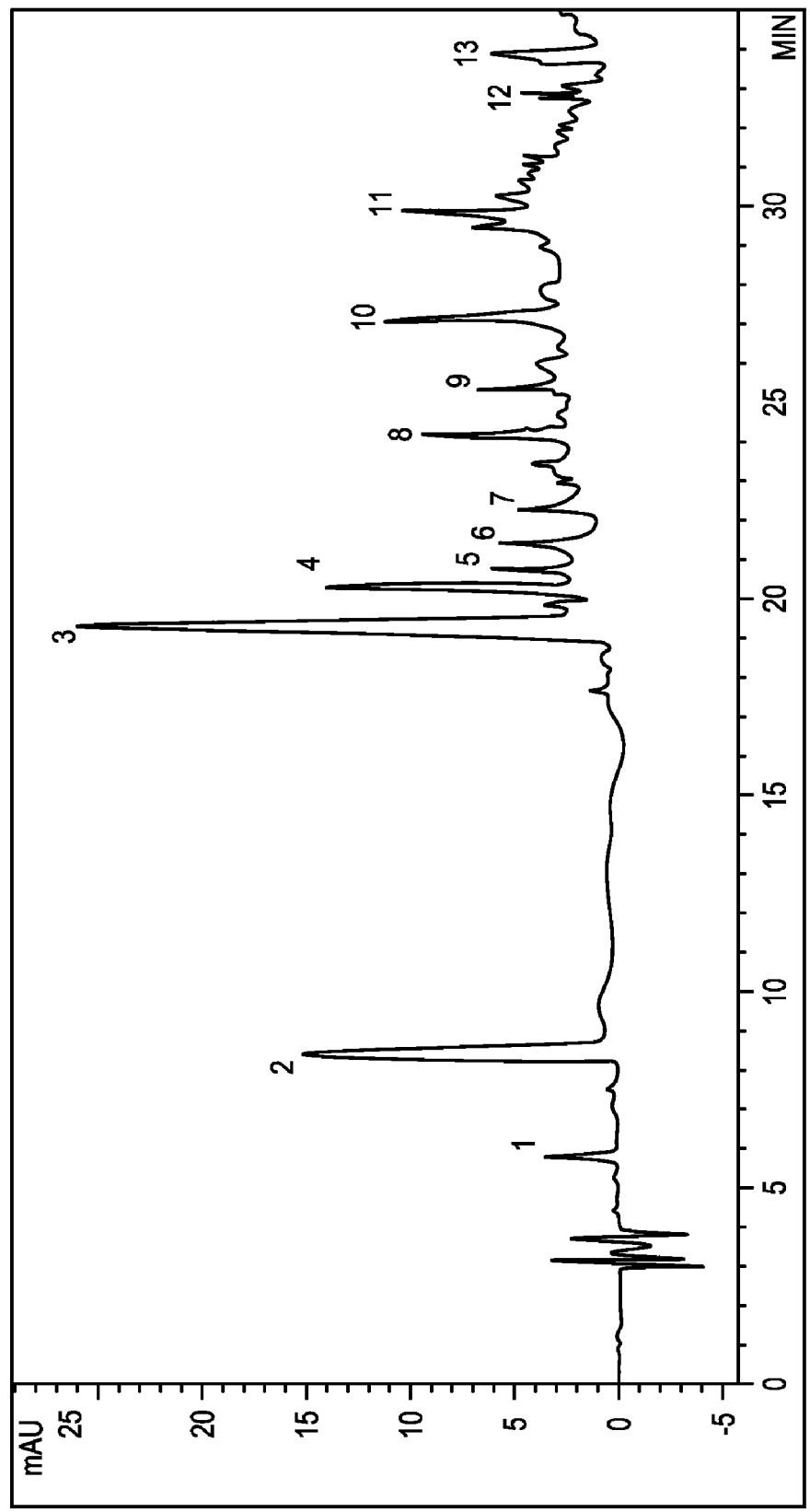
FIG. 6 is a graph showing the phenolic compound profile of freeze-dried Jucara powder as determined by HPLC and mass spectroscopy chromatographic technique.

The structures of anthocyanins from freeze-dried Açai powder are shown in FIG. 5.

IV. Content of Anthocyanins for Freeze-Dried Jucara Powder and Freeze-Dried Açai Powder The contents of anthocyanins measured in freeze-dried Jucara and freeze-dried Açai powder is summarized below in Table 9.

TABLE 9

| Contents of Anthocyanins | | |
|---|---|---|
| Anthocyanin (mg/g) | Jucara | Açai |
| Cyanidin-3-glucoside | 3.43 | 1.77 |
| Cyanidin-3-glucoside-coumarate | 17.56 | 3.93 |
| Total: | 20.99 | 5.7 |

Figure 7:
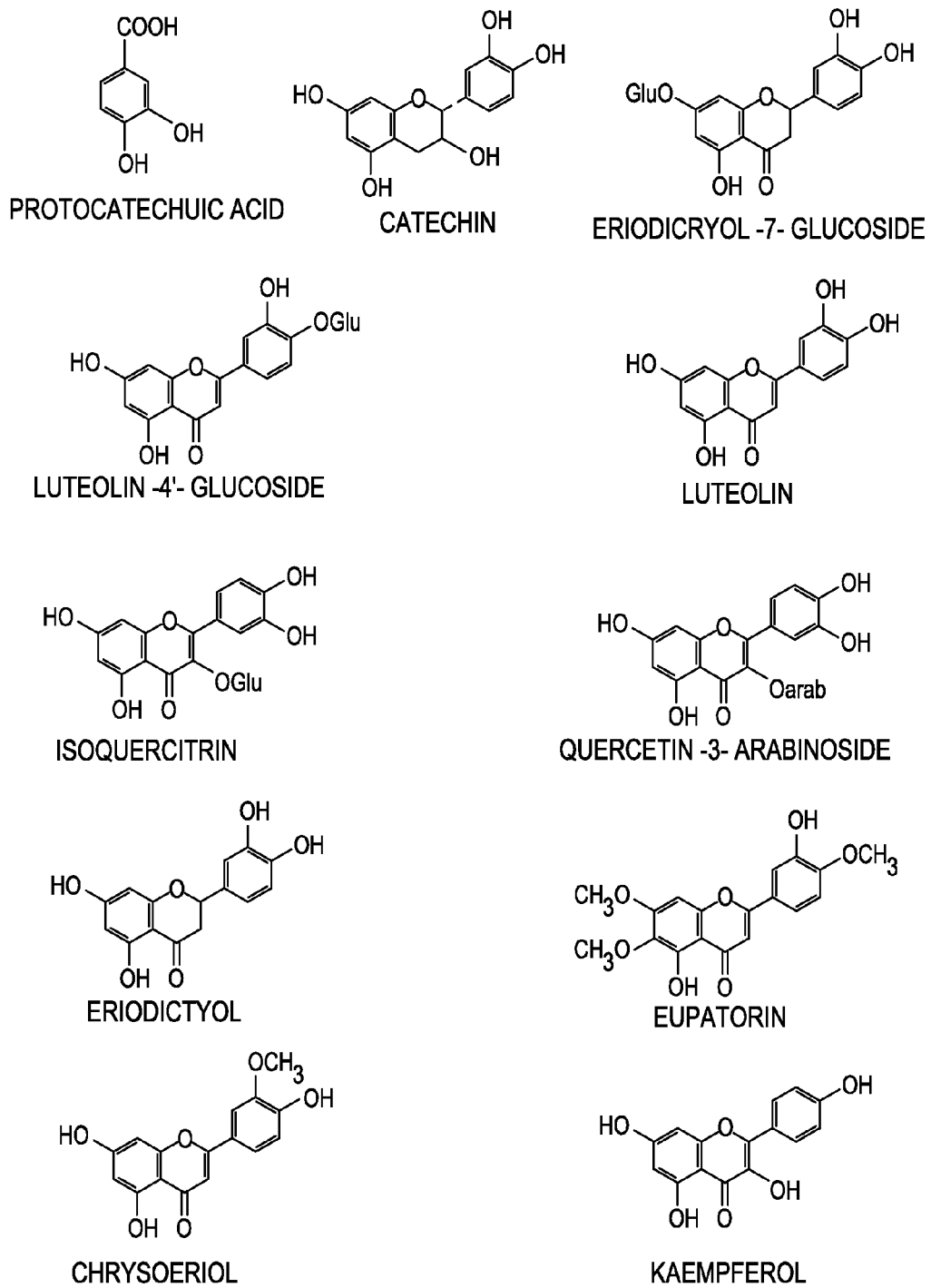
FIG. 7 is a schematic diagram showing the chemical structures of phenolic compounds in freeze-dried Jucara powder.

The structures of the individual phenolic compounds present in freeze-dried Jucara powder are shown in FIG. 7. Significant amounts of phenolic compounds in freeze-dried Açai powder were not detected. Analysis was performed as detailed above.

Figure 8:
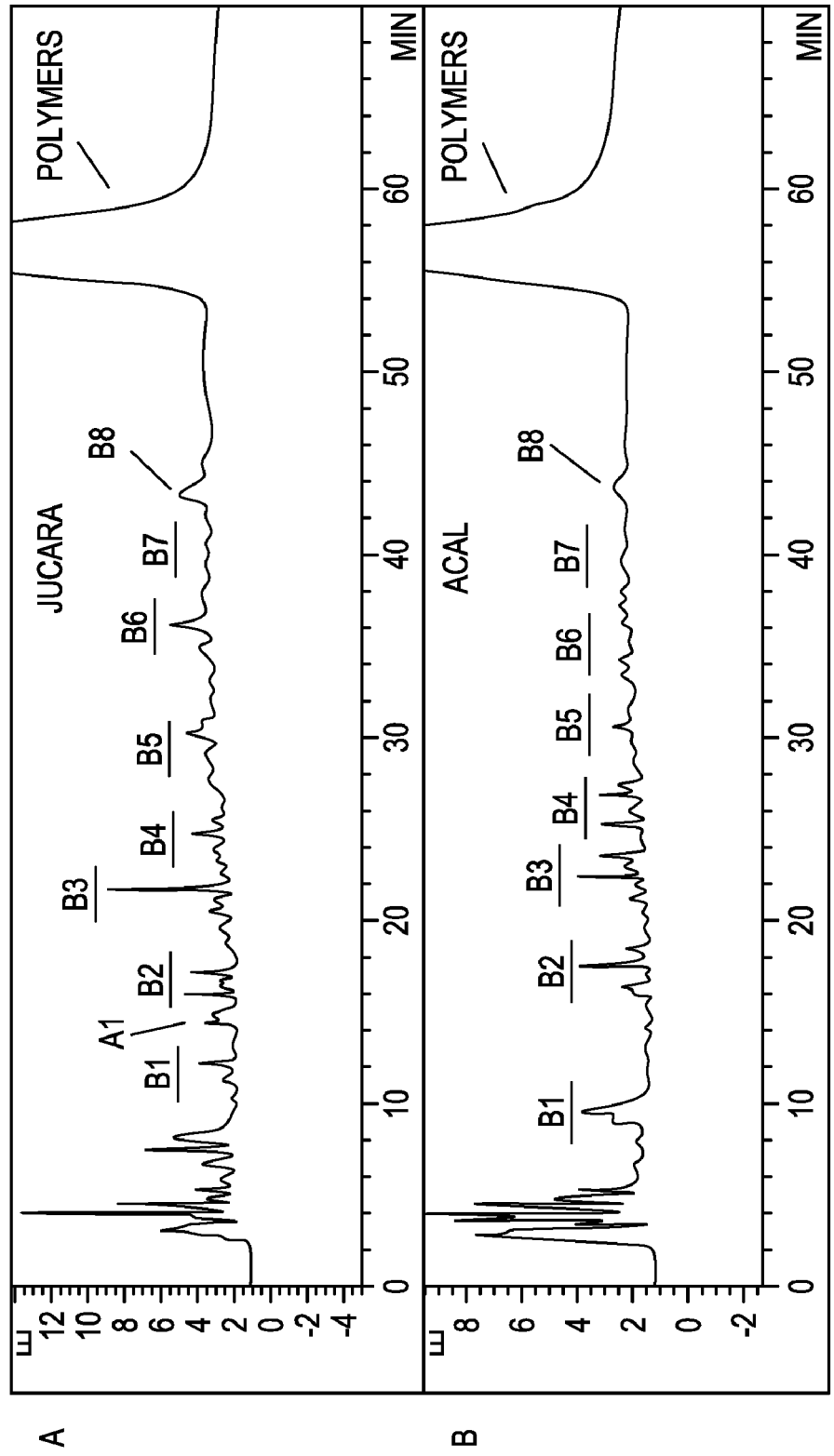
FIG. 8 is a graph showing the proanthocyanin profiles of freeze-dried Açai powder and freeze-dried Jucara powder as determined by chromatographic technique.

VI. Measurement of Proanthocyanidins in Freeze-Dried Açai Powder and Freeze-Dried Jucara Powder The proanthocyanidin profile of freeze-dried Açai powder and freeze-dried Jucara powder was chromatographically determined and is shown in FIG. 8. As detailed in FIG. 8, the profile of proanthocyanins. B1 are epicatechin and catechin. Peaks B2 through B8 stand for the B type procyanidin from dimers to octamers. A2 are dimers with one A type interflavan linkage as reflected by the mass spectra. The results for peaks shown in FIG. 8 are summarized below in Table 11.

TABLE 11

| Content of proanthocyanidins in freeze-dried samples | | |
|---|---|---|
| Proanthocyanidins (mg/g, mean ± SD, n = 3) | Jucara | Açai |
| Monomers | 0.35 | 0.21 |
| Dimers | 0.52 | 0.30 |
| Trimers | 0.29 | 0.25 |
| Tetramers | 0.87 | 0.32 |
| Pentamers | 0.50 | 0.31 |
| Hexamers | 1.03 | 0.52 |
| Heptamers | 0.60 | 0.32 |
| Octamers | 0.72 | 0.39 |
| Nonamers | 1.40 | 0.64 |
| Decamers | 0.55 | 0.34 |
| Polymers | 18.53 | 9.28 |
| Total: | 25.38 | 12.89 |

Figure 9:
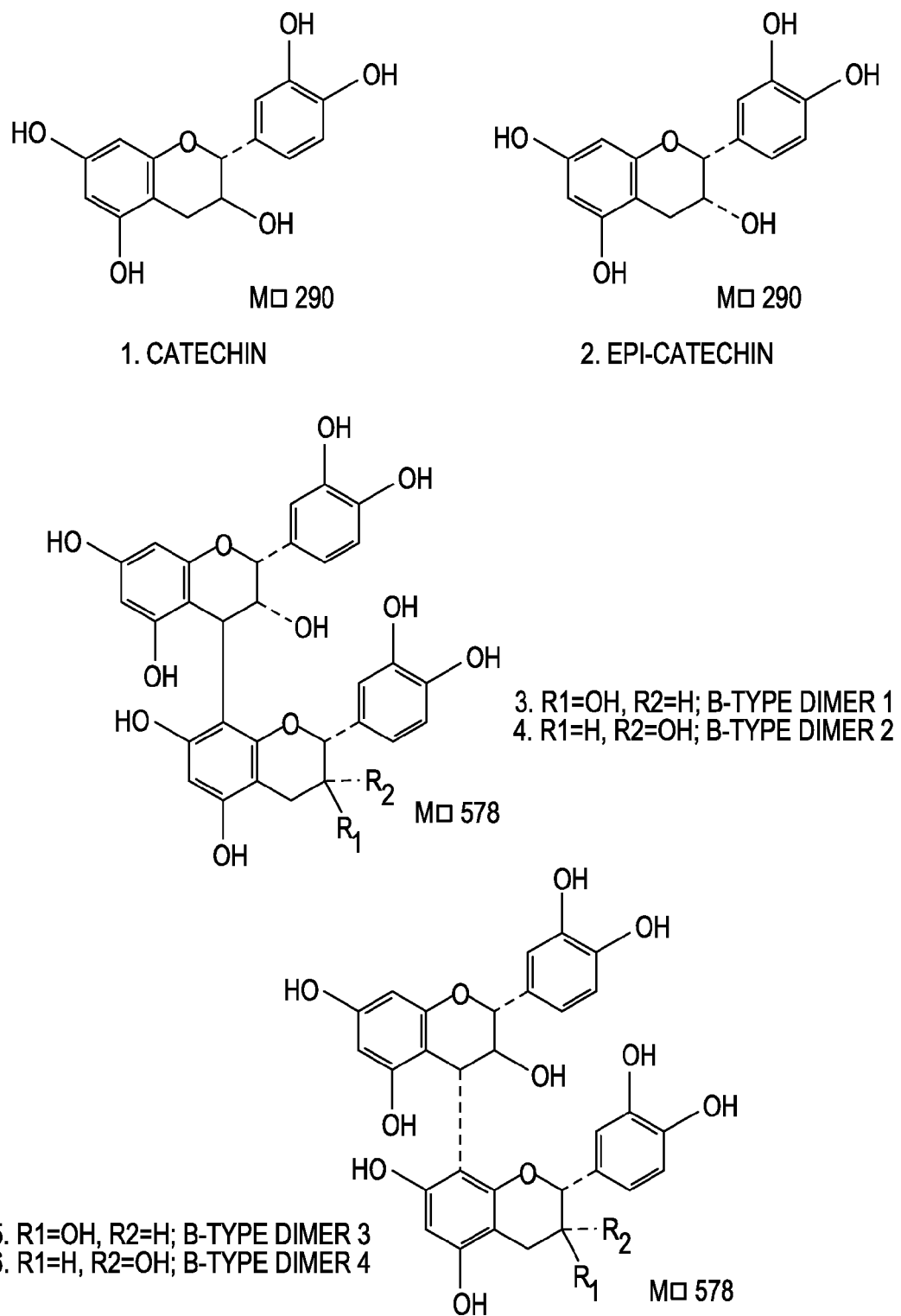
FIG. 9 is a schematic diagram showing the chemical structures of proanthocyanin compound in freeze-dried Açai powder and freeze-dried Jucara powder.

Jucara contains very high level of proanthocyanidins, as well as, high antioxidant activities against hydroxyl radical and peroxynitrite. FIG. 9 shows representative structures of proanthocyanidins detected in freeze-dried Açai powder and freeze-dried Jucara powder. Analysis was performed as detailed above.

Example 8

Composition Analysis of Anthocyanin Content of Freeze-Dried Açai Berry Powder

Composition analysis of the anthocyanin content of freeze-dried Açai FD berry powder (lot# MAL001) was performed by IBC Labs (Integrated Biomolecule Corporation, Tucson, Ariz.). The results are detailed below in Table 12.

TABLE 12

| Analyte | Result | Unit |
|---|---|---|
| Anthocyanins | | |
| Cyanidin-3-glucoside | 1.566 | mg/g |
| Cyanadin-3-glucoside-6' coumarate | 4.121 | mg/g |
| Total authocyanins: | 5.687 | mg/g |
| OPC Degree of oligomerization (includes linear/branched) | | |
| One | 0.5944 | mg/g |
| Two | 0.4082 | mg/g |
| Three | 0.7988 | mg/g |
| Four | 0.8124 | mg/g |
| Five | 0.6821 | mg/g |
| Six | 0.5223 | mg/g |
| Seven | 0.4046 | mg/g |
| Eight | 0.3121 | mg/g |
| Nine and above | 7.2067 | mg/g |
| Total oligomeric proanthocyanins: | 11.7416 | mg/g |

Anthocyanin and OPC analysis was performed according to methodology employed by Brunswick Laboratories. Briefly, powdered sample was simultaneously differentially extracted into water and ethyl acetate. Each layer was collected and filtered void of solids. Intact anthocyanins were analyzed from the water layer by HPLC on a column of C-18 Zorbax 5 μm 150×4.6 mm using a gradient mobile phase (1 ml min. flow) consisting of A (0.5% phosphoric acid) B (water acetonitrile:acetic acid:phosphoric acid—50:48.5:1:0.5) and the following program-initial 100% A, 20 min 80% A, 30 min 40% A, 36 min 80% A. Identification/quantification performed by external standards. Oligomeric proanthocyanins were analyzed from the ethyl acetate layer following evaporational drying, and reconstitution in anhydrous methanol. Chromatography performed on a Phenyl-hexyl Luna 3 μm 250×3.5 mm using a gradient mobile phase (1 ml/min flow) consisting of A (water:acetonitrile:acetic acid—89:9:2) B (water:acetonitrile—20:80) and the following program—initial 100% A, 25 min 60% A, 32 min 100% B, 40 min 100% A. Identification/quantification performed by first principles based on extinction coefficients of parent epicatachin and catachin ring structures.

Example 9

Fatty Acid Analysis of Freeze-Dried Açai

Fatty acid analysis for freeze-dried Açai pulp was performed by Silliker, Inc. Illinois Laboratory (Chicago Heights, Ill.; laboratory ID No. 170547512). The results are detailed below in Table 13, Table 14 and Table 15.

TABLE 13

| SATURATED FATTY ACID | FORMULA | % |
|---|---|---|
| Butyric | 4:0 | <0.1 |
| Captoic | 6:0 | <0.1 |
| Caprylic | 8:0 | <0.1 |
| Capric | 10.0 | <0.1 |
| Undecanoic | 11:0 | <0.1 |
| Lauric | 12:0 | 0.1 |
| Tridecanoic | 13:0 | <0.1 |
| Myristic | 14:0 | 0.2 |
| Pentadecanoic | 15:0 | <0.1 |
| Palmitic | 16.0 | 24.1 |
| Marganic | 17:0 | 0.1 |
| Stearic | 18:0 | 1.6 |
| Nonadecanoic | 19:0 | <0.1 |
| Eicosanoic | 20:0 | <0.1 |
| Behenic | 22:0 | <0.1 |
| Tricosanoic | 23.0 | <0.1 |
| Lignoceric | 24:0 | <0.1 |

TABLE 14

| MONOUNSATURATED FATTY ACID | FORMULA | % | POLYUNSATURATED FATTY ACID | FORMULA | % |
|---|---|---|---|---|---|
| Tridecenoic | 13:1 | <0.1 | Linoleic | 18:2 | 12.5 |
| Myristoleic | 14:1 | <0.1 | Linolenic | 18:3 | 0.8 |
| Pentadecenoic | 15:1 | <0.1 | Gamma Linolenic | 18:3G | <0.1 |
| Palmitoleic | 16:1 | 4.3 | Eicosadienoic | 20:2 | <0.1 |
| Margarolleic | 17:1 | 0.1 | Eicosatrienoic | 20:3 | <0.1 |
| Oleic | 18:1C | 56.2 | Homogamma Linolenic | 20:3G | <0.1 |
| Elaidic | 18:1T | <0.1 | Arachidonic | 20:4 | <0.1 |
| Gadoleic | 20:1 | <0.1 | Eicosapentaenoic | 20:5 | <0.1 |
| Erucic | 22:1 | <0.1 | Docosadienoic | 22:2 | <0.1 |
| Nervonic | 24:1 | <0.1 | Docosahexaenoic | 22:6 | <0.1 |

TABLE 15

| Total Monounsaturated Fatty Acid | 60.60 | 61% monounsaturated |
|---|---|---|
| Total Saturated Fatty Acid | 26.10 | 26% saturated |
| Total Polyunsaturated Fatty Acid | 13.30 | 13% polyunsaturated |

Unless otherwise specified, all methods were performed as described in the Official Methods of Analysis of AOAC International, 17th Edition, 2000 (hereinafter, AOAC). The fatty acid profile of test sample was measured using AOAC method reference #969.33.

Example 10

Fatty Acid Analysis of Freeze-Dried Jucara Fruit

Fatty acid analysis of freeze-dried Jucara fruit was performed by Silliker, Inc. Illinois Laboratory (Chicago Heights, Ill.; laboratory ID No. 171378575). The results are detailed below in Table 16, Table 17 and Table 18.

TABLE 16

| SATURATED FATTY ACID | FORMULA | % |
|---|---|---|
| Butyric | 4:0 | <0.1 |
| Captoic | 6:0 | <0.1 |
| Caprylic | 8:0 | <0.1 |
| Capric | 10.0 | <0.1 |
| Undecanoic | 11:0 | <0.1 |
| Lauric | 12:0 | 0.1 |
| Tridecanoic | 13:0 | <0.1 |
| Myristic | 14:0 | 0.1 |
| Pentadecanoic | 15:0 | <0.1 |
| Palmitic | 16.0 | 24.1 |
| Marganic | 17:0 | 0.1 |
| Stearic | 18:0 | 1.7 |
| Nonadecanoic | 19:0 | <0.1 |
| Eicosanoic | 20:0 | 0.2 |
| Behenic | 22:0 | <0.1 |
| Tricosanoic | 23.0 | <0.1 |
| Lignoceric | 24:0 | <0.1 |

TABLE 17

| MONOUNSATURATED FATTY ACID | FORMULA | % | POLYUNSATURATED FATTY ACID | FORMULA | % |
|---|---|---|---|---|---|
| Tridecenoic | 13:1 | <0.1 | Linoleic | 18:2 | 10.0 |
| Myristoleic | 14:1 | <0.1 | Linolenic | 18:3 | 1.1 |
| Pentadecenoic | 15:1 | <0.1 | Gamma Linolenic | 18:3G | <0.1 |
| Palmitoleic | 16:1 | 4.3 | Eicosadienoic | 20:2 | <0.1 |
| Margarolleic | 17:1 | 0.1 | Eicosatrienoic | 20:3 | <0.1 |
| Oleic | 18:1C | 56.2 | Homogamma Linolenic | 20:3G | <0.1 |
| Elaidic | 18:1T | <0.1 | Arachidonic | 20:4 | <0.1 |
| Gadoleic | 20:1 | <0.1 | Eicosapentaenoic | 20:5 | <0.1 |
| Erucic | 22:1 | <0.1 | Docosadienoic | 22:2 | <0.1 |
| Nervonic | 24:1 | <0.1 | Docosahexaenoic | 22:6 | <0.1 |

TABLE 18

| | |
|---|---|
| Total Polyunsaturated Fatty Acid | 11.10 |
| Total Monounsaturated Fatty Acid | 60.20 |
| Total Saturated Fatty Acid | 28.70 |

Unless otherwise specified, all methods were performed as described in the Official Methods of Analysis of AOAC International, 17th Edition, 2000 (hereinafter, AOAC). The fatty acid profile of test sample was measured using AOAC method reference #969.33.

Example 11

Amino Acid Analysis of Freeze-Dried Açai

I. Amino Acid Analysis by Ion-Exchange Chromatography with Post-Column Derivation Amino acid analysis was performed by the general procedures described below.

A. Principle

This method quantitatively determines amino acid content by hydrolysis with 6N hydrochloric acid followed by ion-exchange chromatography. O-phthaldehyde is used for post-column derivation and subsequent fluorometric detection.

B. Scope

This procedure is applicable to ingredients, mixed feeds protein containing substance.

C. Critical Points

Avoid excess evaporation time while drying samples. The loss of some amino acids may take place.

D. Reagents and Chemicals and Protocol

1. Water, HPLC grade, EM Science EM WX0004-1 or in-house water purification system.
2. O-phthaldehyde, reagent grade, Anresco 0317.
3. Amino Acid standard solution, 2.5 pmoles/mL, Sigma A9531.
4. Methanol, HPLC grade, chempure 831-295 or equivalent.
5. Brij 3 solution, 30% (w/w), Sigma 430Agr.6
6. 2-Mercaptoethanol, (2-Hydroxyethylmercaptan), Sigma M-6250.
7. L-Norleucine, Sigma N-6877.
8. Pickering buffers, pH 2.2, 3.28, and 7.40, Picketing laboratories Na 220, Na 328, and Na 740.
9. Potassium hydroxide, pellets, Chempure 831-706.
10. Sodium hydroxide, pellets, Chempure 832-050.
11. Hydrochloric acid, 6 N volumetric solution, Chempure RR-155.
12. Ethylenediaminetetraacetic Acid EDTA Tetrasodium salt, hydrate, Sigma ED4SS.
13. Nitrogen source.
14. Boric acid, Chempure 830-314.
15. Norleucine Internal Standard—Weigh on an analytical balance to 0.1 mg, 0.1640 g of Norleucine. Transfer to 1000 mL volumetric flask. Add 250 mL HPLC water. Add 1 mL concentrated hydrochloric acid and mix. Make to volume with HPLC water, mix and sonicate. This solution will contain 1.25 pxn/mL L-Norleucine. Refrigerate to avoid bacterial growth.
16. Amino Acid Standard Solution—Warm the vial of amino acid standard solution to room temperature. Pipes 5.0 mL into a 50 ml. volumetric flask. Pipet 10.0 mL of 1.25 pm/mL L-Norleucine internal standard into the same 50 mL flask. Make to volume with HPLC water. Mix well and sonicate for several minutes. Transfer the standard into 4 mL Waters sample vials. Store at 0 degrees C.
17. Potassium hydroxide solution, 50%—On a top loading balance, weigh 150 g of potassium hydroxide into a tared 1-liter Nalgene container. Dissolve with 150 g of deionized water, stir as necessary. Allow the solution to cool to room temperature before usage.
18. Boric acid buffer—Weigh 122 g of boric acid into a tared 2000 ml beaker and add 1800 ml. of HPLC water. Adjust the pH to 11.0 with 50% potassium hydroxide solution. Transfer the solution to a 4-liter glass jug and fill to volume (4 liters) with HPLC water and mix well. The final solution pH should be 10.4.
19. Pickering Buffer Mobile Phase:
   a. pH 3.28—This buffer may be used as is from the bottle. Filter through a 0.45 pm filter membrane and degas prior to HPLC usage by vacuum under sonication.

b. pH 7.40—This buffer may be used as is from the bottle. Filter through a 0.45 pm filter membrane and degas prior to HPLC usage by vacuum under sonication.

20. Sodium hydroxide, 0.2 N—Weigh 16 g sodium hydroxide pellets into a 2-liter volumetric flask. Add approximately 1000 mL HPLC water and mix until the sodium hydroxide is dissolved. Weigh 0.5 g EDTA, add to the volumetric. Make to volume with HPLC water, mix and filter through a 0.45 mm filter membrane. Use plastic gallon jug as a reservoir for HPLC. Filter periodically.

21. O-phthaldehyde Weigh 1.4 g of o-pbthaldehyde (OPA) crystals into a 50 mL beaker. Add 20 mL HPLC grade methanol and sonicate until the crystals are dissolved. Add solution to a 2-liter volumetric flask containing approximately 1500 ml of boric acid buffer and mix. In a hood, add 4.0 mL 2-mercaptoethanol. Fill to volume with boric acid buffer and mix. Filter the solution through a 0.45 pm filter. Pour the filtered solution into two 1-liter Nalgene bottles and add 3.0 mL Brj-35 to each bottle. Cap the bottles with nitrogen and mix well. Refrigerate until needed. OPA solution is stable for approximately 1 week under these conditions (may extend up to 2 weeks).

E. Equipment and Apparatus

1. Waters model 712 B autoinjector or equivalent.
2. Waters model 6000 pump (2), Waters 2100 or equivalent.
3. Digital Pro 380 with Waters Expert software or equivalent.
4. Kratos FS-950 fluorometric detector or equivalent.
5. Kratos URS 051 post column pump or equivalent.
6. Fiatron column heater, Eppendorf CII-30 or equivalent.
7. Fisher Isotemp Oven, model 215 P or equivalent.
8. Savant Speed Vac Concentrator, model SVC-20011.
9. Savant refrigerated condensation trap, model RT-490.
10. Savant chemical trap, model SCT-120.
11. Savant disposable cartridge for acid vapor neutralization, model DC12OA.
12. Precision direct drive vacuum pump, model Dd-310 or equivalent.
13. Vacuum gauge, Waters Pico-Tag work station or equivalent.
14. Glass-Col small pulsing vortexer, model S8216, Glas-Col PV6.
15. Beckman pH140 Meter, Beckman 123118 or equivalent.
16. Mettler Analytical balance, model AE16O or equivalent.
17. Millipore solvent filtration apparatus, Waters 85116.
18. Interaction-Sodium loaded ion exchange column, with guard column. Interaction Chromatography AMI 1.
19. Bransonic Ultrasonic bath model 220.
20. Mettler top loading balance, model P-1000.
21. Pipeman. Gilson, 1 ml and 5 ml, Rainin P4000 and P-5000.
22. Universal lit pipes tips, 1 mL SoS mL, Rainin.
23. Plastipak syringe with Luer-Lok, 3 cc×1/10 cc, BI) 9585 or equivalent.
24. Syringe filters, polypropylene, Teflon, 0.45 micron, Nalgene 199-2045.
25. Magna Nylon 66 membrane 47 mm diameter, 0.45-micron pore size, Fisher N045P0410.
26. Repipet II Dispenser, S mL, Fisher 13-687-62A.
27. Universal fir pipes tips, 200-100C) d. VWR 53508-819.
28. Disposable culture tubes, 12×75 mm, borosilicate glass, VWR 60825-550 or equivalent.
29. Sample vial assembly, 4 mL, includes taps and PFTE septa, Waters 73018.
30. Low volume insert with springs, plastic, for 4 mL sample vial. Waters 72163.
31. Firestone valve, rapid purge, Ace Glass mc, 8766.
32. Culture tubes, disposable, 20×150 mm, screw cap, borosilicate glass, VWR 60826.280.
33. Screw caps for disposable culture tubes, 20 mm PTFB liner, VWR 60828-570.
34. Brinkman centrifugal mill, model ZM-1 (with 0.5 ruin screen) or equivalent.

F. Sample Preparation

The sample was ground as fine as possible while keeping moisture loss to a minimum. The sample was ground through a Brinkman Centrifugal Grinding mill model ZM-1, or equivalent, using a 0.5 mm screen to obtain a fine grind.

G. Procedure

1. The analytical balance was calibrated and set to zero.
2. It is helpful to have knowledge of the protein content of the sample before weighing for amino acid analysis. With this in mind, the sample equivalent to 20 mg protein was weighed on an analytical balance. (Refer to the supplement for Free Amino Acid Determination.) For a nearly pure sample, approximately 38 mg was weighed. The weight was recorded in a laboratory notebook. The sample was then quantitatively transferred to a marked 20×150-turn screw top culture tube.
3. Using the Repipet II Dispenser, 15 mL 6 N hydrochloric acid was added to each culture tube. Because of the grind and limited amount of sample taken, any drafts that might cause a loss of sample from the culture tube were avoided.
4. In the hood, 75 microliter of 2-mercaptoethanol was added to each culture tube (Note 1). This allowed for better determination of the L-methionine peak.
5. Each culture tube was firestoned (Note 2), alternating between nitrogen (10-12 psi) and vacuum at least 5 times each.
6. While the sample was under nitrogen, PTFE-faced cap were screwed on.
7. Culture tubes were placed in an oven at 110 degrees C.±2 degrees C. for 24 hours.
8. The Savant evaporation system was assembled. The power to the system was started at least 2 hours prior to usage, so the refrigeration unit has a sufficient amount of time to attain the final working temperature of −92 degrees C. Oil in the vacuum pump was thoroughly degassed. This was done, as needed, by opening the gas ballast valve on the pump and switching the pump on. One hour was generally sufficient. The pump was turned off and the gas ballast valve was closed upon completion.
9. After 24 hours, the culture tubes were removed from the oven and allowed to cool to room temperature.
10. 5 mL of HPLC grade water was added to each culture tube. The cap was screwed on and mixed well.
11. 5 mL of Norleucine Internal standard (1.25 pm/mL) was added to each culture tube (Note 3). (At this point the analysis may be stopped until the following day if necessary. Store the culture rube at 0 degrees C. if you need to store overnight.)
12. Using a 1 mL pipetman, 2 mL of hydrolysate was transferred into a marked 12×75 mm disposable culture tube.
13. The lid to the speed vac concentrator was opened and tubes containing the 2 mL of hydrolysate were placed into positions around the rotor so that the load was well balanced.
14. The lid was closed, the vent opened and the centrifuge was started. When the rotor reached its operating rpms, the vent on the vacuum gauge was closed and the vacuum pump was started. The evaporation process may take place overnight, if necessary. This would be so, if many samples were evaporated, starting late in the day (Note 4).

15. When samples are dry (vacuum gauge reads less than 500 milliliter), the vent was slowly opened to bleed air into the chamber. The pump was turned off and, once the chamber had been completely vented, the centrifuge was turned off, the tubes removed.

16. 3 mL of Pickering sodium diluent 220 was added to each tube and momentarily sonicate prior to vortexing.

17. A 0.45 pm filter was attached to a 3 mL syringe. The prepared hydrolysate was filtered into a marked 4 mL vial containing a Waters Low volume insert with spring, then place on 712B WISP autosampler tray.

18. HPLC Conditions:

a. All buffer and OPA solutions were degassed by sonication under vacuum. The buffer lines were placed into appropriate buffer solution and OPA line into OPA solution. The column was equilibrated with buffers 3.28 with the flow rare at 0.5 mL/minute for at least 20 minutes.

b. The sensitivity control on fluorometer was set to 450, range to 0.5, time constant to 1 second, background suppression to "to".

c. The column heater temperature was set at 60 degrees C. and monitored during the run.

d. The OPA pump was started and the flow rate was set to 0.50 mL/minute (adjusting downward as necessary).

e. A standard was placed in position #1 and #2 on WISP. Multi method and/or method table were built and 20 F1 of standard was injected. Allowed 60 minutes for run dine. Observed resulting chromatogram. Injected a third time if chromatography is not satisfactory.

f. Ran a standard after every five samples. Updated response factors will be generated and used for subsequent injections.

g. If the peak was outside the window, the samples were reprocessed and the retention time was adjusted in calibration table to march that of the sample. New corrected chromatogram were printed and stored.

h. Gradient elution using 2 buffers: Using Waters software, a satisfactory gradient was established using 2 buffers for elation of amino acids. Pump Table 19 follows:

TABLE 19

Pump Table Standard Profile

| Time | Flow | % A | % B | Curve No. | Total Flow |
|---|---|---|---|---|---|
| Initial | 0.500 | 100 | 0 | — | 0.500 |
| 35.0 | 0.500 | 0 | 100 | 6 | 0.500 |
| 45.0 | 0.500 | 0 | 100 | 11 | 0.500 |
| 45.5 | 0.500 | 100 | 0 | 11 | 0.500 |

Where A = Pickering Buffer Na 328;
B = Pickering Buffer Na 740

J. Calculations

Response factor=Amount amino acid (mg)×Area norleucine (internal standard)

Area Amino Add

Then RF×Area amino acid sample=Concentration of amino acid (mg)

Area Norleucine Internal Standard

Since the sample volume determines the final concentration, concentration of amino acid times the sample volume=final concentration of amino acids.

K. Notes

1. Mercaptoacetic acid may be used instead, if necessary—if used Brij-35-dad to preserve Lrs quek.

2. The Firestone process consisted of alternately evacuating and purging with nitrogen the acid-sample solution in a sonic bath. This degassed the solution and created an inert atmosphere above the acid thus minimizing oxidation of the amino acids during hydrolysis.

3. Using a 5 mL pipetman, calibrate with room temperature water to 5.000B±0.005 g.

4. With good vacuum, samples may freeze in the tubes. If so, after approximately 45 to 60 minutes, remove the tubes and warm hydrolysate in a beaker which contains hot water. Place tubes back into the rotor and continue evaporation.

L. Validation

M. Quality Control

1. Follow the standard quality assurance practices detailed in the Quality Assurance Manual.

2. A control standard (secondary standard) should be included in each run of samples. Casein is currently used as a control.

3. Results of the control standard are to be recorded in the laboratory notebook.

4. Duplicate runs of the standard should not vary by more than 8%.

5. Notebooks are to be initialed and dated by the analyst performing the test

6. Notebook entries are to be reviewed, understood, initialed and dated by another analyst in the department.

N. References

1. JAOAC: Vol 65, No. 2, 1982, Pp 496-497. Calculated Protein Efficiency Ration.
2. Degussa—Literature Digest for the Feedstuffs Industry—Amino Acid Analysis. Chemie/Anwendungstechnik Hanau Stadtteil Wolfgang, Fed. Rep. of Germany.
3. The Peptides, Vol. 4, Amino Acid Analysis of Peptides, Ch 5. pp 217-259, J R Benson, P. C. Louie and L A. Bradsbaw. Copyright 1981, Academic Press, Inc.
4. USDA Chemistry Laboratory Guidebook, G-41
5. IAOAC: Vol. 68, No. 5, 1985, pp 811-821. Sample Preparation for Chromatography of Amino Acids: Acid Hydrolysis of Proteins.

II. Amino Acid Analysis of Freeze-Dried Açai Pulp

Amino acid analysis of freeze-dried Açai pulp was performed by Silliker, Inc. Illinois Laboratory (Chicago Heights, Ill.; laboratory ID No. 170547512). The results are detailed below in Table 20.

TABLE 20

| Analyte - Amino Acids Complete* | Results** |
|---|---|
| Aspartic Acid | 0.83 |
| Threonine | 0.31 |
| Serine | 0.32 |
| Glutamic Acid | 0.80 |
| Glycine | 0.39 |
| Alanine | 0.46 |
| Valine | 0.51 |
| Methionine | 0.12 |
| Isoleucine | 0.38 |
| Leucine | 0.65 |
| Tyrosine | 0.29 |
| Phenylalanine | 0.43 |
| Lysine | 0.66 |
| Histidine | 0.17 |
| Arginine | 0.42 |
| Proline | 0.53 |
| Hydroxyproline | <0.01 |
| Cystine | 0.18 |
| Trypotophan | 0.13 |

*Reference Method - USDA 6.011 (1986)
**Amino acid analysis data are presented as wt/wt % (g/100 g).

Example 12

Amino Acid Analysis of Freeze-Dried Jucara Fruit

Amino acid analysis of freeze-dried Jucara fruit was performed by Silliker, Inc. Illinois Laboratory (Chicago Heights, Ill.; laboratory ID No. 171378575; as detailed in Example 11). The results are detailed below in Table 21.

TABLE 21

| Analyte - Amino Acids Complete* | Results** |
|---|---|
| Aspartic Acid | 0.12 |
| Threonine | 0.04 |
| Serine | 0.05 |
| Glutamic Acid | 0.10 |
| Glycine | 0.04 |
| Alanine | 0.05 |
| Valine | 0.05 |
| Methionine | 0.02 |
| Isoleucine | 0.03 |
| Leucine | 0.06 |
| Tyrosine | 0.02 |
| Phenylalanine | 0.04 |
| Lysine | 0.05 |
| Histidine | 0.02 |
| Arginine | 0.04 |
| Proline | 0.05 |
| Hydroxyproline | <0.01 |
| Cystine | 0.03 |
| Trypotophan | 0.06 |

*Reference Method - USDA MSS2 (1993)
**Amino acid analysis data are presented as wt/wt % (g/100 g).

Example 13

Comparative Analysis of the Antioxidant Potential of Freeze-Dried Açai and Select Vegetables by $ORAC_{FL}$ Analysis I. General ORAC Assay The ORAC Assay was developed by Cao et al., and first reported in 1993: "Cao G, Alesslo H M, Cutler R G, Oxygen radical absorbance capacity assay for antioxidant: Free Rad. Biol. Med. 1993:14:303-11'. Modifications were made to automate the analytical procedure and were reported in the literature in 1995: "Automated Assay of Oxygen Radical Absorbance Capacity with the COBAS FARA II Guohua Cao, Carl P. Verdon. Akin H. B. WU, Hong Wang and Ronald L. Prior, CLINICAL CHEMISTRY, Vol. 41, No. 12, 1995".

From that point forward, the Automated ORAC Assay received extensive coverage and utilization, and as such, ORAC values have become commonplace in research and in the marketing of natural products. Brunswick Laboratories purchased two COBAS FARA 11 analyzers in 1997, replicated the automated method as developed by Cao, Prior, et al, and to date, has established an antioxidant database consisting of over 5000 points of ORAC data for fruits, vegetables, beverages, grains functional/engineered foods, extracts, and other natural product sources.

Brunswick Laboratories, working with the USDA, introduced a new fluorescence probe, fluorescein, which has been tested with several hundred samples, in side-by-side comparison with beta-Phycoerythrin. Fluorescein, unlike beta-PE, does not interact with the tested samples, and being a synthetic compound, fluorescein has no measurable variability from lot-to-lot. Most importantly, samples tested multiple times under the same conditions maintain consistent and repeatable results.

The development of the ORAC assay using fluorescein as the fluorescence probe has been conducted in cooperation with the developers of the original automated ORAC Assay, where beta-PE was utilized as the fluorescence probe. Based on the extensively mechanistic studies, both patties lock to-the fluorescein based ORAC assay as being the new standard ORAC procedure. The two ORAC assays are distinguished herein by using the subscripts PE for phycoerythrin, and FL for fluorescein—$ORAC_{PE}$ and $ORAC_{FL}$.

II. Analysis of Freeze-Dried Açai Powder and Comparison with Select Vegetables

Figure 10:
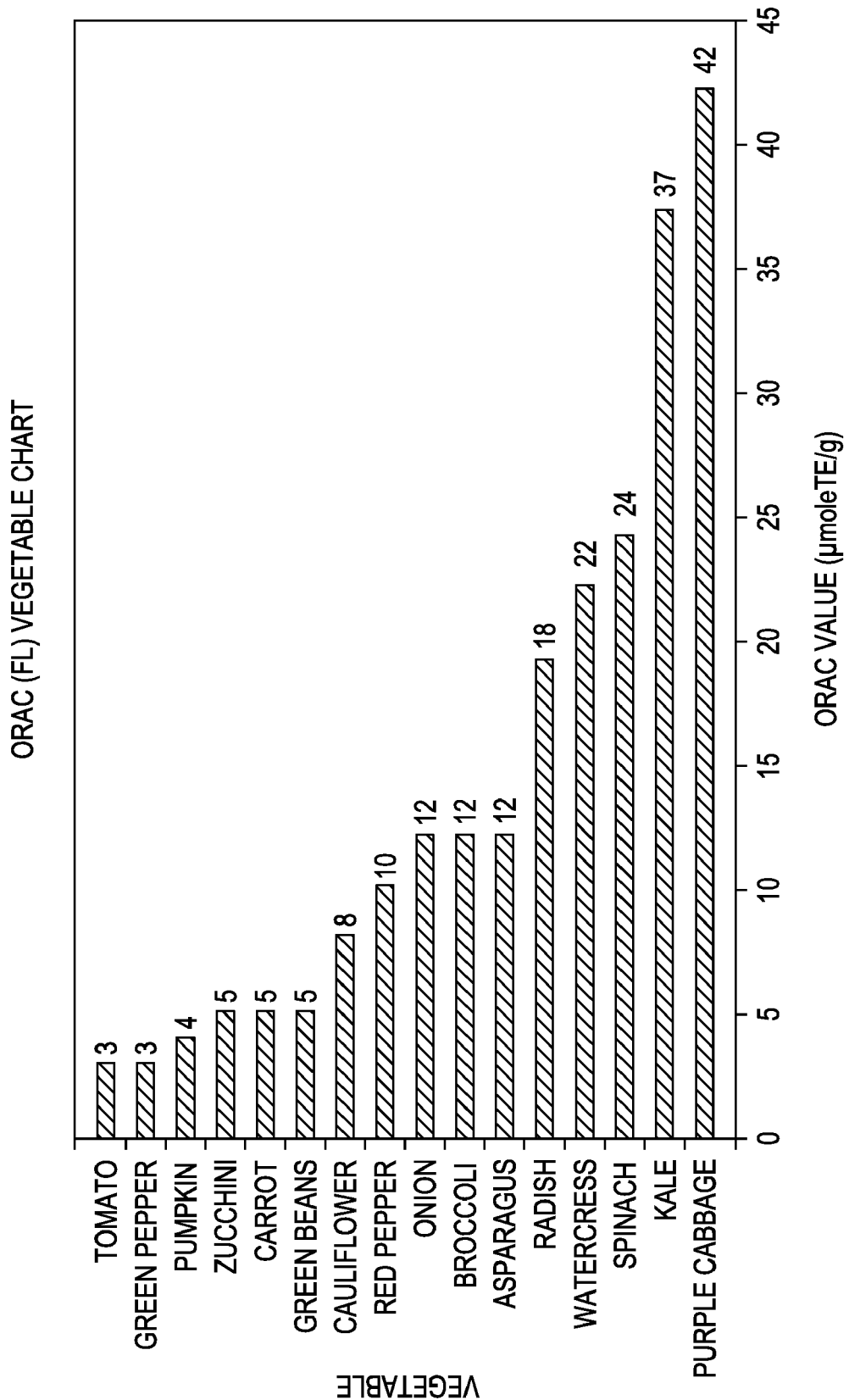
FIG. 10 is a histogram graph comparing the antioxidant activity of select vegetables as determined by ORAC analysis technique.

The antioxidant activity of freeze dried Açai powder (Brunswick Lab ID. $O_2$-0104; Brunswick Laboratories, Wareham, Mass.) was compared with the antioxidant activity of select vegetables as determined by $ORAC_{FL}$ analysis technique (as detailed above) (FIG. 10). The ORAC value of freeze-dried Açai powder was measured as 442 µmole TE/g. This value was more than 10-fold greater than the ORAC value of purple cabbage (42 µmole TE/g) (FIG. 10). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 14

Figure 11:
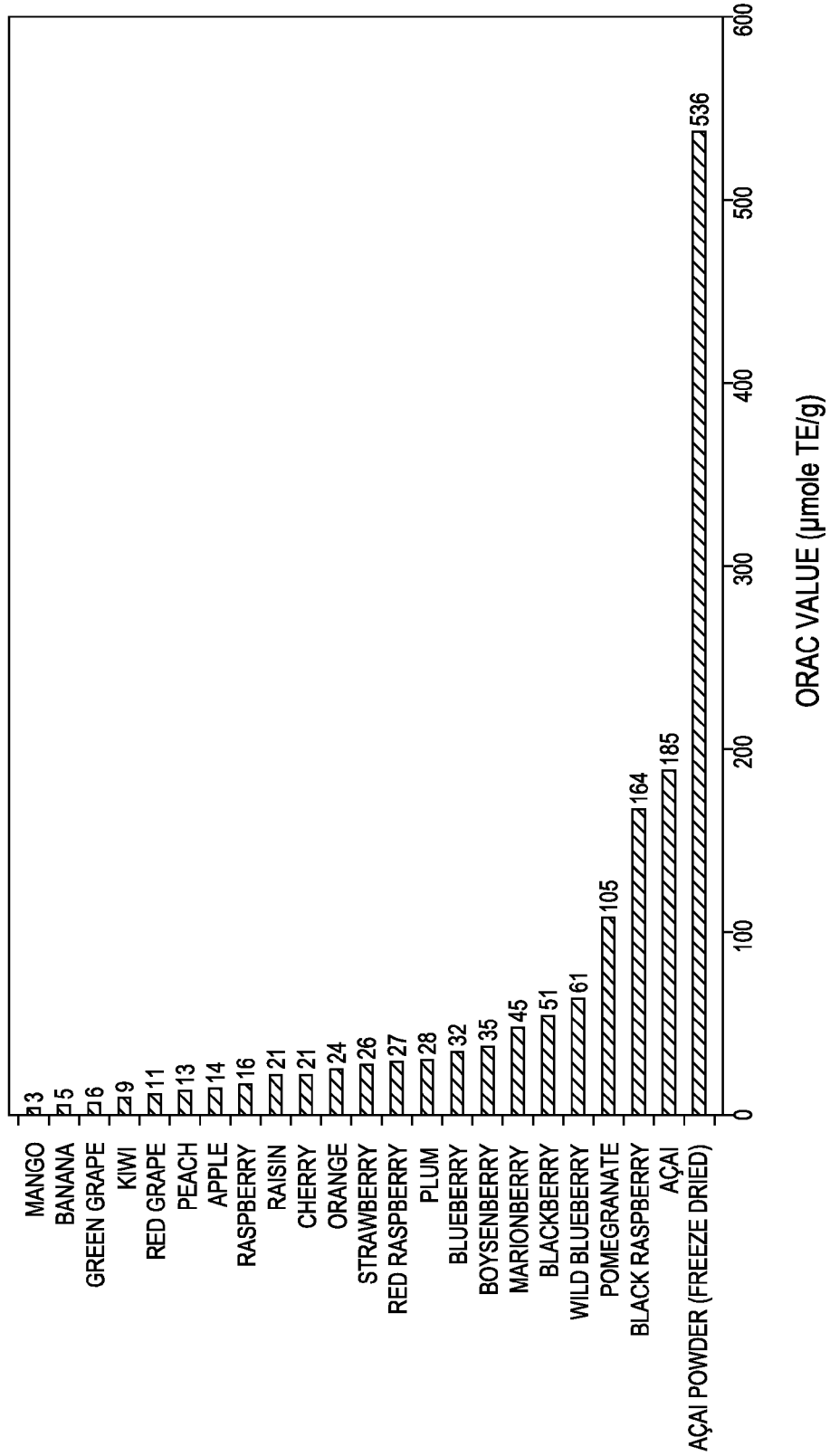
FIG. 11 is a histogram graph comparing the antioxidant activity select fresh fruits as determined by ORAC analysis technique.

Comparative Analysis of the Antioxidant Potential of Freeze-Dried Açai and Select Fresh Fruits by $ORAC_{FL}$ Analysis The antioxidant activity of freeze dried Açai powder (231003/0410-C; Brunswick Lab ID. 03-2096; Brunswick Laboratories, Wareham, Mass.) was compared with the antioxidant activity of select fresh fruits as determined by $ORAC_{FL}$ analysis technique (as detailed above) (FIG. 11). As shown in FIG. 11, the ORAC value of freeze-dried Açai powder (536 µmole TE/g) was more than 2-fold greater than the ORAC values of either fresh Açai (185 µmole TE/g) or black raspberry (164 µmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 15

Figure 12:
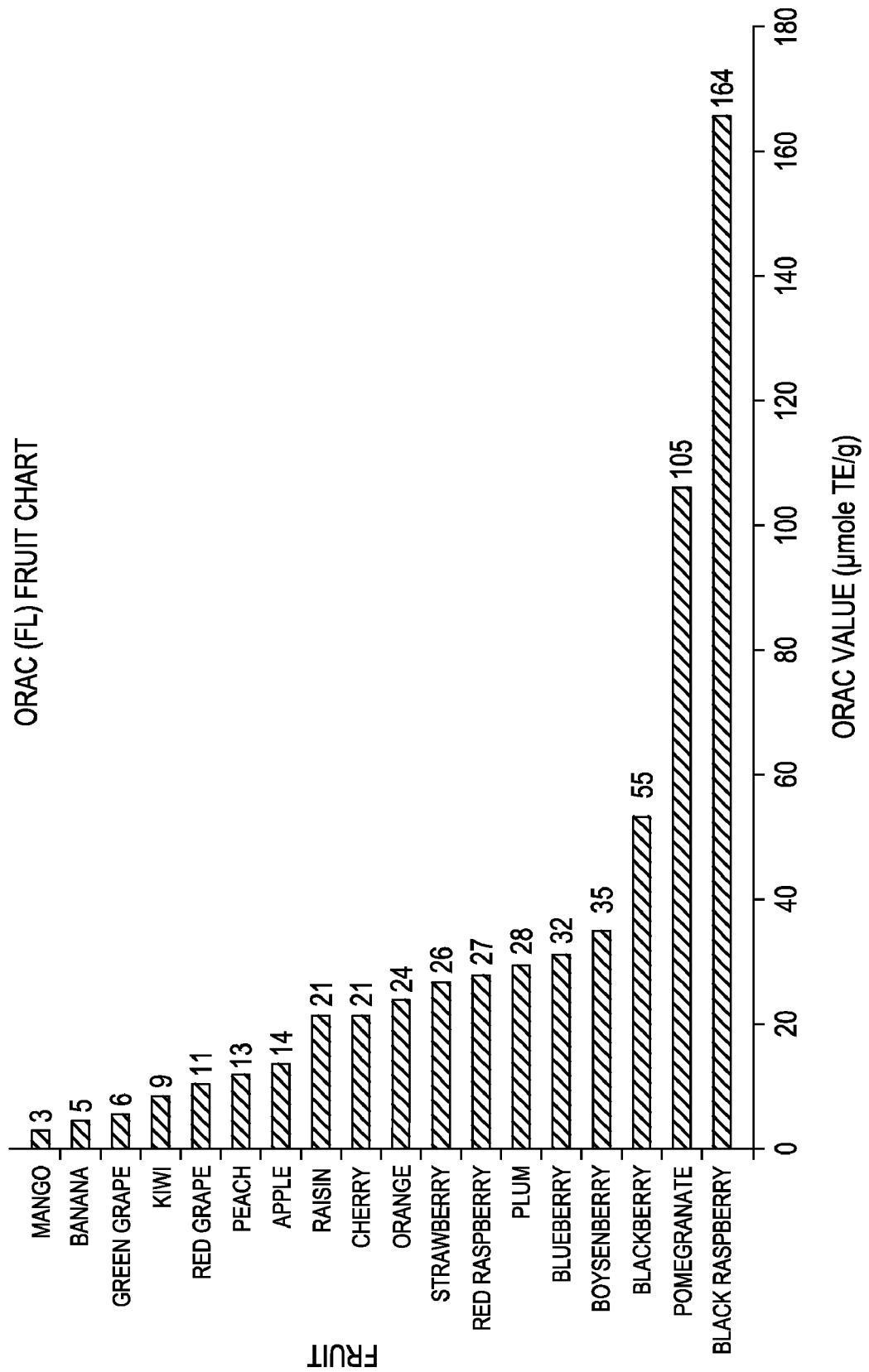
FIG. 12 is a histogram graph comparing the antioxidant activity of select fresh fruits as determined by ORAC analysis technique.

Comparative Analysis of the Antioxidant Potential of Freeze-Dried Açai and Select Fresh Fruits by $ORAC_{FL}$ Analysis The antioxidant activity of freeze dried Açai powder (Brunswick Lab ID. $O_2$-0104; Brunswick Laboratories, Wareham, Mass.) was compared with the antioxidant activity of select fresh fruits as determined by $ORAC_{FL}$ analysis technique (as detailed above) (FIG. 12). The ORAC value of freeze-dried Açai powder was 442 mole TE/g. This value was more than 2-fold greater than the ORAC value of black raspberry (164 µmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 16

Figure 13:
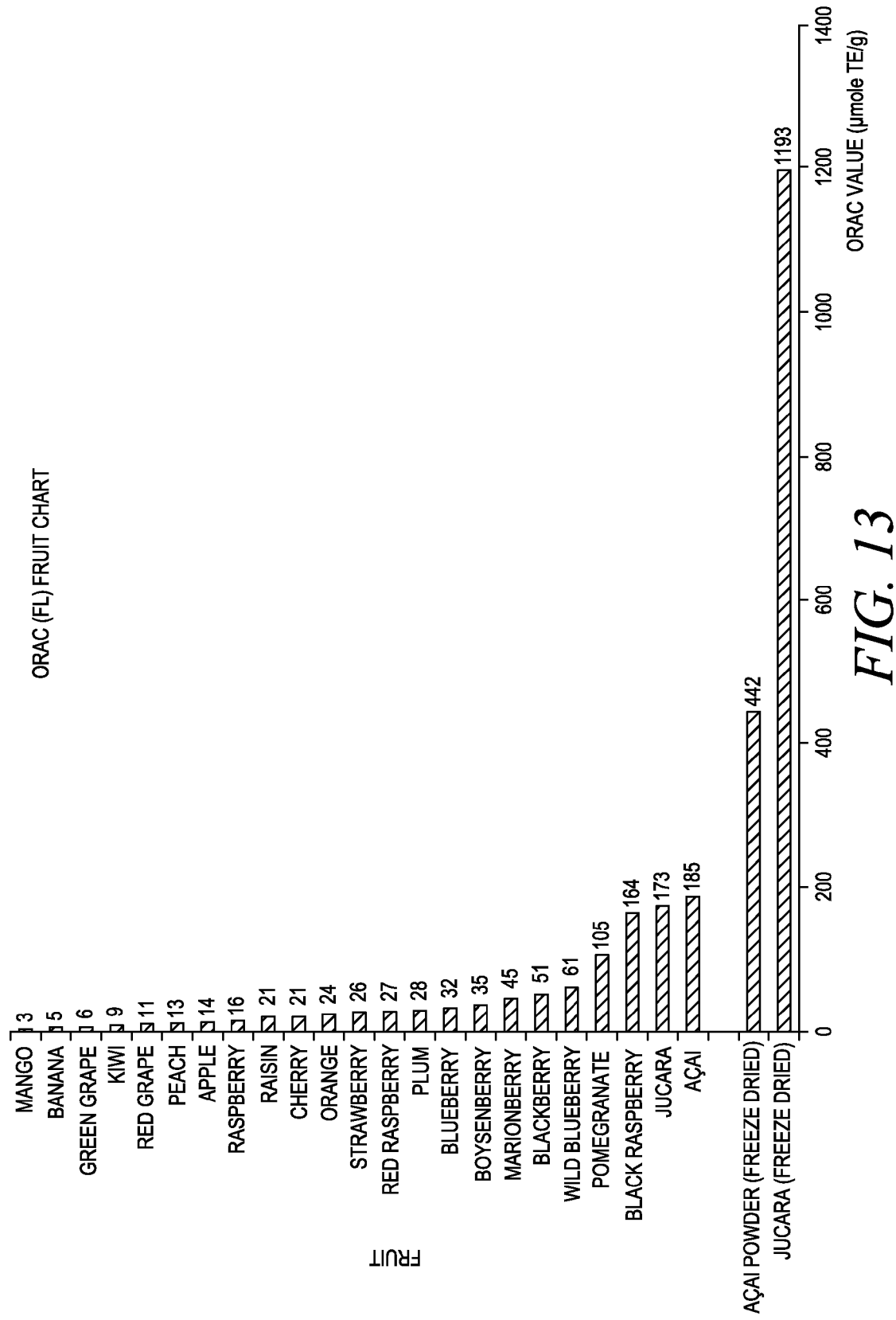
FIG. 13 is a histogram graph comparing the antioxidant activity of freeze-dried Açai powder and freeze-dried Jucara powder with select fresh fruits as determined by ORAC analysis technique.

Comparative Analysis of the Antioxidant Potential of Freeze-Dried Açai and Select Fruits by $ORAC_{FL}$ Analysis The antioxidant activity of freeze dried Açai powder (Brunswick Lab ID. $O_2$-0104; Brunswick Laboratories, Wareham, Mass.) was compared with the antioxidant activity of select fruits as determined by $ORAC_{FL}$ analysis technique (as detailed above) (FIG. 13). As shown in FIG. 13, the ORAC value of freeze-dried Açai powder was 442 μmole TE/g. The ORAC value for freeze-dried Jucara powder was 1193 TE/g. The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 17

Figure 14:
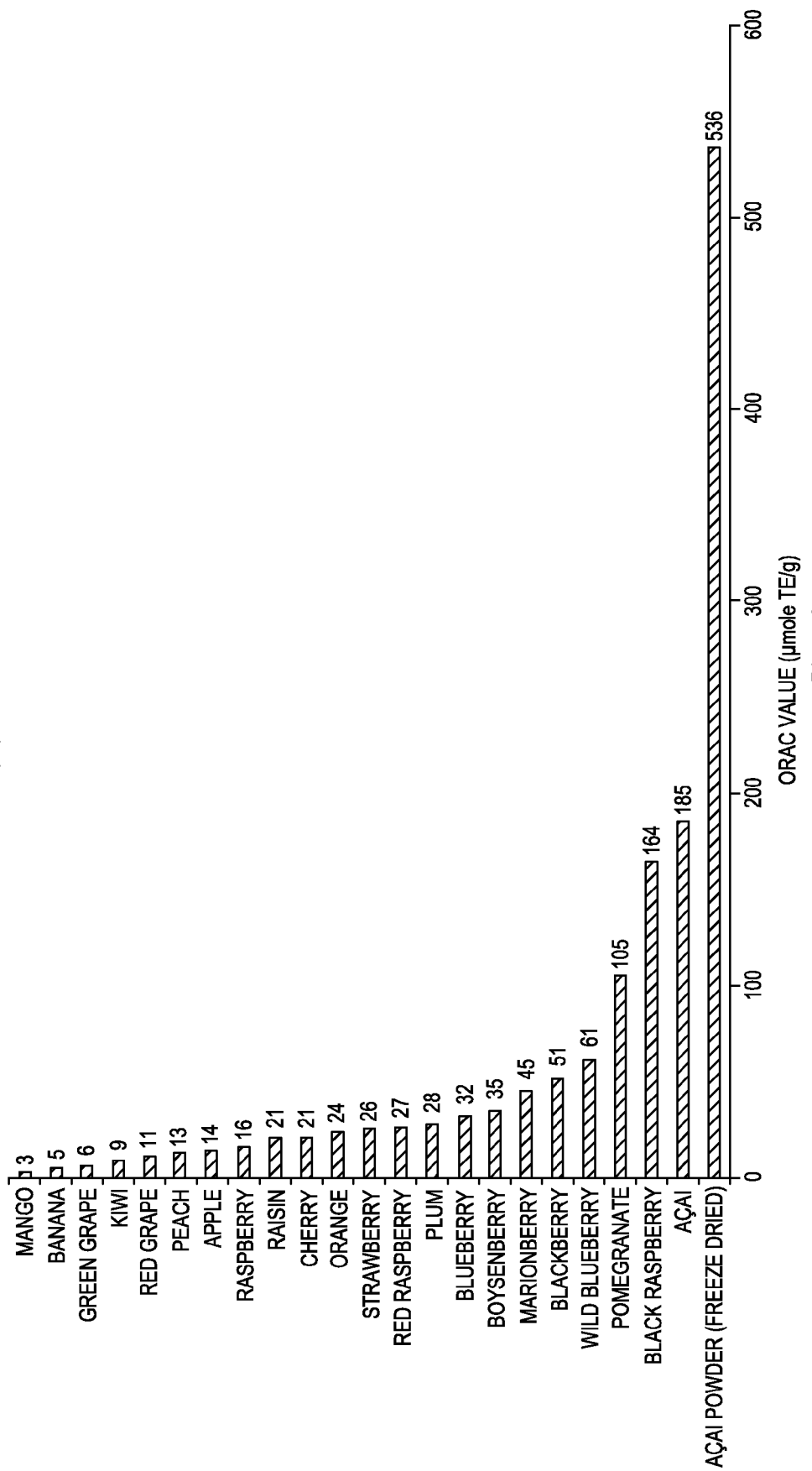
FIG. 14 is a histogram graph comparing the antioxidant activity of freeze-dried Açai with select fresh fruits as determined by ORAC analysis technique.

Comparative Analysis of the Antioxidant Potential of Dehydrated Açai and Select Fresh Fruits by $ORAC_{FL}$ Analysis The antioxidant activity of dehydrated Açai powder (23100/0410-C; Brunswick Lab ID 03-2096; Brunswick Laboratories, Wareham, Mass.) was compared with the antioxidant activity of select fresh fruits as determined by $ORAC_{FL}$ analysis technique (as detailed above) (FIG. 14). As shown in FIG. 14, the ORAC value of freeze-dried Açai powder (536 μmole TE/g) was more than 3-fold greater than the ORAC value of black raspberry (164 mole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 18

Figure 15:
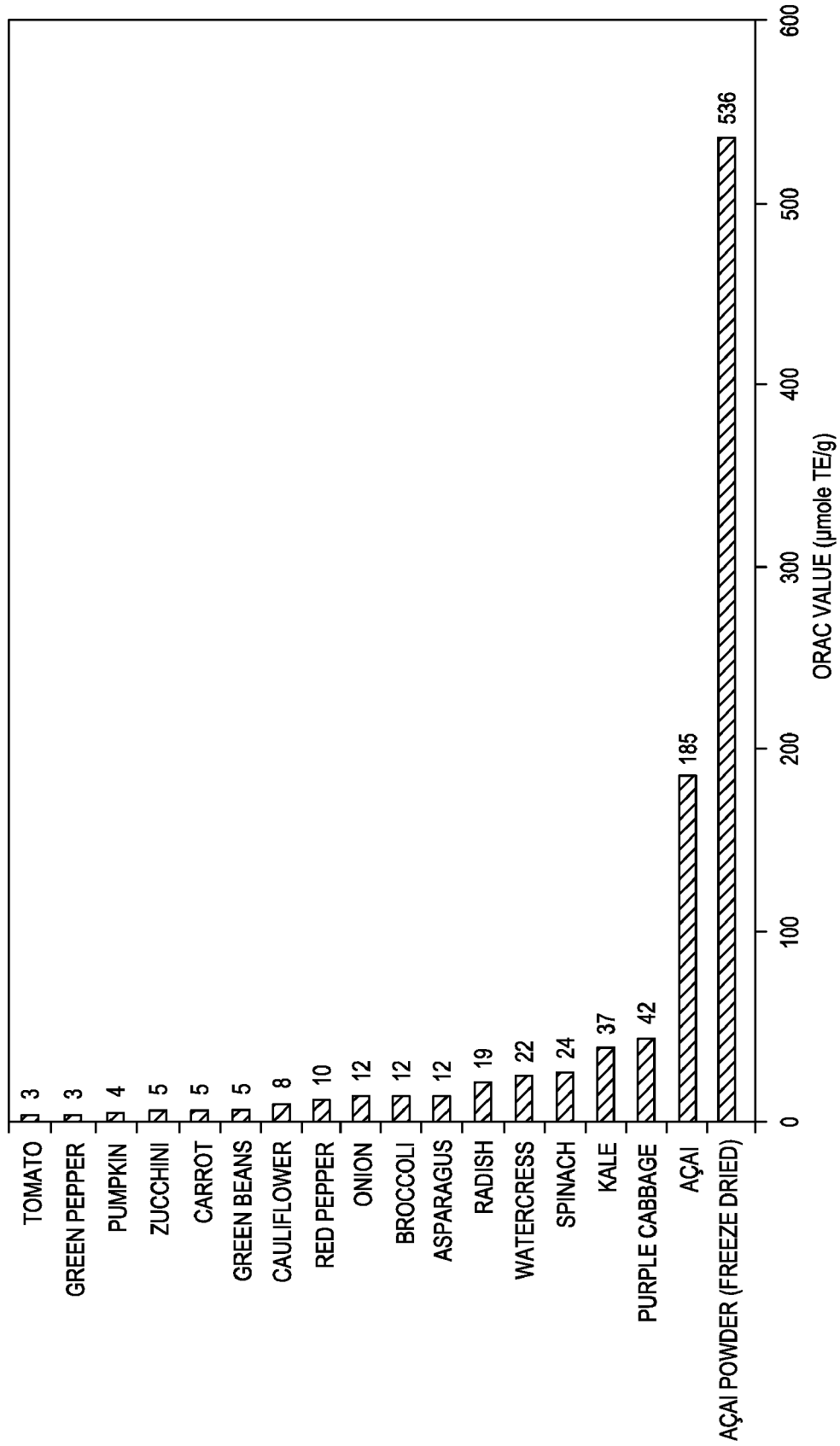
FIG. 15 is a histogram graph comparing the antioxidant activity of freeze-dried Açai powder with select fresh vegetables as determined by ORAC analysis technique.

Comparative Analysis of the Antioxidant Potential of Freeze-Dried Açai and Select Fresh Vegetables by $ORAC_{FL}$ Analysis The antioxidant activity of freeze dried Açai powder (231003/0410-C; Brunswick Lab ID. 03-2096; Brunswick Laboratories, Wareham, Mass.) was compared with the antioxidant activity of select fresh vegetables as determined by $ORAC_{FL}$ analysis technique (as detailed above) (FIG. 15). As shown in FIG. 15, the ORAC value of freeze-dried Açai powder (536 μmole TE/g) was more than 10-fold greater than the ORAC value of purple cabbage (42 μmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 19

Figure 16:
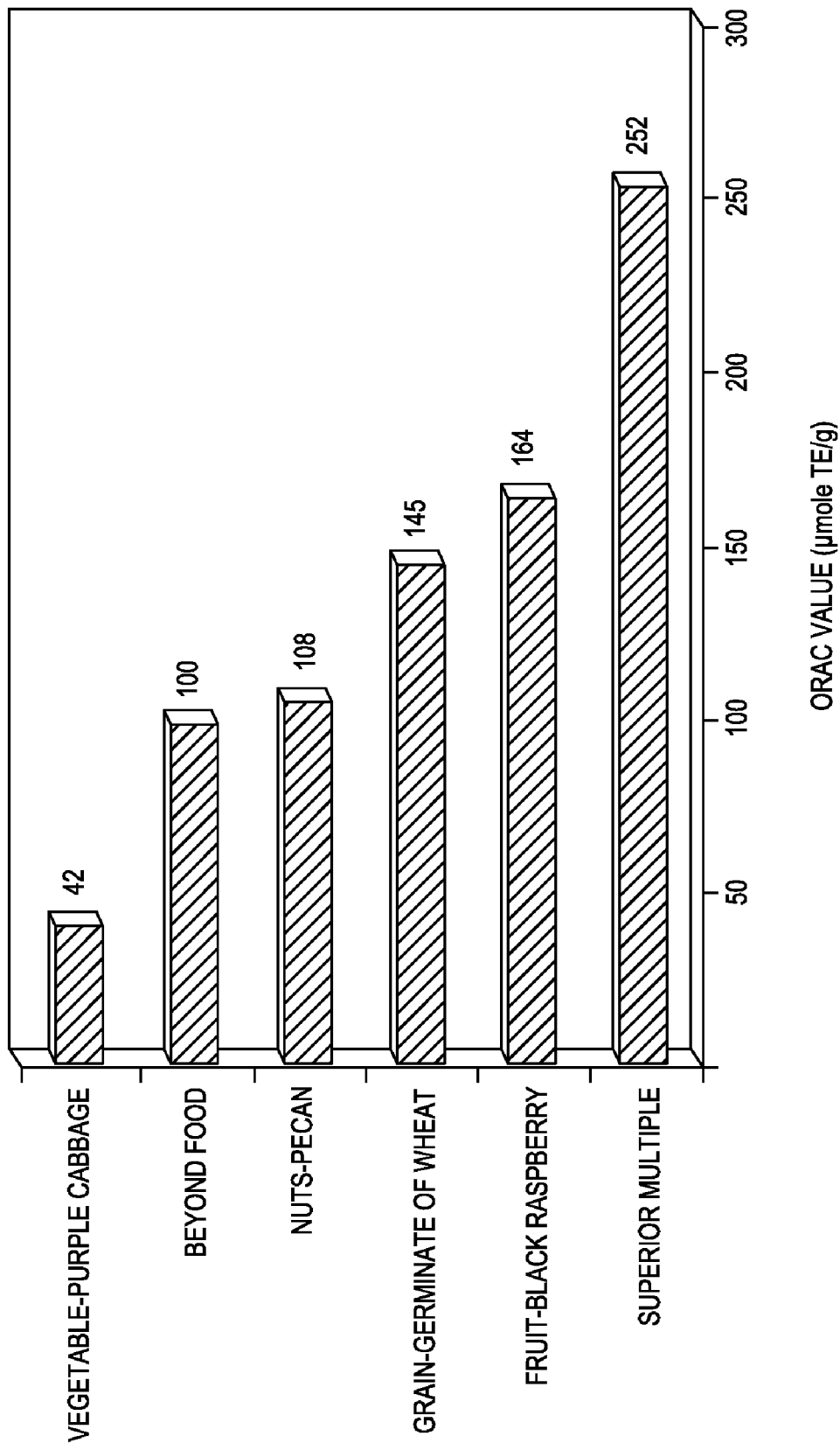
FIG. 16 is a histogram graph comparing the antioxidant activity of select fruits, vegetables and nuts as determined by ORAC analysis technique.

Comparative Analysis of the Antioxidant Potential of Select Fruits, Vegetables, and Nuts by ORAC Analysis FIG. 16 shows the antioxidant activity of fruits, vegetables and nuts as determined by ORAC analysis technique (Brunswick Laboratories, Wareham, Mass.; as detailed above). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 20

Figure 17:
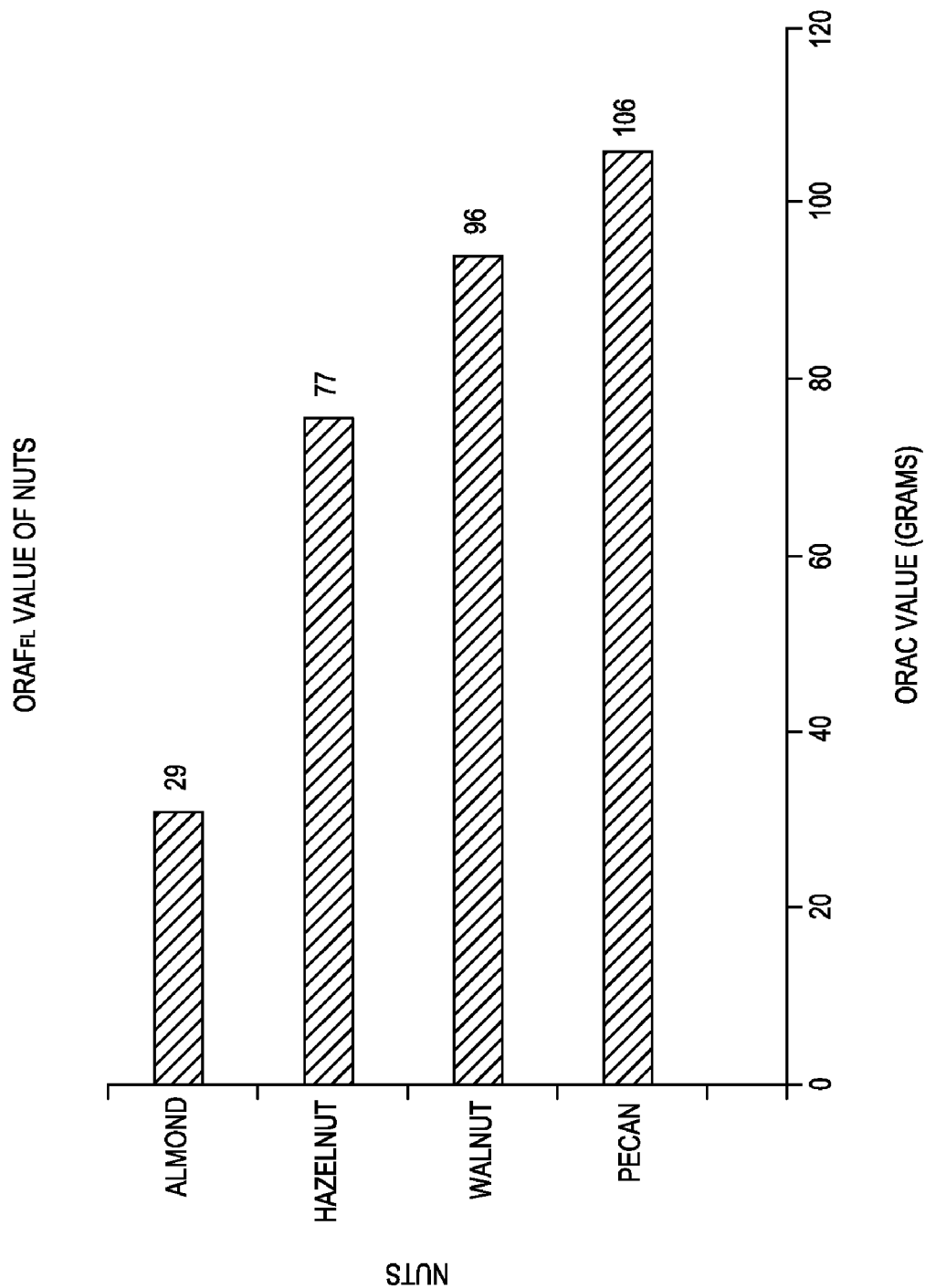
FIG. 17 is a histogram graph comparing the antioxidant activity of select nuts as determined by ORAC analysis technique.

Comparative Analysis of the Antioxidant Potential of Freeze-Dried Mai and Select Nuts by $ORAC_{FL}$ Analysis The antioxidant activity of freeze dried Açai powder (Brunswick Lab ID. $O_2$-0104; Brunswick Laboratories, Wareham, Mass.) was compared with the antioxidant activity of select nuts as determined by $ORAC_{FL}$ analysis technique (as detailed above). The ORAC value of freeze-dried Açai powder was 442 μmole TE/g. This value was more than 4-fold greater than the ORAC value of pecan (164 μmole TE/g) (FIG. 17). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 21

Figure 18:
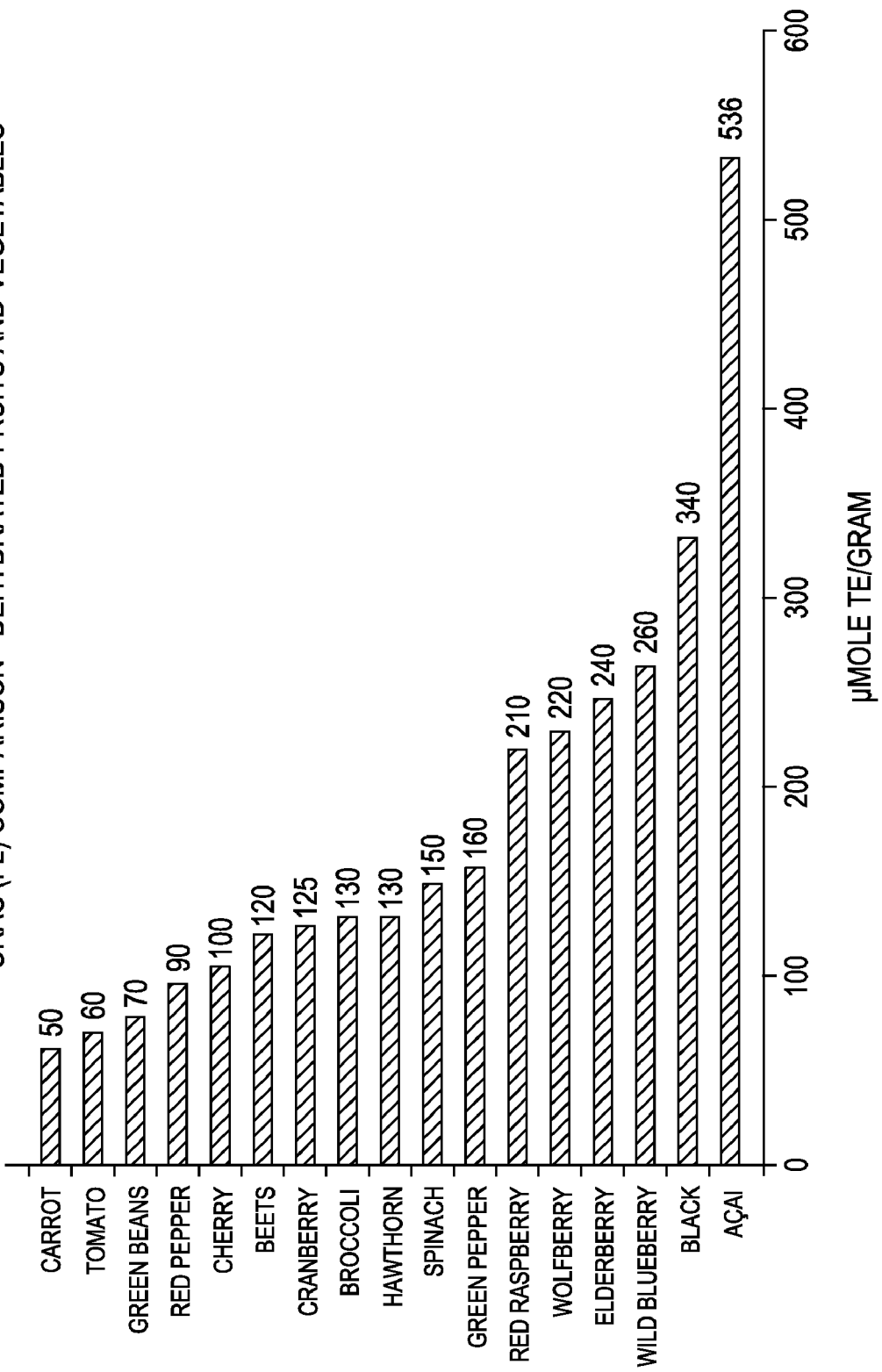
FIG. 18 is a histogram graph comparing the antioxidant activity of dehydrated Açai with select dehydrated fruits and vegetables as determined by ORAC analysis technique.

Comparative Analysis of the Antioxidant Potential of Dehydrated Açai and Select Dehydrated Fruits and Vegetables by $ORAC_{FL}$ Analysis The antioxidant activity of dehydrated Açai powder (Brunswick Laboratories, Wareham, Mass.) was compared with the antioxidant activity of select dehydrated fruits and vegetables as determined by $ORAC_{FL}$ analysis technique (as detailed above) (FIG. 18). As shown in FIG. 18, the ORAC value of dehydrated Açai powder (536 μmole TE/g) was greater than the ORAC value of dehydrated black raspberry (340 μmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 22

Figure 19:
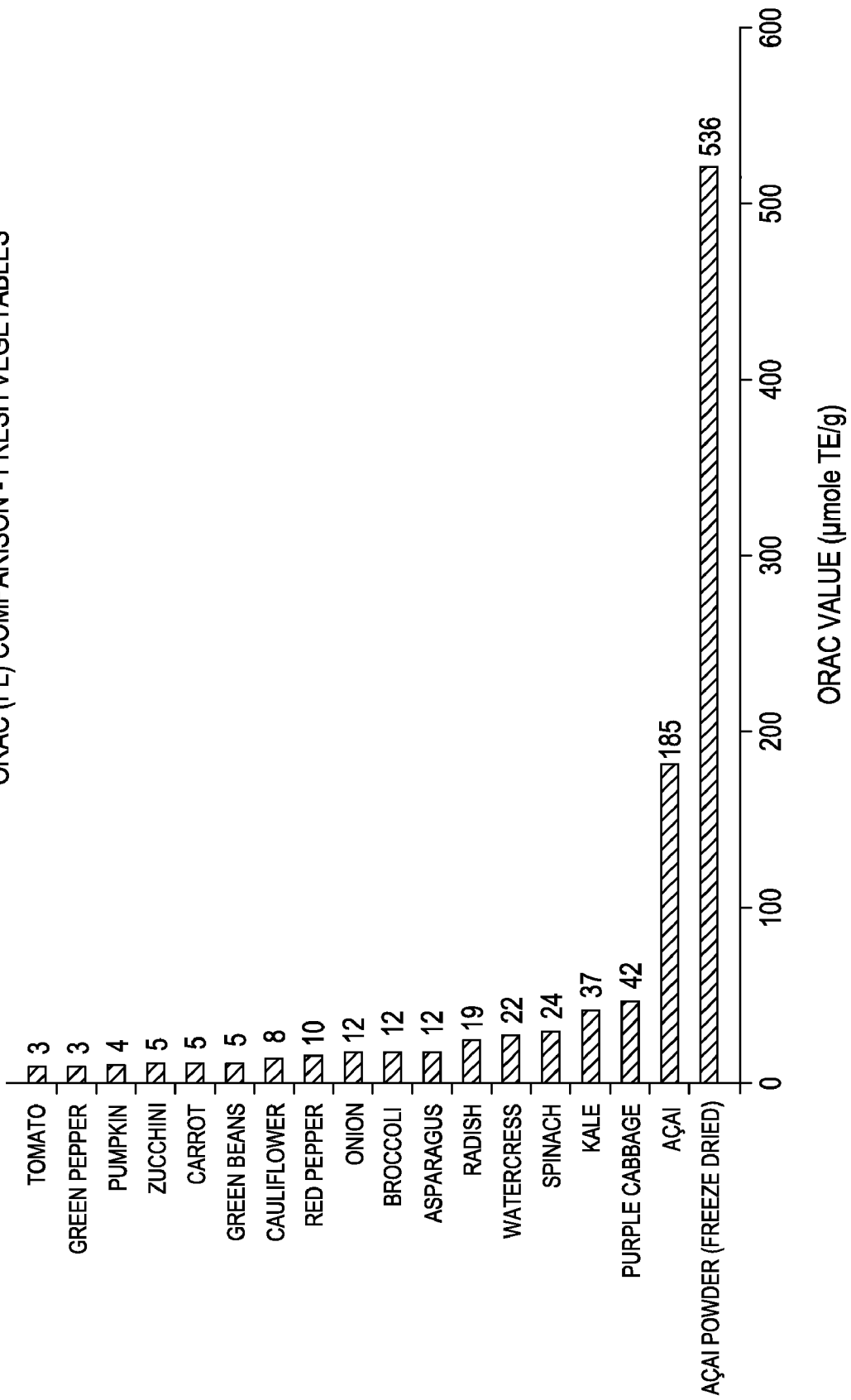
FIG. 19 is a histogram graph comparing the antioxidant activity of freeze-dried Açai powder with select fresh vegetables as determined by ORAC analysis technique.

Comparative Analysis of the Antioxidant Potential of Dehydrated Açai and Select Fresh Vegetables by $ORAC_{FL}$ Analysis The antioxidant activity of dehydrated Açai powder (Brunswick Laboratories, Wareham, Mass.) was compared with the antioxidant activity of select fresh vegetables as determined by $ORAC_{FL}$ analysis technique (as detailed above) (FIG. 19). As shown in FIG. 19, the ORAC value of freeze-dried Açai powder (536 μmole TE/g) was more than 10-fold greater than the ORAC value of purple cabbage (42 μmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 23

Comparative Analysis of the Antioxidant Potential of Dehydrated Fruits and Vegetables by $ORAC_{hydro}$ Analysis Table 22 summarizes the antioxidant activity of dehydrated fruits and vegetables (Brunswick Laboratories, Wareham, Mass.) as determined by $ORAC_{hydro}$ analysis technique (as detailed above). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

TABLE 22

| Fruits/Vegetables | $ORAC_{hydro}$ Scores |
| --- | --- |
| Beets | 120 |
| Black raspberry | 340 |
| Broccoli | 130 |
| Carrots | 50 |
| Cherries | 100 |
| Elderberry | 240 (single sample) |
| Green beans | 70 |
| Hawthorn | 130 |
| Red pepper | 90 |
| Red raspberry | 210 |
| Spinach | 150 |
| Tomato | 60 |
| Wild blueberries | 260 |
| Wolfberry | 220 (single sample) |

All values are $ORAC_{hydro}$ per gram.
All are averages of multiple samples, unless otherwise stated.

Example 24

Comparative Analysis of the Antioxidant Potential of Dehydrated Fruits and Vegetables by $ORAC_{hydro}$ Analysis Table 23 summarizes the antioxidant activity of dehydrated fruits and vegetables (Brunswick Laboratories, Wareham, Mass.) as determined by $ORAC_{hydro}$ analysis technique (as detailed above). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

TABLE 23

| Fruits/Vegetables | $ORAC_{hydro}$ Scores |
| --- | --- |
| Beets | 120 |
| Black raspberry | 340 |
| Broccoli | 130 |
| Carrots | 50 |
| Cherries | 100 |
| Cranberry | 125 |
| Elderberry | 240 (single sample) |
| Green Beans | 70 |
| Green pepper | 160 |
| Hawthorn | 130 (single sample) |
| Red pepper | 90 |
| Red raspberry | 210 |
| Spinach | 150 |
| Tomato | 60 |
| Wild blueberries | 260 |
| Wolfberry | 220 (single sample) |

All values are $ORAC_{hydro}$ per gram.
All are averages of multiple samples, unless otherwise stated.

Example 25

Figure 20:
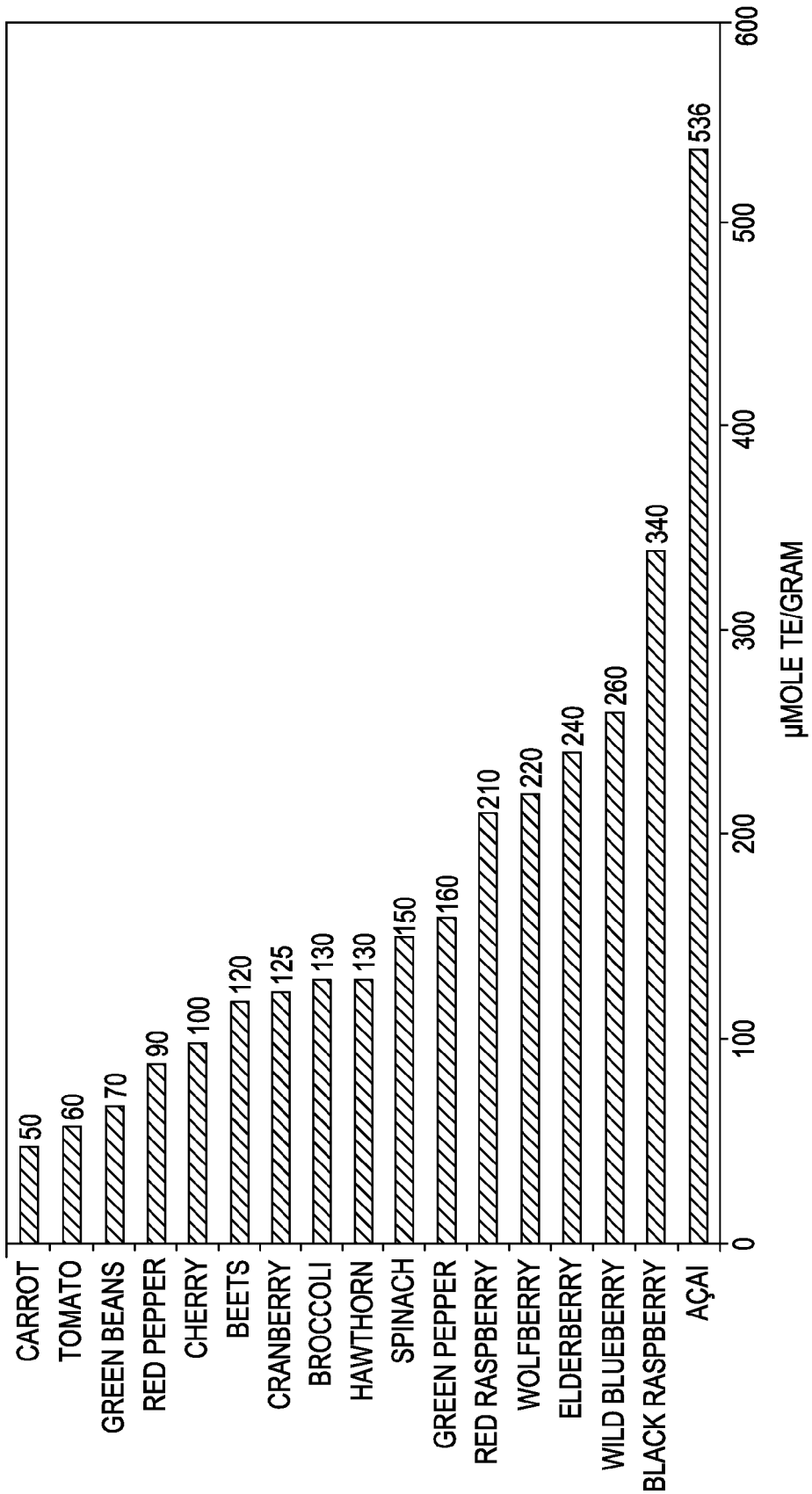
FIG. 20 is a histogram graph comparing the antioxidant activity of dehydrated Açai with select dehydrated fruits and vegetables as determined by ORAC analysis technique.

Comparative Analysis of the Antioxidant Potential of Freeze-Dried Açai and Select Dehydrated Fruits and Vegetables by $ORAC_{FL}$ Analysis The antioxidant activity of freeze dried Açai powder (231003/0410-C; Brunswick Lab ID. 03-2096; Brunswick Laboratories, Wareham, Mass.) was compared with the antioxidant activity of select dehydrated fruits and vegetables as determined by $ORAC_{FL}$ analysis technique (as detailed above) (FIG. 20). As shown in FIG. 20, the ORAC value of freeze-dried Açai powder (536 μmole TE/g) was greater than the ORAC value of dehydrated black raspberry (340 μmole TE/g). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram.

Example 26

Analysis of the Antioxidant Potential of Freeze-Dried Mai by Trans-Reveratrol Analysis The antioxidant activity of freeze dried Açai powder (231003/0410-C; Brunswick Lab ID. 03-2096; Brunswick Laboratories, Wareham, Mass.) was determined by Trans-Resveratrol analysis (as detailed below) to be 1.1 μg/g.

Samples were analyzed using an by HPLC chromatography using an HP 1100 series HPLC equipped with a Phenomenex Luna Phenyl-Hexyl (250×4.6 mM) with 2 band prefilter and autosampler/injector, binary HPLC pump, column heater, diode array detector, and fluorescence detector. The Mobile Phase A2 was DI H$_2$O: Acetonitrile: Acetic Acid (89:9:2 v/v). The Mobile Phase B2 was Acetonitrile: DI H$_2$O (80:20 v/v). All biological samples were stored in −80 degrees C. Freezer until ready to analyze. All dry and fruit samples were extracted with 20 ml of Methanol (MeOH). After extraction samples were sonicated for 1 hr. All samples were be centrifuged at 14000 rpm at 4 degrees C. for 5 min. Samples were analyzed at a flow rate of 1 ml/min with a run time of 35 min and post-run time of 10 min. Retention Time was approximately 26 min. The gradient was set as follows: 10 min at 0% B; 25 min at 40% B; 32 min at 100% B; and 35 min at 100% B. Absorption at 280 nm was monitored. Quantification of compounds by HPLC is the process of determining the unknown concentration of a compound in a known solution. It involves injecting a series of known concentrations of the standard compound solution of Resveratrol onto the HPLC for detection. The chromatograph of these known concentrations will give a series of peaks that correlate to the concentration of the compound injected.

Example 27

Analysis of Antioxidant Activities Against Hydroxyl Radical and Peroxynitrite in Jucara and Açai Preparations I. General A. Peroxynitrite Peroxynitrite is a cytotoxic product of nitric oxide (NO) and superoxide. Peroxynitrite is a far stronger oxidant and much more toxic than either nitric oxide or superoxide acting separately.

A variety of pathologies are associated with the formation of peroxynitrite, a potent oxidant formed from the reaction of NO with superoxide. This reaction is the fastest reaction NO is known to undergo, and transforms two relatively unreactive radicals into a more reactive oxidant, peroxynitrite. Peroxynitrite is invariably formed in larger amounts when more NO is produced, and/or when an elevated level of O$_2^-$ prevails.

Peroxynitrite is a potent oxidant implicated in a number of pathophysiological processes. Peroxynitrite freely travels across cellular lipid membranes. The calculated permeability coefficient for peroxynitrite compares well with water and is approximately 400 times greater than superoxide, hence is a significant biological effector molecule not only because of its reactivity but also its diffusibility. (Lee, J., Marla, S. S. Peroxynitrite rapidly permeates phospholipid membranes. Proc Natl Acad. Sci., 1997.)

In this regard, pathologies such as diabetes, atherosclerosis, and ischemia-reperfusion injury, are associated with oxidative stress characterized by an elevated level of O$_2^-$ that can lead to increased peroxynitrite formation. Recent evidence also suggests multiple sclerosis and Alzheimer's disease are associated with peroxynitrite formation. In addition, peroxynitrite has also been implicated during ischemia and reperfusion, and during sepsis and adult respiratory distress syndrome. Ischemia and reperfusion are accompanied by an increase in superoxide due to the activation of xanthine oxidase and NAPDH oxidase, respectively. Thus, peroxynitrite is likely to be implicated in a number of pathologies in which an imbalance of NO and O$_2^-$ occurs. The formation of peroxynitrite is desirable for non-specific immunity but possibly not during signaling by NO.

Peroxynitrite is formed in biology from the reaction of nitric oxide and superoxide. The enzyme Superoxide Dismutase (SOD) lowers superoxide and prevents peroxynitrite formation (see my review: Pryor, W. A. and Squadrito, G. L. (1995). Am. J. Physiol. (Lung Cell. Mol. Physiol. 12) 268, L699-L722). The chemistry of peroxynitrite: a product from the reaction of nitric oxide with superoxide). Peroxynitrite is a potent oxidant and itself can oxidize many biomolecules. Nevertheless, in biological systems, it reacts mostly with carbon dioxide to form reactive intermediates, such as ONOOCO$_2^-$, O2NOCO$_2^-$, COO$_3^-$, and NO$_2$. Of these intermediates, only COO$_3^-$ and NO$_2$ participate in bimolecular reactions with biological target molecules; the CO$_2$ adducts ONOOCO$_2^-$ and O2NOCO$_2^-$ are too short lived and decompose before they can react bimolecularly.

Oxidative stress, such as that caused by peroxynitrite is known to damage the vascular endothelium, a process that can lead to atherosclerosis (Thom, S. R. and Ischiropoulos, H. Mechanism of oxidative stress from low levels of carbon monoxide. Health Effects Institute Research Report, number 80, 1997.)

B. Hydroxyl Radical

If the function of radicals is to destroy molecules and tissues, then the hydroxyl radical would be the radical's radical. It reacts at diffusion rates with virtually any molecule found in its path including macromolecules such as DNA, membrane lipids, proteins, and carbohydrates. In terms of DNA, the hydroxyl radical can induce strand breaks as well as chemical changes in the deoxyribose and in the purine and pyrimidine bases."

"Damaged proteins, many of them crucial enzymes in neurons, lose their efficiency and cellular function wanes. Protein oxidation in many tissues, including the brain, has been proposed as an explanation for the functional deficits associated with aging.

The hydroxyl radical is a third generation species of radical which is derived from hydrogen peroxide (H$_2$O$_2$), which, in turn, is derived from the superoxide radical through the action of the enzyme superoxide dismutase.

Hydrogen peroxide is reduced to hydroxyl radicals by the enzymes glutathione peroxidase and catalase in the presence of transition metals such iron or copper.

II. Results

The antioxidant activity of freeze-dried Açai powder and freeze-dried Jucara powder (Brunswick Lab ID. Brunswick Laboratories, Wareham, Mass.) were determined by ORAC analysis technique (as detailed above) and is summarized below in Table 24.

TABLE 24

Measurement of Antioxidant Activities Against Hydroxyl Radical and Peroxynitrite

| Samples | HORAC | NORAC |
|---------|-------|-------|
| Jucara  | 85    | 134   |
| Açai    | 52    | 34    |

The HORAC result in Table 24 is expressed as micromole gallic acid equivalents per gram. The NORAC result in Table 24 is expressed as micromole Trolox equivalents per gram.

Example 28

Analysis of Superoxide Dismutase-Like Activity and Cyclooxygenase Inhibitory Activity of Açai and Jucara Preparations I. Superoxide ($O_2^-$) Scavenging Activity Assay (SOD)

A. Background

It is estimated one percent of total oxygen consumed by an adult (70 kg body mass) is converted to superoxide anion. An adult at rest utilizes 3.5 mL $O_2$/kg/min, which would result in 0.147 mole/day $O_2^-$. $O_2^-$ is believed to be cause of other reactive oxygen species such as hydrogen peroxide, peroxynitrite, and hydroxyl radicals (from hydrogen peroxide). Therefore, $O_2^-$ scavenging capacity in human body is the first defense line against oxidative stress. In fact, it is reported that over-expression of superoxide dismutase and catalase in transgenic flies extended life-span by as much as one-third, perhaps, due to decreased oxidative stress reflected by lower protein carbonyl contents. (Orr and Sohal, Science 263: 1128-1130, 1994. Superoxide scavenging capacity in blood is a very important parameter for one's antioxidant status. This assay is designed for accurately quantify this parameter in a high throughput fashion.

B. Experimental Procedure

Instruments

Precision 2000 eight channel liquid handling system and Synergy HT microplate UV-VWAS and fluorescence reader both from Bio-tek Inc. (Winooski, Vt.).

Reagents

Hydroethidine was from Polysciences, Inc. (Warrington, Pa.). Xanthine oxidase (from buttermilk, Catalog number X4875), xanthine, superoxide dismutase (from bovine erythrocytes, catalog number S 2515) were purchased from Sigma-Aldrich (St. Louis, Mo.).

i. Reagent Preparation

Buffer. The buffer consists of 75 mM phosphate buffer (pH 7.4) containing 100 μM diethylenetriamine pentaacetic acid (DTPA). To prepare the buffer, 0.0393 g of diethylenetriamine (DTPA) was weighed out and 10 mLs of ORAC buffer working solution was added. This yielded 10 mLs of 10 mM DTPA stock solution. Next, to 198 mLs of ORAC buffer working solution was added 2 mLs of DTPA stock solution. This yielded 200 mLs of 100 μM $O_2^-$ buffer working solution with DTPA.

Xanthine oxidase. The xanthine oxidase suspension (in refrigerator) from Sigma was diluted 20 times by buffer to give a homogeneous solution. Take 19 mLs of $O_2^-$ buffer and add 1.0 mL of Xanthine oxidase suspension. This yielded 20 ml of Xanthine oxidase working solution, which was made fresh daily.

Xanthine solution. Xanthine (15 mg) was weighed and place in a clear glass bottle. 5 mLs of 0.1 N sodium hydroxide (0.1 N NaOH) was added and the solution was vortexed and sonicated until the solid was dissolved. 95 mLs of $O_2^-$ buffer was added and vortexed. This yielded 100 mLs of Xanthine solution. The solution was kept at room temperature to avoid precipitation of xanthine. The Xanthine solution was made fresh daily.

Hydroethidine (HE) Working Solution. Stock solution of dihydroethidium—0.04 g of dihydroethidium was added to 20 mL of acetonitrile. This yielded 20 mLs of HE stock solution (2 mg/mL), which was stored in small aliquot vials at −80 degrees C. Next, 0.125 mL of dihydroethidium (HE) stock solution was added to 24.875 mLs of xanthine solution. The solution was sonicated and heated until clear. This yielded 25 mLs of Hydroethidine (HE) working solution, which was prepared fresh daily.

Superoxide Dismutase Working Solution (SOD). Thirty thousand units of SOD (Sigma) was reconstituted in ten mL buffer solution. The solution was divided into small aliquots (0.4 mL per vial, stock solution) and kept at −20 degrees C. This yielded 3000 units, which was diluted to 30 units for use (see below). 200 μL of SOD 3000 unit stock solution was added to 19.8 mLs of $O_2^-$ buffer to yield 20 mLs of SOD 30 unit working solution.

Control. The stock solution was Manganese (III) 5, 10, 15, 20 tetrachloride stock solution 1144 μM which was stored at −80 degrees C. To prepare the working solution, the stock solution was diluted 100-fold with $O_2^-$ buffer and vortexed. By taking 9.9 mLs of $O_2^-$ buffer and adding 100 μL of Manganese stock solution, 10 mL of 11.44 μM Manganese working solution, which was placed in wells G1 and G12 as controls.

Assay Procedures

The assay was carried out on a Precision 2000 liquid handling system with a 96-well microplate using the following protocol:

In plate one (polypropylene) 200 μL of samples were added to wells B1, C1. E1, F1, and B12, C12, E12, F12.

200 μL, of SOD working solution was added to D1 and D12 wells.

200 μL of O2—buffer was added to A1, H1, A12, and H12 wells.

200 μL of Manganese working solution was added to G1 and G12.

The reagents were loaded into the cups on rack B of the precision 2000 as follows:

20 mLs of O2-Buffer in B1
20 mLs of HE in B2
20 mLs of Xanthine oxidase in B4

A ×2 dilution (ORAC ×2) was carried out on a Precision 2000. A dilution was carried out so that all the samples, standard, and blank were diluted by 2, 4, 8, 16, and 32 times.

25 μL of the solutions in each well were transferred to a reaction plate (polystyrene, 320 μL) followed by the addition of 150 μL HE working solution.

Incubate reading plate for 20 min at 37 degrees C.

After incubation, add Xanthine oxidase by running AAPH addition (B4) program. This allows 25 μL Xanthine oxidase working solution to be added to all wells in plate #2.

After xanthine oxidase was added, place plate in platereader.

The plate and the fluorescence was read every minute for ten minutes with excitation filter at 485±25 nm and emission filter at 590±30 nm the readings were referenced to low well of D1 arbitrarily set at 5000 units. Plate two layout (polystyrene) each well contains 150 μL HE working solution, 25 μL sample, and 25 μL xanthine oxidase (added after 30 min. preheat)

C. Data Processing

From the raw data, a linear curve was obtained and the slopes of the curves were calculated by the KC-4 program used to control the plate reader. The slopes were exported and further calculations were executed by Microsoft Excel software.

Simplified Chemical Kinetics $O_2^-$ was generated constantly by the following reaction catalyzed by xanthine oxidase. The rate of superoxide production was constant and pseudo-zero order to xanthine, which was in large excess in comparison with xanthine oxidase.

$$\text{xanthine} + O_2 \rightarrow \text{uric acid} + O_2^- \quad (1)$$

The superoxide formed was either reacted with HE or scavenged by superoxide dismutase.

$$HE + O_2^- \rightarrow \text{Oxidized } HE \quad (2)$$

$$2O_2^- + O_2 + H_2O_2 \quad (3)$$

$$O_2^- + \text{Sample} + P \quad (4)$$

Assuming steady state concentration of $O_2^-$, the fluorescence increase rates in the absence (Vo) and presence (V) of $O_2^-$ scavenger (SOD) have the following relationship:

$$V_o/V = 1 + k_3[SOD]/(k_2 \cdot [HE]) \quad (5)$$

The plot of $V_o/V$ vs [SOD] will give a linear curve with interception at (0, 1) and slope $k_3/k_2$ [HE]. For an unknown sample the ratio between the slopes of the unknown and the standard was:

$$\{k_3/k_2[HE]\}/\{k/k_s/k_2[HE]\} = k_3/k_s \quad (6)$$

Equation (5) would give relative SOD activity of a sample with unit of measure of SOD unit equivalent per gram or per liter of the sample depending on the concentrations used in plotting a sample's $V_o/V$ vs concentration curve.

II. Cyclooxygenase Assays

A. Introduction

Inflammation is the response of our immune system to the intrusions by pathogens such as viruses and germs, as well as by chemical or physical insults. Painful sometimes, inflammation is normally healing response. But in some instances inflammation proceeds to a chronic state, associated with debilitating disease such as arthritis, multiple sclerosis, or even cancer. Research on experimental and system biology has shed light on the complex inflammation processes. One way, among several others, to keep inflammation in check is to inhibit the activity of cyclooxygenase-2 (COX-2) which is directly associated with inflammation. It is also found that the non-steroid anti-inflammatory drugs (NSAIDs) are excellent COX inhibitors. The beneficial actions of NSAIDs can be associated with inhibition of COX-2 whereas their harmful side effects (the most common one is gastrointestinal toxicity) are associated with inhibition of COX-1. These synthetic COX inhibitors include aspirin, ibuprofen, nap oxen, and celecoxib (Celebrex™). More research efforts have been discovering more selective and active COX-2 inhibitors as new generation of NSAIDs.

Historically, herbal remedies for inflammation have been practiced for thousands of years. In fact, Celsus defined around AD 40 as 'rubor, calor, dolor, tumor' (redness, heat, pain and swelling) is, today, the inflammation symptoms. Only recently is the action mechanism for the botanical extracts investigated at the molecular biology level using COX-1 and COX-2 inhibitory assay as a guide for isolation of effective components from herbal mixtures. This approach also permits a better evaluation and optimization of the effectiveness of the pain-relieving and anti-inflammatory herbal supplements in the nutraceutical industry. To fulfill the industrial need for measuring COX inhibition capacity of samples of botanical origin, an in vitro COX-1 and COX-2 inhibitor-screening assay was adopted, with modifications that improve the efficiency and reduce cost. Described herein are the details of COX-1 and COX-2 inhibitory activity assay that is applicable to botanical products.

B Assay Principle

COX-1 and COX-2 both catalyze the oxygenation of arachidonic acid to form prostaglandins (FIG. 1). The enzyme activity can be measured by the oxygen consumption rates. In fact, unit activity of enzyme is defined as "One unit of enzyme consumes one nmol of oxygen per minute at 37 degrees C. in 0.1 M tris-HCl buffer pH 8.0, containing 100 mM arachidonic acid, 5 mM EDTA, 2 mM phenol, and 1 mM hematin". The oxygen concentration is monitored in real time by an Oxytherm (FIG. 2), an oxygen concentration measurement system, purchased from Hansatech. The initial oxygen consumption rate is obtained from the kinetic curve. In the presence of inhibitors, the initial rate decreases. $IC_{50}$, the concentration at which the initial oxygen consumption rate decreases by 50%, is used to express the COX-1 and 2 inhibition activity. The selectivity is expressed as the ratios of $IC_{50}$ for COX-1 and COX-2. Samples are normally dissolved in dimethyl sulfoxide (DMSO), ethanol, or water.

C. Experimental Details (1) Assay Conditions:

Instrument: Oxytherm

Buffer 0.1 M Tris-HCl, pH 8.0, with 5 mM EDTA, 2 mM phenol, and 1 mM heme

Temperature: 37 degrees C.

Initial [O2]: 212 mM

Enzyme volume: 5 mL (or ~100 units)

Total volume: 0.5 mL

Sample volume: 5 mL

Substrate: 5 μL arachidonic acid (Conc. 10 mM in 0.01 M NaOH solution)

Heme: 5 mL (final conc. 1 mM)

Data recording speed: 5 readings per second (2) Experimental Procedures:

Half mL of Tris buffer (incubated at 37 degrees C. oven) was added to the reaction chamber followed by 5 mL 100 mM heme in DMSO. To the solution, 5 mL COX-1 (or 10 mL COX-2) enzyme solution were added (used as received from supplier). The mixture was incubated for one minute. Five mL sample (in DMSO or ethanol) was added and incubated for one minute. Five mL arachidonic acid was added and the reaction rate monitored. The initial rate was obtained from the slope of the kinetic curves.

Sample extraction and dissolution: Solid samples were extracted using dimethyl sulfoxide (DMSO), ethanol, 50% acetone in water, or water depending on their solubility. Water-based liquid samples were tested directly or diluted with water when necessary. Oil based samples were dissolved in DMSO or ethanol for analysis.

Quality Control:

In order to ensure validity of the data and the normal performance of the oxytherm system, several quality control measures were applied.

(1) The known COX-1 and 2 inhibitor indomethacin was used as a quality control sample. Indomethacin has IC50 of 0.1 mM for COX-1 and 6.0 mM for COX-2. The IC50 of the indomethacin was measured for each lot of enzyme. The properly working oxytherm system should give IC50 of indomethacin within 20% of the normal value for both enzymes.

(2) Each sample solution is tested in duplicate or triplet to obtain an averaged ICW value.

(3) One blank (100% activity) was run in between every five sample solutions to further ensure the reproducibility.

$IC_{50}$: The concentration of a sample when 50% of the enzyme activity is inhibited. Lower $IC_{50}$ means higher activity. $IC_{50}$ Ratio: This number indicates the selectivity of the sample in inhibition of COX enzymes. When the ratio is one, there is no selectivity. If the ratio is smaller than one, the sample inhibits COX-1 better than COX-2. If the ratio is larger than one, the sample inhibits COX-2 better. Standard deviation is about 20%.

D. References
1. Nathan, Nature 2002, 420: 846-52.
2. Tracey, Nature 2002, 420: 853-59.
3. Couzer and Marnett, Chemical Rev. 2003, ASAP.
4. Wu et al., J. Agri. Food Chem., 2002, 50: 701-05.
5. Smith and Marnett, Biochem, Biophys. Acta 1991, 1083, 1-17.
6. Johnson et al., Arch. Biochem. Biophys. 1995, 324: 26-34.
7. Kulmacz and Lands W. E. M. Requirements for hydroperoxide by the cyclooxygenase and peroxidase activities of prostaglandin H synthase. Prostaglandins 1983, 25, 531-40.

III. The Superoxide Anion Scavenging Potential of Açai and Freeze-Dried Jucara Powders The superoxide anion scavenging potential of freeze-dried Açai powder and freeze-dried Jucara powder were measured as detailed above (Brunswick Lab ID. Brunswick Laboratories, Wareham, Mass.). The most studied superoxide dismutase (SOD) from a natural source is wheat sprout SOD. The SOD activity for wheat sprout is 160 to 500 unit per gram basis. By comparison, the freeze-dried Açai and freeze-dried Jucara powders were substantially high in superoxide scavenging capability as summarized below in Table 25.

TABLE 25

| Sample | SOD (unit/g)* | COX Inhibition (mg/g)** |
|---|---|---|
| Açai | 1,614 | 19 |
| Jucara | 6,657 | 60 |

*Result is expressed as SOD unit equivalent per gram
**Result is expressed as Aspirin mg equivalent per gram Cyclooxygenase (COX) activity (COX Type 1, i.e., COX I; and COX Type 2, i.e., COX II) was measured in the presence and absence of freeze-dried Açai powder and freeze-dried Jucara powder (Brunswick Lab ID. Brunswick Laboratories, Wareham, Mass.) as detailed above. As summarized in Table 25 (above) and Table 26 (below), freeze-dried Açai powder and freeze-dried Jucara powder inhibited COX enzyme. As shown in Table 26, freeze-dried Açai powder and freeze-dried Jucara powder inhibited both the COX I and COX II isozymes. Freeze-dried Açai powder and freeze-dried Jucara powder, therefore, are effective in the prevention and treatment of inflammatory diseases associated with COX I and COX II activity, e.g., arthritis.

TABLE 26

| Sample | COX I (mg/mL) | COX II (mg/mL) |
|---|---|---|
| Açai | 6.96 | 12.50 |
| Jucara | 2.20 | 10.92 |

*Results are expressed as $IC_{50}$ (50% Enzyme Activity Inhibition Concentration)

Example 29

Figure 21:
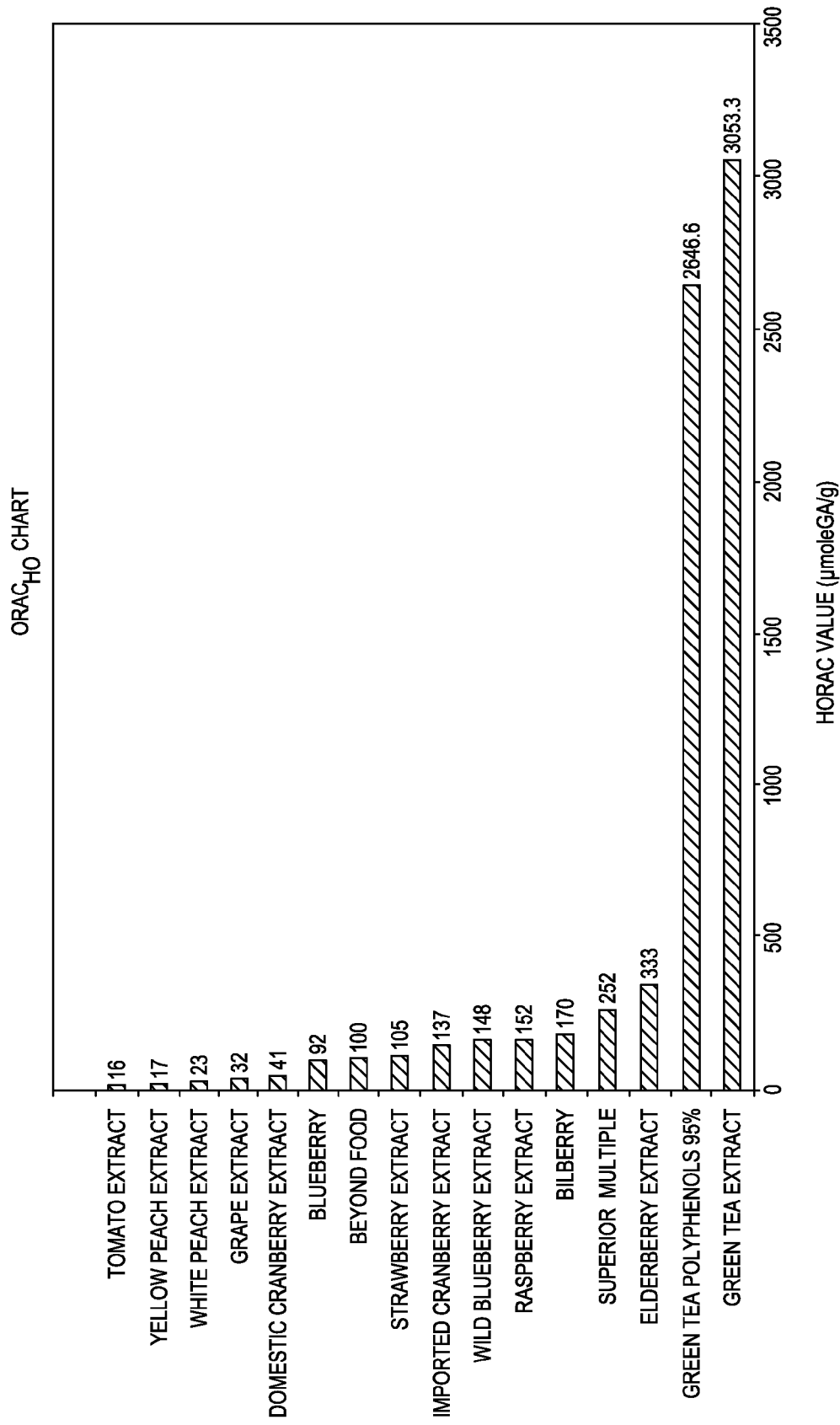
FIG. 21 is a histogram graph comparing the antioxidant activity of fruits and vegetables by $ORAC_{HO}$ analysis technique.

Comparative Analysis of the Antioxidant Potential of Fruits and Vegetables by $ORAC_{HO}$ Analysis FIG. 21 shows the antioxidant activity of fruits and vegetables as determined by ORAC analysis technique (Brunswick Laboratories, Wareham, Mass.; as detailed above). The $ORAC_{FL}$ analysis, utilizing fluorescein as the fluorescent probe, provided a measure of the scavenging capacity of antioxidants against the peroxyl radical, which is one of the most common reactive oxygen species (ROS) found in the body. $ORAC_{hydro}$ reflects water-soluble antioxidant capacity. Trolox, a water-soluble Vitamin E analog, was used as the calibration standard and the ORAC result is expressed as micromole Trolox equivalent (TE) per gram. The HORAC results in FIG. 21 are expressed as micromole gallic acid equivalents per gram.

Example 30

Preparation of Açai Juice

Figure 22:
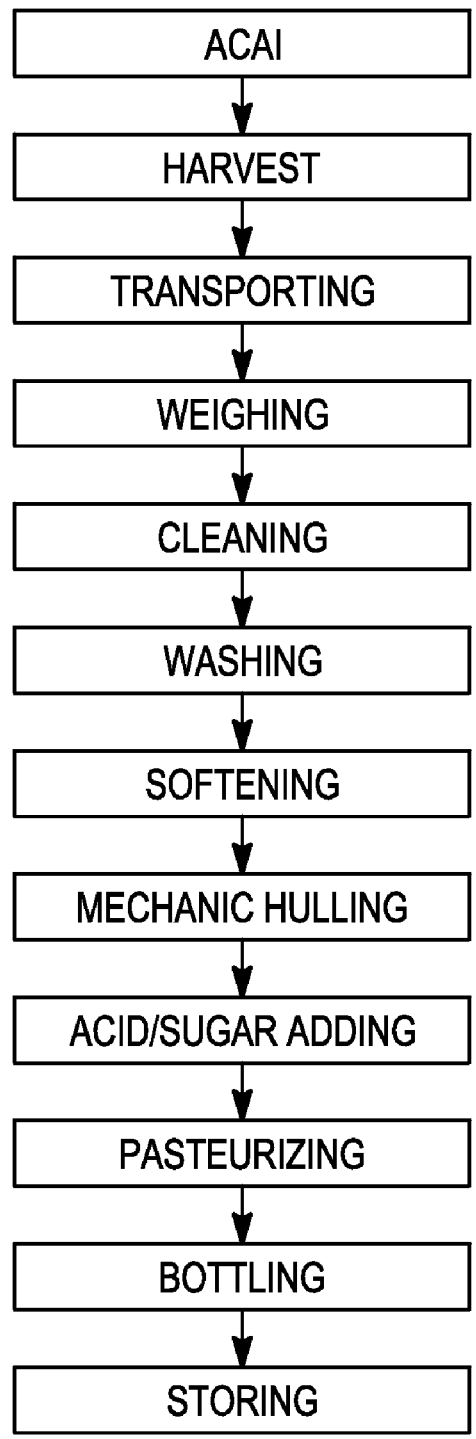
FIG. 22 is a flow chart schematic diagram detailing Açai fruit juice preparation.

FIG. 22 is a flow chart detailing Açai juice preparation, including washing of the fruits and their pasteurization. A better conservation of the fruit and of the juice will allow consumption of the food while preserving its nutritional value and will ease the organization of its commercialization, between harvests. The preparation and processing steps of the Açai juice are shown in FIG. 22.

The hulling of the fruit can be done in several different ways and the softening conditions change from one producer to the other.

I. Optimization of the Pulp Extraction Process—Softening and Mechanical Hulling

Fruit hulling can be performed in several ways, each producer has its own way for processing the Açai (softening time and temperature, amount of water per kg of fruits, time that the fruit stays in the machine). It was necessary to optimize and systematize the pulp extraction process in order to maintain reproducibility among our experiences and to assure a good output.

Figure 23:
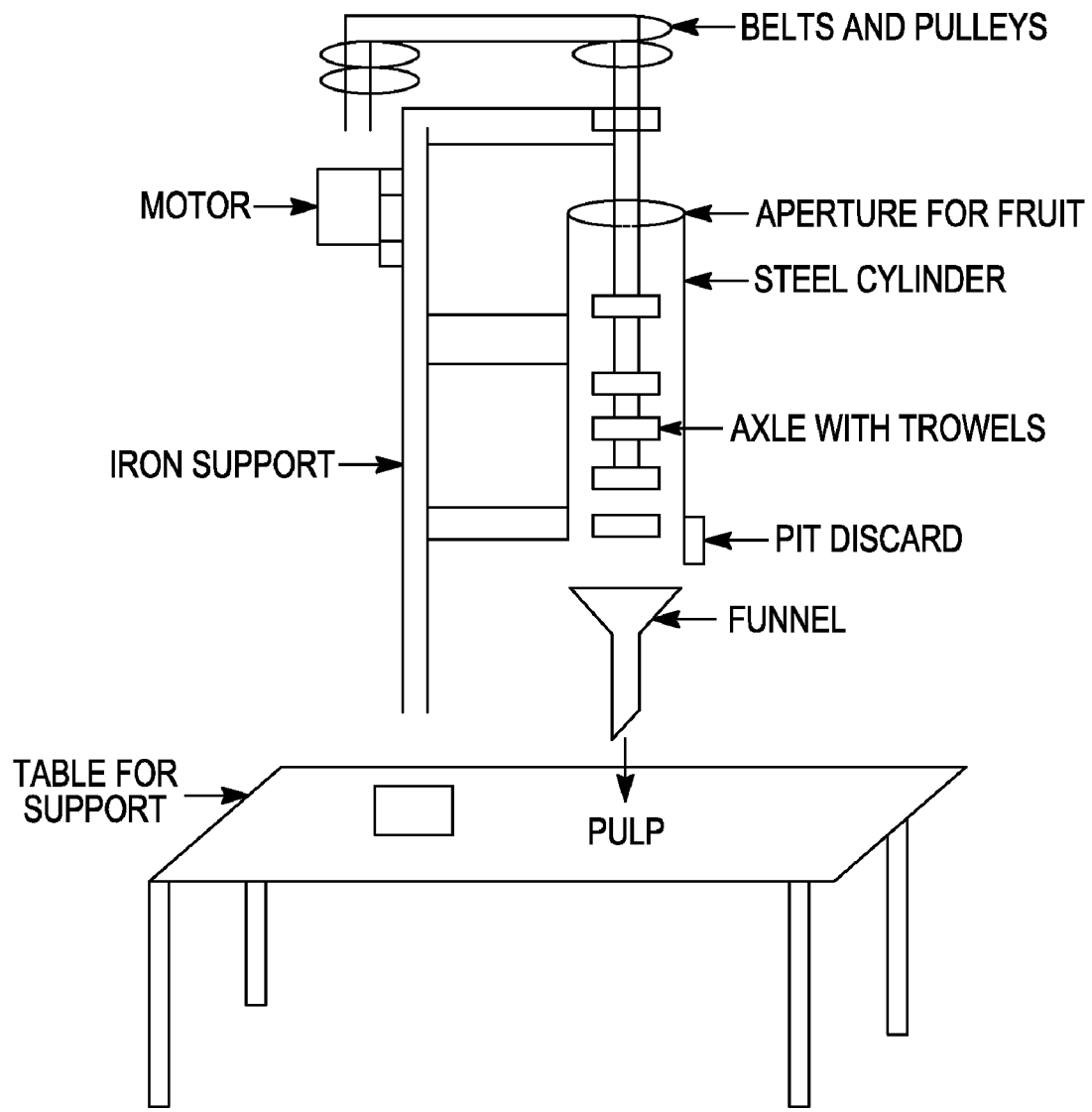
FIG. 23 is a schematic diagram of the hulling apparatus used in Açai fruit juice preparation.

The Açai fruit hulling takes place, most of the time, in a mechanical hulling with vertical axis, specifically elaborated and used for the Açai fruit. A picture of a representative mechanical hulling machine is shown in FIG. 23. It was designed for processing 2 kg of Açai each time, in order to minimize the amount of fruits in each processing.

The time and temperature of water for soaking the fruit varies from one fair-trader to the other. The fruit can be soaked in running water at room temperature for some hours before beating or it can be softened in warm water for a short time (10-20 minutes).

In the laboratory, several softening times (0, 5, 10, 15, 20, 30 minutes) and soaking water temperatures were tested (30, 40, 45, 50 and 60 degrees C.). Although the results suggested that there were no significant differences between the different conditions of softening, a greater output was observed when the Açai was softened in water at 45 degrees C. for 20 minutes.

The hulling total time, as well as the amount of water and the way it was used during this time, constitute very important variables to the output and density of the juice. Five total times of hulling were tested (altering from 2:30 to 5:00) and for each one, several hulling times were tested before putting the first dose of water, and several ways for putting the water inside the bulling machine (the time for the dripping of the juice at the end of the huffing was set to 45 seconds). The total amount of water was 1 liter per 2 Kg of fruits (in order to get an ideal juice; not very strong, not very weak).

From these studies, it was noticed that the total time for hulling and the way of putting water inside the hulling machine have a very significant effect on the outputs in dry substances. From those experiences, the following protocol for the preparation of the juice was set:

1. Weigh 2 kg of raw material (Açai).
2. Prepare 5 containers with 200 mL of water each.
3. Place the Açai in the machine, turning it on at time 0.
4. After one minute of hulling, put the first 200 mL water container at once.
5. After 1 min 30 s; 2 min; 2 min 30 s; and 3 min, add one of each of the remaining four containers.
6. Leave it dripping for 45 seconds up to 3 min 45 sec.

The recycling impact of part of the juice was analyzed. Although this technique for preparing the juice is very popular, no differences in the outputs of dry substances were noticed.

Ii. Evolution of the Microbiological Characteristics of Açai Fruit After its Harvest When Açai characteristics and qualities are compared at harvest and at middle harvest, significant changes were noticed in the organoleptic qualities and in the numbers of the scientific indicators (microbiological, thy weight, color). For example, the Açai of the harvest sold in Beim, is cheap and abundant. It has good quality, because as it comes from places near Beim, and it doesn't suffer changes during transportation. On the other hand, between harvests, Açai is produced at lower quantities and its organoleptic characteristics are inferior to those of the Açai from harvest time and it is more expensive. The Açai produced between harvests comes from more distant places (Maranho, Maraj island), and undergoes a long trip before reaching Beim's harbor. Time between harvest and sale/consumption of fruit is very important (48 hours is pretty much the maximum time the fruit lasts after harvest at room temperature).

An increase in microbial load was noticed in the Açai purchased between harvests when compared to that from harvest time. During harvest time, the average load of microorganism per gram in fresh Açai was $10^6$ microorganisms per gram of dry pulp—what accounts for 10 ml of juice. Between harvests, the average load of microorganism per gram increased to $10^9$, indicating a microbial load 1000 times higher). Accordingly, it was necessary to determine if the contamination increase was caused mainly because of low quality of the palms of those regions, poor transport conditions, or because of the increase in the time after harvest, leading to natural growth of the microorganisms already present at the fruit surface. Influence of time spent between harvest and processing was studied and then related to the increase in the microbial load.

Microbial load was measured at several time intervals during a 30-hour period in fresh fruits (taken 10 hours after harvest). Results indicate that there was a measurable and regular increase in the original microbial load of the fruit. The microbial load is about $10^5$-$10^6$ microorganism (bacteria, mold and leavens) per gram of dry pulp right after harvest and after 40 hours reaches a maximum value, a little superior to $10^9$ microorganism per gram of dry pulp. Since the microbial load observed 40 hours after harvest was very similar to that of the middle harvest, it is possible to conclude that the microbial load variation in the harvest time and out of harvest is mainly caused by natural increase of microorganism on the surface of the fruit rather than the low quality of the palms in those regions.

Therefore, Açai should be used right after its harvest, before the significant increase of microbial load, to avoid an alteration to the product quality (not only a natural change caused by the microorganism increase but also a change caused by necessity of using thermal radical treatment in order to preserve the product). However, methods are reducing the microbial load were assessed below.

III. Cleaning

The efficiency of cleaning methods on the decrease of microbial load of juice was studied. The studies were made using the middle harvest Açai, which means Açai that has an important level of contamination. The cleaning of the fruit with hygienic water at 0.1% (v/v) concentration, before processing, allowed the microbial load to be reduced 2 to 400 times (concerning the Açai cleaned with potable water without addition of chemical substances).

IV. Washing

The washing process is considered the primary step in the processing of the Açai juice, because it reduces the microbial load before processing the Açai, without altering its texture significantly. In the case of the Açai fruit, washing prior to processing steps has been described as helping to preserve the quality and integrity of the juice and, therefore, preserve the organoleptic, texture and nutritional qualities of the Açai juice. (Tournas, 1994).

Washing consists of placing the fruits in hot or boiling water or steaming for some time before processing (Cruess, 1995). The choice of treatment, aimed at decreasing the contaminating agents present on the surface of the fruit, is explained by the physical structure of the fruit. The fruit that has only one small layer of superficial pulp, a short contact time between the pulp and the hot water or steam leads to a positive efficiency of the treatment at not very high temperature or long time.

Studies have been conducted not only with Açai from harvest time but also Açai from middle harvest, trying at several different temperatures (from 75 degrees C. to 100 degrees C.) and several washing times (from 5 sec to 10 min). (Rogez et al., 1996). The treatments had a significant impact over the reduction of the microbial load (bacteria, mold, and leaven). However, the washing conditions were not effective for the inactivation of peroxidases, as these enzymes are more thermally resistant. Only the higher temperatures for the longer periods of wash times were able to partially reduce the activity of peroxidases (up to 20%). But harsher treatments (i.e., temperatures over 80 degrees C. with times longer than 10 seconds) caused a separation of the fatty substances of the juice (yellowish oil) seen on the surface of the juice. This texture alteration reduced the acceptability of the product by consumer, because of its appearance.

As the losses in the organoleptic characteristics are much higher with more radical washing, without being able to further reduce the microbial load, the temperature of 80 degrees C. and the time of 10 seconds were selected as the better washing conditions for the Açai fruit.

Example 31

Methods of Açai Beverage Preparation and Standards for Preparation

I. Mixing Instructions

Açai 14:1 dehydrate requires 13 parts water/liquid to 1 part dehydrate by weight. The variety of possible beverages using Açai is almost unlimited. Three examples are provided below:

Mixture 1: Twenty-five grams of Açai powder was added to 325 ml cold water. The mixture was blended at medium speed for at least 30 seconds to hydrate the powder adequately. If the mix can stand for a minute or so it will improves the texture.

Mixture 2: Twenty-five grams of Açai powder was added to 200 ml water and 125 grams of ice; blend 30 seconds. The mixture was allowed to stand one minute.

Mixture 3: Using 125 ml of milk or cream instead of ice makes a delicious smoothie.

Because Açai is low in sugar and vitamin C there is very little to prevent oxidation/fermentation. The presence of both sugar and Vitamin C is recommended. The taste of pure Açai is rather bland and the color is a very dark maroon. The addition of 1-2 tablespoons of sugar or other sweetener compliments the flavor very nicely. The color can be made redder through addition of Vitamin C (an acid). The addition of red food color will also create a more appetizing or appealing appearance. Furthermore, the addition of a banana to the mixture, as well as a sprinkling of granola arid garnishment of fruit, can also provide creative alternatives for the preparation of Açai beverages.

II. Equipment:

Blender; Gram Scale; Milliliter measuring device

III. Identity and Quality Standards for Açai Pulp

1. Goal

Present regulation aims at the establishment of minimum identity and quality standards that should be fit by Açai integral pulp and Açai, to be used as beverage. This regulation does not apply to Açai pulp for any other use.

2. Definition

Açai integral pulp and Açai are products extracted from the eatable part of the fruit of the Açai tree (*Euterpe oleracea*, Mart.) after being softened by adequate technological method.

3. Classification

The product will be classified accordingly to the amount of water/liquid added to the pulp, as follows:

3.1 Açai integral pulp is the pulp extracted from Açai without the addition of water, by mechanical methods, and without filtration. It may be submitted to a physical conservation process.

3.2 Thick or special Açai (type A) is the pulp extracted with the addition of water, presenting more than 14% of total solids and a very dense appearance.

3.3 Medium or regular Açai (type B) is the pulp extracted with the addition of water, presenting more than 11% and up to 14% of total solids and a dense appearance.

3.4 Thin or popular Açai (type C) is the pulp extracted with the addition of water, presenting more than 8% and up to 11% of total solids and not a dense appearance.

4. Basic Ingredients

The Açai integral pulp and the Açai are obtained from fresh, ripe and healthy fruits, according to specifications described above, and without any dust, parasites or microorganisms that can make the product inappropriate to consumption.

5. Optional Ingredients 5.1 Water

The water used to the pulp extraction must be potable.

5.2 Acidulante

In the case of pasteurized Açai maintained at room temperature, citric acid may be added according to the 'Good Manufacture Practices' (GMP) regulations.

6. Composition 6.1 The Açai integral pulp and the Açai must have its composition according to the fruit characteristics, with no alterations, mixtures with other species fruits or any illegal practice.

6.2 The Açai integral pulp must fit the following physical, chemical and organoleptic characteristics:

6.2.1 Physical and Chemical

TABLE 27

|  | Minimum | Maximum |
| --- | --- | --- |
| Total solids (g/100 g.) | 40.0 | 60.0 |
| Proteins (g/100 g) | 5.0 | — |
| Total lipids (g/100 gms) | 20.0 | — |
| Total carbohydrates (g/100 gms) | 51.0 | — |

Obs: gms = grams of dried material (total solids)

6.2.2 Organoleptical

Physical aspect: Pasty, presenting dark points prominent from the skin that involves the fruit.

Color: Violet purple proper for the purple Açai pulp and light green for the green Açai pulp.

Smell: Characteristic (see below).

6.3 The Açai (special, regular or popular) must fit the following physical, chemical and organoleptic characteristics:

6.3.1—Physical and Chemical

TABLE 28

|  | Minimum | Maximum |
| --- | --- | --- |
| pH (g/100 g.) | 4.00 | 6.20 |
| Total acidity, in citric acid (g/100 g) | — | 0.27 (popular) |
|  |  | 0.35 (regular) |
|  |  | 0.45 (special) |
| Total lipids | 20.0 | 60.00 |
| Proteins (g/100 gms) | 8.0 | — |
| Total sugars (g/100 gms) | — | 40.0 |

Obs: gms = grams of dried material (total solids)

6.3.2 Organoleptical

Physical aspect: The emulsion must stay stable even if heated up to 80 degrees C.

Color: Violet purple proper for the purple Açai pulp and light green for the green Açai pulp.

Smell: Characteristic (see below).

6.4 The integral Açai pulp and the Açai may contain non-edible parts of the fruit into the limits that doesn't change the quality arid organoleptical characteristics of the product. The integral Açai pulp and the Açai must fit all other physical, chemical, microscopical, microbiological, and Organoleptic characteristics fixed in the Identity and Quality Standards for general fruit pulp.

6.5 The maximum limit for the sum of moulds and leavens in the Açai integral pulp and in Açai is $5 \times 10^3$.

7 Additives

The integral Açai pulp and the Açai directed for direct consume in maximum 1 kg. pack must be maintained through physical process, forbidden the use of chemical conservants or coloring substances, except the coloring obtained from the Açai fruit.

Example 32

Preparation of Freeze-Dried Mai

Figure 24:
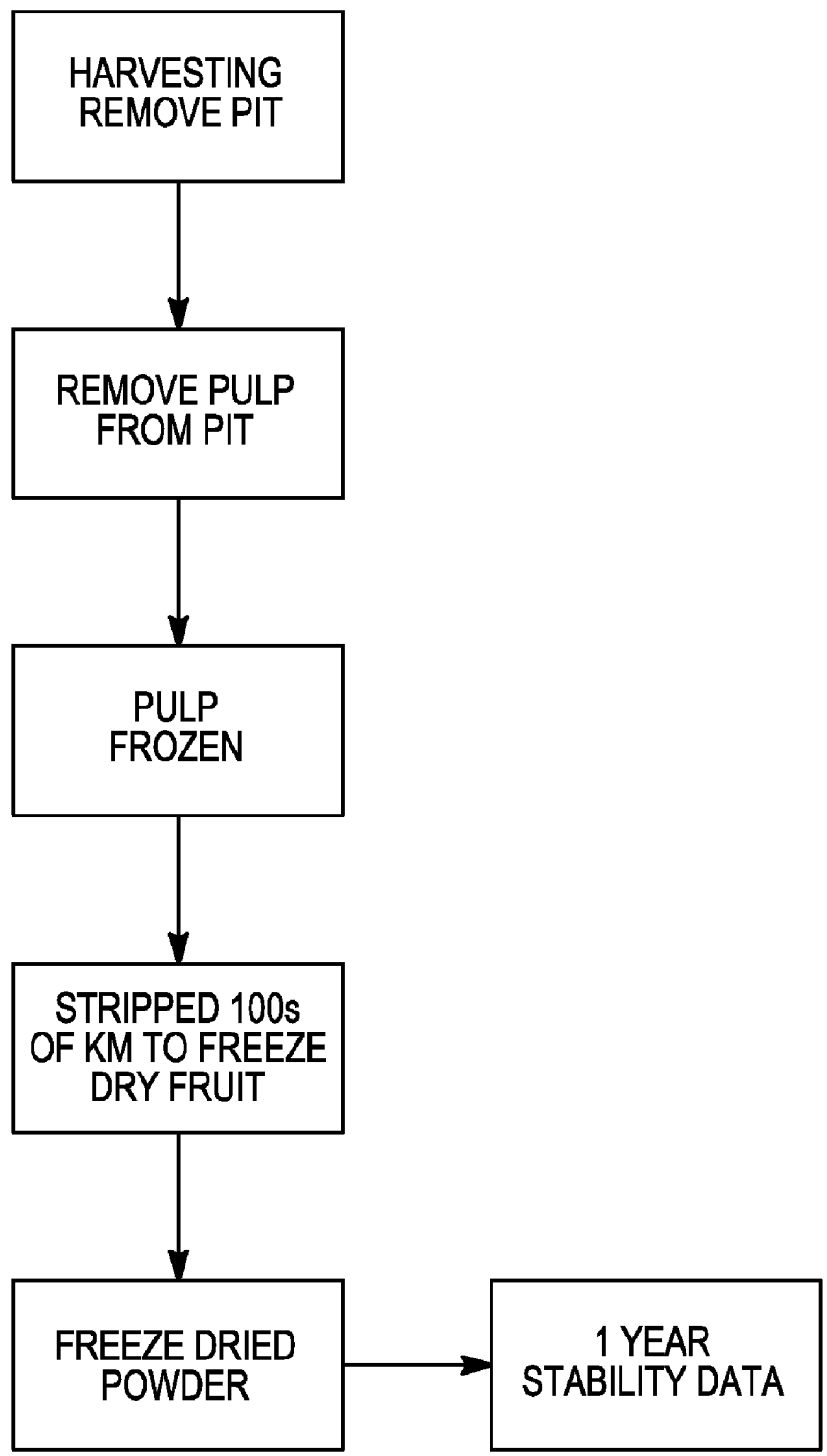
FIG. 24 is a flow chart schematic diagram detailing a method of preparing freeze-dried Açai powder.

A method of preparing freeze-dried Açai powder is detailed in FIG. 24. As shown, Açai fruit were harvested and the pit was removed. The pulp was then removed and frozen. Pulp from many Açai fruit was freeze-dried to yield a freeze-dried powder. The freeze-dried Açai powder was stable compared with unprocessed preparations of the Açai fruit pulp, which rapidly degraded within hours, rendering them unpalatable. The addition of citric acid to the Açai fruit pulp during processing and prior to freezing was useful in further stabilizing the fruit pulp preparation. Citric acid can be used to stabilize other fruit pulp preparations, e.g., Jucara, processed by the methods of the present disclosure.

Açai production is a particularly unforgiving sequence of events due to enzymes and a proportionally high load of fermenting agents on the fruit skin compared to the quantity of pulp removed from the fruit. For this reason, Açai production was traditionally limited to local and immediate consumption. Açai frozen fruit pulp must be maintained at a temperature of −5 degrees C. or less. At higher temperatures, the enzymes and fermenting agents become active and change the characteristics of the fruit pulp. One effect is the creation of insoluble compounds, the grit mentioned above, which is evident with this last batch. These insolubles were encountered in the first batches of Açai dehydrate (from two processors) and were found to be caused by the thawing of the pulp during preparation for dehydrating. This problem was resolved by not allowing the frozen Açai fruit pulp to pre-thaw prior to dehydration via freeze-drying. That is, once the Açai fruit pulp is frozen, it cannot be allowed to thaw to a temperature greater than about −5 degrees C. prior to dehydration by freeze-drying. Açai fruit pulp prepared without pre-thawing before dehydrating yielded a granular, freeze-dried Açai powder that re-hydrated very successfully and retained quality color, texture and flavor. Therefore, the present disclosure provides for a method of preparing a fruit-based dietary supplement wherein the fruit pulp is prepared by a method wherein once the pulp is isolated and frozen it is not allowed to pre-thaw prior to dehydration. This method is useful in preparing freeze-dried fruit powders from many fruits, e.g., but not limited to, Açai fruit and Jucara fruit, which can be re-hydrated and retain quality color, texture, and taste.

The granular, freeze-dried fruit powder was stored light protected in a plastic-lined foil bag until use.

Example 33

Challenge Testing of Freeze-Dried Açai Preparation for Stability to Selected Microbes I. Objective The objective of this study was to conduct a preliminary challenge test to assess the microbiological stability of a product when challenged with one strain each of yeast, mold, lactic acid bacteria, *Salmonella*, and *Staphylococcus aureus*. (Silliker Laboratories Research Center, South Holland, Ill.).

II. Applications

This study offers a screening of a product for potential spoilage organisms and two pathogens. It is appropriate to gather initial data about a product and/or to compare a number of product formulations during development.

III. Limitations

With only one strain of each challenge organism, there is a chance that the product will be resistant to growth by that strain but susceptible to other strains. In the challenge organisms grow in the control product, it will be not be determined until the end of the study. This study is limited in time intervals, storage temperatures, and the scope of the report. The study does not predict the results beyond four weeks.

IV. Material and Methods

A. Test Product

A 3.5-kilogram resealable foil bag of product labeled "Açai fruit-freeze dried" was received from the client. Product was stored at ambient temperature until initiation of the study.

B. Challenge Organisms

The product was challenged with freeze-dried strains of *Aspergillus niger* (mold), *Zygosaccharomyces bailli* (yeast); *Lactobacillus fructivorans* (lactic acid bacteria), *Salmonella typhimurium*, and *Staphylococcus aureus* form the Silliker Research Culture Collection (SRCC) as summarized in Table 29. The number of viable cells or spores was verified by plate count methods.

TABLE 29

| Organism | SRCC Number |
| --- | --- |
| *Aspergillus niger* | 1131 |
| *Zygosaccharomyces bailii* | 764 |
| *Lactobacilus fructivorans* | 464 |
| *Salmonella typhimurium* | 449 |
| *Staphylococcus aureus* | 713 |

C. Preparation of Test Samples and Storage

The product was aseptically divided into 6 sterile containers in 100-gram portions. One portion served as a negative control. The other portions were inoculated with one of the cultures at approximately 10,000 colony-forming units per gram. After inoculation, the samples were mixed thoroughly and stored at 75 degrees F.

D. Sample Analyses

The uninoculated control portion was analyzed for challenge organisms on days 0 and 28. Inoculated portions were analyzed on days 0, 7, 14, 21, and 28. A single 11-gram sample was taken from each portion at each interval and analyzed by plate court methods for challenge organisms.

V. Results and Discussion

The microbiological stability of a food product may be determined by challenging it with spoilage and pathogenic microorganisms. When the level of the challenge organisms does not increase during storage, the product formulation is resistant to microbial growth and is considered microbiologically stable.

The results are shown in Table 30 and Table 31. As the data show, the counts of yeast, mold, lactic acid, bacteria, *Salmonella*, and *Staphylococcus aureus* did not increase in the control or inoculated portions of the product during storage. Thus, the Açai fruit-freeze dried product was microbiologically stable for at least 28 days when challenged with yeast, mold, lactic acid bacteria, *Salmonella*, and *Staphylococcus aureus* and stored at 75 degrees F. As shown below, this product was stable against challenge.

TABLE 30

| Açai Fruit - Freeze Dried Non-inoculated Control Samples | | | | | |
| --- | --- | --- | --- | --- | --- |
| Interval | Yeast (cfu/g) | Mold (cfu/g) | Lactic Acid Bacteria (cfu/g) | *Salmonella* (cfu/g) | *Staphylococcus* (cfu/g) |
| Day 0 | 20 | <10 | 20 | <10 | <10 |
| Day 28 | 10 | <10 | 20 | <10 | <10 | cfu/g = colony forming units per gram

TABLE 31

Açai Fruit - Freeze Dried Inoculated Samples

| Interval | Yeast (cfu/g) | Mold (cfu/g) | Lactic Acid Bacteria (cfu/g) | Salmonella (cfu/g) | Staphylococcus (cfu/g) |
|---|---|---|---|---|---|
| Day 0 | 470 | 44,000 | 3,400 | 190 | 44.000 |
| Day 7 | 180 | 50,000 | 2,800 | 80 | 100 |
| Day 14 | 10 | 10,000 | 580 | 170 | 50 |
| Day 21 | 20 | 27,000 | 800 | 30 | <10 |
| Day 28 | 30 | 4,700 | 230 | 10 | <10 | cfu/g = colony forming units per gram

VI. Shelf-Life Studies on Freeze-Dried Açai

Shelf life studies on freeze-dried Açai preparations were conducted by Silliker Laboratories as summarized in below in Table 32.

TABLE 32

Results of shelf-life study

| Month | Aerobic Plate Count (CFU/g) | Yeast (CFU/g) | MOLD (CFU/g) | LACTIC ACID BACTERIA (CFU/g) |
|---|---|---|---|---|
| 0 | — | 20 | <10 | 20 |
| 1 | — | 10 | <10 | 20 |
| 2 | 1,500 | 30 | 40 | 10 |
| 3 | 50 | <10 | <10 | 10 |
| 4 | 750 | <10 | <10 | <10 |
| 5 | 500 | <10 | <10 | 180 |
| 6 | 660 | <10 | <10 | 180 |
| 7 | 1,200 | <10 | <10 | <10 |
| 8 | 360 | <10 | <10 | <10 |
| 9 | <10 | <10 | 10 | <10 |
| 10 | <10 | <10 | 10 | <10 |
| 11 | <10 | <10 | <10 | <10 |
| 12 | <10 | <10 | <10 | <10 |

CFU/g = colony forming units per gram

The taste, odor and appearance of a food (organoleptic qualities) are the ultimate criteria used by consumers to judge a food's acceptability. These qualities begin to change as the microflora in the food-bacteria, yeast, and mold grow and metabolize available nutrients. Organoleptic changes are generally not detectable until the microbial population is high. The number of organisms required to cause spoilage varies with the food item and the type(s) of microorganisms growing in it. Generally, however, the end of shelf life limits during storage. Therefore, the shelf life of the Açai Fruit-Freeze Dried product was at least 12 months stored at 75 degrees F.

Example 34

Acute Oral Toxicity Study of 'Açai Fruit Pulp Freeze Dried' with 14-Day Post-Treatment Observation Period in the Rat (Limit Test)

Studies were conducted to assess the acute oral toxicity of freeze-dried Açai fruit pulp with a 14-day posttreatment observation period in the rat (limit test) ((Study code: PCDL-0221; Pharmaceutical Control and Development Laboratory Co. Ltd., 9. Mexikoi Street Budapest, H-1149).

I. General Information:
A. Dose
Single oral limit dose of 2,000 mg/kg body weight of 'Açai fruit pulp—Freeze dried' (Lot number: 22.10) was applied to rats orally by gavage. Animals were observed for lethality and toxic symptoms for 14 days. Gross pathological examination was carried out on the 15th day. The body weight of the animals corresponded to their species and age throughout the study. No death occurred after oral administration of 'Açai fruit pulp—Freeze dried' at 2,000 mg/kg dose. No toxic clinical symptoms were observed. Scheduled autopsy carried out on day 15 revealed no toxic gross pathological changes. It was concluded that no adverse effects were noted at single oral dose of 2,000 mg/kg 'Açai fruit pulp—Freeze dried' in male and female rats.

B. Objective

To develop data on the potential toxicological effects of single oral administration of Açai fruit pulp—Freeze-dried in the rat. The test article is expected to use as dietary supplement.

C. Type of the Study

Preclinical toxicological study in compliance with the principles of the Good Laboratory Practice Regulations for Nonclinical Laboratory Studies of the United States Food and Drug Administration and the Hungarian Act 1998: XXVIII regulating animal protection. Limit test.

D. Deviations from the Study Protocol i. Characteristics of Substance T 61 Used for Extermination Manufacturer:

Original protocol: Hoechst Veterinar GmbH

Final Report: Intervet International

Reason: The name of the manufacturer has been changed.

ii. Mortality

Original protocol: Observations are made for 4 hours following treatment and twice daily thereafter.

Final Report: Observations were made for 4 hours following treatment and twice daily thereafter at the beginning and at the end of the working day as well as once at weekends, until the morning of the 15th day.

Reason: Procedures have been described more precisely than originally.

iii. General State, External Appearance, Behavior, and Clinical Symptoms

Original protocol: During the post-treatment period, animals are checked daily twice until the morning of the 15th day.

Final Report: During the post-treatment period, animals were checked daily twice until the morning of the 15th day except for weekends when animals were checked once.

Reason: Procedures have been described more precisely than originally

II. Test and Reference Articles
A. Characteristics of the Test Article

The characteristics of the test article are detailed below in Table 33.

TABLE 33

| | |
|---|---|
| Name of the article: | Açai fruit pulp - Freeze dried |
| Botanical name: | *Euterpe oleracea*, Family: Palmae |
| Plant part used: | Fresh Frozen Fruit Pulp |
| Manufacturer: | Greater Continents do Brasil Ltda. Rua Alabastro, 55-112, Aclimação 01531-010 São Paulo, SP Brasil |
| Lot #: | 22.10 |
| Identification number in PCDL: | 2002/22885 |
| Re-hydration: | 1:13 water |
| Residual moisture: | max. 3%, result: 1% |
| Physical characteristics: | dark purple granular freeze dried powder with characteristic odor and flavor, hygroscopic |
| Storage conditions: | refrigerated according to USP (2-8° C., humidity not controlled), re-sealed quickly if opened |

B. Microbiological Analysis

Microbiological limit test according to c. USP was carried out by the Microbiological Department of PCDL.

C. Characteristics of the Article Used for Suspending the Test Article i. Methylcellulose Methylcellulose (Bach No. 127H1066; Expiration February 2003) was commercially obtained from Sigma and stored at room temperature prior to use.

ii. Distilled Water

Distilled water (Batch No. A0010102; Expiration March 2003) was commercially obtained from PCDL and stored at room temperature prior to use.

iii. Characteristics of article used for overanesthesia before necropsy

T 61 (Batch No. 09WO08; Expiration May 2006) containing 0.2 g embutramide, 0.005 g terracing hydrochloride, and 0.05 g mebezonium iodide per ml was commercially obtained from Intervet International and stored at room temperature, in a safe box for poisonous drugs prior to use.

iv. Formulation of the Test Article

The necessary amount of the test article was weighed and suspended in 1% methylcellulose containing solution not earlier than 30 mm before administration. The following suspension was prepared: Nominal dose 2000 mg/kg: 5.0 g Açai fruit pulp ad 50 ml of 1% methylcellulose solution. Suspension was stirred during treatment with a Radelkis magnetic stirrer type OP-951.

V. Concentration Control of the Formulated Test Article

Samples of the formulated test substance were taken for check of the concentration and homogeneity. Concentration and homogeneity check was performed by gravimetry. The concentration of all three samples measured in triplicates of the upper, intermediate, and lower parts of the suspension (homogeneity check) were within the acceptable ±10% limits i.e., upper: +4.4±4.6%, intermediate: +4.0±4.8%, lower: +5.4±2.8%.

III. Test System

A. Animals

Sprague Dawley rat, Crl:CD BR (6-7 weeks of age at arrival) were used in the present studies. The males had body weights that ranged from 143.9 g to 159.4 g. The females had body weights that ranged from 140.5 g to 161.4 g. A pool of animals ordered: 30 (15 males, 15 females). Number of animals involved in the study: 20 (10 males, 10 females) Rats were commercially obtained from Charles River Hungary Ltd. Animals were SPF at arrival and kept in a conventional environment during the study. The rat is commonly used for toxicological studies in accordance with international recommendations. The Sprague Dawley strain is a well-known laboratory model with sufficient historical data.

The animals were identified by ear numbering technique and housed in cages by five of the same sex. The cages were labeled with tags indicating the I.D. numbers of the rats, the study code, the group identification, route of administration, sex and the starting and ending dates of the experimental period.

The animal housing conditions are summarized below in Table 34. The environmental conditions are summarized below in Table 35.

TABLE 34

| Animal housing conditions | |
|---|---|
| Hygienic level: | conventional |
| Type of animal cages: | type II macrolone |

TABLE 34-continued

| Animal housing conditions | |
|---|---|
| Size of cage: H × W × D: | 17.5 cm × 22.5 cm × 37.5 cm |
| Cleaning: | by changing the bottom of the cages three times a week |
| Number of animals per cage: | 5 |
| Number of animal keeping room: | 123 |

TABLE 35

| Environmental conditions | |
|---|---|
| Air exchange: | approximately 15 times/hour |
| Temperature: | 22 ± 3° C. |
| Relative humidity: | 30-70% |
| Lighting: | artificial, 12 hour light-dark cycles. |

The temperature and the relative humidity were continuously recorded. The animals were given free access to standardized rat and mouse diet VRF-1 except for the overnight fasting period prior to treatment, during the treatment, and for the first two hours of posttreatment observation. The composition of the diet was controlled by the Manufacturer Altromin GmbH, D-4937 Lage/Lippe. Lange Str. 42. The diet was identified by the date of manufacturing (30.09.2002), stability: 4 months. Rats had free access to tap water via drinking bottles. Drinking water is checked monthly by the Microbiological Department of PCDL. The animals were observed for 5 days prior to the treatment. Only healthy animals, free from any clinical symptom were used in the study.

Grouping of the animals was made with a random table generated by a computer. The animals were randomly assigned to groups on the basis of their body weight, so that the distribution of the body weights in the individual groups were similar.

IV. Experimental Design

The dose levels and group division are summarized below in Table 36.

TABLE 36

| | | Dose | Number of Animals | | Identification # | |
|---|---|---|---|---|---|---|
| Group # | Treatment | mg/kg | Males | Females | Males | Females |
| 1 | Açai fruit pulp | 2,000 | 10 | — | 851-860 | — |
| 2 | Açai fruit pulp | 2,000 | — | 10 | — | 861-870 |

The rationale for the dose selection is as follows. The expected human daily dose of Açai fruit pulp is approx. 1000 mg per day which corresponds to 14 mg/kg body weight of an adult (70 kg) or 50 mg/kg for a 4 years old child (20 kg). The 2000 mg/kg limit dose applied in this study corresponds to 140 times of the daily dose if consumed by an adult or 40 times of it if 5 g is calculated for a child's body weight.

V. Administration

Application was oral by gavage, The route of application was selected in compliance with international guidelines. The oral route is the anticipated route of human exposure to the test article. The application of the test article was given in a single dose. The test article was administered in a volume of 20 ml/kg body weight. The experimental period consisted of 5 days of acclimatization, treatment's day, 14 days posttreatment observation period including the treatment's day, and the 15th day: necropsy.

VI. Observations, Examinations

A. Lethality

Observations were made for 4 hours following treatment and twice daily thereafter at the beginning and at the end of working days as well as once at weekends until the morning of the 15th day. The time of death should have been recorded as accurately as possible.

B. General State, External Appearance, Behavior, and Clinical Symptoms

Careful clinical observation of the rats was carried out once before the exposure, then, after the treatment for 6 hours continuously. During the subsequent period, animals were checked daily twice until the morning of the 15th day except for weekends, when animals were checked once. Signs to be observed included changes in skin, fur, eyes and visible mucous membranes; occurrence of secretions and excretions and autonomic activity (e.g., lacrimation, piloerection, diarrhea, pupil size, unusual respiratory pattern). Furthermore, potential changes in gait, posture and response to handling as well as the presence of somnolence, trembling, clonic or tonic movements, stereotypes or bizarre behavior were recorded.

C. Body Weight

Animals were weighed at arrival in the laboratory, on the day of randomization, on the day of treatment, as well as on the 2nd, 8th, and 15th day of the experiment prior to the necropsy.

VII. Necropsy and Histological Examination

A. Necropsy

All surviving rats on completion of the posttreatment observation period were exterminated under T61 overanaesthesia and autopsied. External and internal status were carefully observed and recorded. No microscopic examination of organs was performed.

VIII. Evaluation, Statistical Analysis

Groups of males and females were evaluated separately.

A. Parametric Values

Mean values and standard deviations were calculated of the body weights.

B. Non Parametric Values (Lethality and Clinical Symptoms)

The incidence of lethality, clinical symptoms, and gross findings were tabulated.

IX. Procedures

The experiments were performed according to the current Standard Operating Procedures of the Department of Toxicology of the Pharmaceutical Control and Development Laboratory Co. Ltd.

X. Animal Protection

In the interests of animal welfare the unnecessary use of animals was avoided. To order the mild extermination of unambiguously moribund animals was the responsibility of the study director. The present method (limit test) uses a reduced number of experimental animals in comparison to other known and acknowledged acute toxicity tests.

XI. Data Recording and Archivation

All original data are maintained, as dictated by the Standard Operating Procedures, on appropriate follows:
Test Compound weighing
Animal room logbook
Body weight logbooks
Lethality and Clinical observations logbooks
Postmortem records The data obtained in the course of the study were collected in a Study File. The Study Protocol, all data generated during and as a result of the study, the documents and all information in connection with the study, a control sample of the test article and the Final Report will be stored at least for 15 years in the Archives of the PCDL then offered to the Sponsor.

XII. Results

A. Lethality

The lethality observed in the 14-day post-treatment observation period is summarized below in Table 37.

TABLE 37

| Treatment | Death/number of animals | |
| --- | --- | --- |
| | Group 1 MALES | Group 2 FEMALES |
| Açai fruit pulp; 2,000 mg/kg, po. | 0/10 | 0/10 |

Table 38 summarizes the individual lethality data for male test subjects in the acute oral toxicity study of 'Açai fruit pulp—Freeze dried with 14-day post-treatment observation period in the rat (limit test).

TABLE 38

| Group* | Males | | | | | | | | | | | | | | |
| --- | --- | --- | --- | --- | --- | --- | --- | --- | --- | --- | --- | --- | --- | --- | --- |
| | DAYS OF OBSERVATION PERIOD | | | | | | | | | | | | | | |
| Animal code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 851 | 0 | 0 | 0 | 0 | 0 | 0 | 0 | 0 | 0 | 0 | 0 | 0 | 0 | 0 | 0 |
| 852 | 0 | 0 | 0 | 0 | 0 | 0 | 0 | 0 | 0 | 0 | 0 | 0 | 0 | 0 | 0 |
| 853 | 0 | 0 | 0 | 0 | 0 | 0 | 0 | 0 | 0 | 0 | 0 | 0 | 0 | 0 | 0 |
| 854 | 0 | 0 | 0 | 0 | 0 | 0 | 0 | 0 | 0 | 0 | 0 | 0 | 0 | 0 | 0 |
| 855 | 0 | 0 | 0 | 0 | 0 | 0 | 0 | 0 | 0 | 0 | 0 | 0 | 0 | 0 | 0 |
| 856 | 0 | 0 | 0 | 0 | 0 | 0 | 0 | 0 | 0 | 0 | 0 | 0 | 0 | 0 | 0 |
| 857 | 0 | 0 | 0 | 0 | 0 | 0 | 0 | 0 | 0 | 0 | 0 | 0 | 0 | 0 | 0 |
| 858 | 0 | 0 | 0 | 0 | 0 | 0 | 0 | 0 | 0 | 0 | 0 | 0 | 0 | 0 | 0 |
| 859 | 0 | 0 | 0 | 0 | 0 | 0 | 0 | 0 | 0 | 0 | 0 | 0 | 0 | 0 | 0 |
| 860 | 0 | 0 | 0 | 0 | 0 | 0 | 0 | 0 | 0 | 0 | 0 | 0 | 0 | 0 | 0 |

*Açai fruit pulp (2,000 mg/kg, po.); Remarks: 0 = No Lethality;
*Day 1 = Treatment's day Table 39 summarizes the individual lethality data for female test subjects in the acute oral toxicity study of 'Açai fruit pulp—Freeze dried with 14-day post-treatment observation period in the rat (limit test).

TABLE 39

| | Females | | | | | | | | | | | | | | |
|---|---|---|---|---|---|---|---|---|---|---|---|---|---|---|---|
| Group* | DAYS OF OBSERVATION PERIOD | | | | | | | | | | | | | | |
| Animal code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 861 | 0 | 0 | 0 | 0 | 0 | 0 | 0 | 0 | 0 | 0 | 0 | 0 | 0 | 0 | 0 |
| 862 | 0 | 0 | 0 | 0 | 0 | 0 | 0 | 0 | 0 | 0 | 0 | 0 | 0 | 0 | 0 |
| 863 | 0 | 0 | 0 | 0 | 0 | 0 | 0 | 0 | 0 | 0 | 0 | 0 | 0 | 0 | 0 |
| 864 | 0 | 0 | 0 | 0 | 0 | 0 | 0 | 0 | 0 | 0 | 0 | 0 | 0 | 0 | 0 |
| 865 | 0 | 0 | 0 | 0 | 0 | 0 | 0 | 0 | 0 | 0 | 0 | 0 | 0 | 0 | 0 |
| 866 | 0 | 0 | 0 | 0 | 0 | 0 | 0 | 0 | 0 | 0 | 0 | 0 | 0 | 0 | 0 |
| 867 | 0 | 0 | 0 | 0 | 0 | 0 | 0 | 0 | 0 | 0 | 0 | 0 | 0 | 0 | 0 |
| 868 | 0 | 0 | 0 | 0 | 0 | 0 | 0 | 0 | 0 | 0 | 0 | 0 | 0 | 0 | 0 |
| 869 | 0 | 0 | 0 | 0 | 0 | 0 | 0 | 0 | 0 | 0 | 0 | 0 | 0 | 0 | 0 |
| 870 | 0 | 0 | 0 | 0 | 0 | 0 | 0 | 0 | 0 | 0 | 0 | 0 | 0 | 0 | 0 |

*Açai fruit pulp (2,000 mg/kg, po.); Remarks: 0 = No Lethality;
*Day 1 = Treatment's day No death occurred following the single oral administration of 2,000 mg/kg dose of 'Açai fruit pulp—Freeze dried' to rats. All males and females survived until the end of the 14-day observation period.

B. Clinical Symptoms

The clinical symptoms observed in the 14-day post-treatment observation period are summarized below in Table 40.

TABLE 40

| | Symptom/number of animals | |
|---|---|---|
| Treatment | Group 1 MALES | Group 2 FEMALES |
| Açai fruit pulp; 2,000 mg/kg, po. | 0/10 | 0/10 |

Table 41 summarizes the individual clinical symptoms for male test subjects in the acute oral toxicity study of 'Açai fruit pulp—Freeze dried' with 14-day post-treatment observation period in the rat (limit test).

TABLE 41

| | MALES | | | | | | | | | | | | | | |
|---|---|---|---|---|---|---|---|---|---|---|---|---|---|---|---|
| Group* | DAYS OF OBSERVATION PERIOD | | | | | | | | | | | | | | |
| Animal code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 851 | SF | SF | SF | SF | SF | SF | SF | SF | SF | SF | SF | SF | SF | SF | SF |
| 852 | SF | SF | SF | SF | SF | SF | SF | SF | SF | SF | SF | SF | SF | SF | SF |
| 853 | SF | SF | SF | SF | SF | SF | SF | SF | SF | SF | SF | SF | SF | SF | SF |
| 854 | SF | SF | SF | SF | SF | SF | SF | SF | SF | SF | SF | SF | SF | SF | SF |
| 855 | SF | SF | SF | SF | SF | SF | SF | SF | SF | SF | SF | SF | SF | SF | SF |
| 856 | SF | SF | SF | SF | SF | SF | SF | SF | SF | SF | SF | SF | SF | SF | SF |
| 857 | SF | SF | SF | SF | SF | SF | SF | SF | SF | SF | SF | SF | SF | SF | SF |
| 858 | SF | SF | SF | SF | SF | SF | SF | SF | SF | SF | SF | SF | SF | SF | SF |
| 859 | SF | SF | SF | SF | SF | SF | SF | SF | SF | SF | SF | SF | SF | SF | SF |
| 860 | SF | SF | SF | SF | SF | SF | SF | SF | SF | SF | SF | SF | SF | SF | SF |

*Açai fruit pulp (2,000 mg/kg, po.); Remarks: SF = Symptom Free;
*Day 1 = Treatment's day Table 42 summarizes the individual clinical symptoms for female test subjects in the acute oral toxicity study of 'Açai fruit pulp—Freeze dried' with 14-day post-treatment observation period in the rat (limit test).

TABLE 42

| Group* | FEMALES DAYS OF OBSERVATION PERIOD | | | | | | | | | | | | | | |
|---|---|---|---|---|---|---|---|---|---|---|---|---|---|---|---|
| Animal code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 861 | SF | SF | SF | SF | SF | SF | SF | SF | SF | SF | SF | SF | SF | SF | SF |
| 862 | SF | SF | SF | SF | SF | SF | SF | SF | SF | SF | SF | SF | SF | SF | SF |
| 863 | SF | SF | SF | SF | SF | SF | SF | SF | SF | SF | SF | SF | SF | SF | SF |
| 864 | SF | SF | SF | SF | SF | SF | SF | SF | SF | SF | SF | SF | SF | SF | SF |
| 865 | SF | SF | SF | SF | SF | SF | SF | SF | SF | SF | SF | SF | SF | SF | SF |
| 866 | SF | SF | SF | SF | SF | SF | SF | SF | SF | SF | SF | SF | SF | SF | SF |
| 867 | SF | SF | SF | SF | SF | SF | SF | SF | SF | SF | SF | SF | SF | SF | SF |
| 868 | SF | SF | SF | SF | SF | SF | SF | SF | SF | SF | SF | SF | SF | SF | SF |
| 869 | SF | SF | SF | SF | SF | SF | SF | SF | SF | SF | SF | SF | SF | SF | SF |
| 870 | SF | SF | SF | SF | SF | SF | SF | SF | SF | SF | SF | SF | SF | SF | SF |

*Açai fruit pulp (2,000 mg/kg, po.); Remarks: SF = Symptom Free;
*Day 1 = Treatment's day No toxic symptoms were observed on the day of application and during the 14-day posttreatment period at any group of the treated animals.

C. Body Weights

The body weights of male test subjects observed in the 14-day post-treatment observation period are summarized below in Table 43.

TABLE 43

| | MALES Body weights [g] | | | | | |
|---|---|---|---|---|---|---|
| Group 1 Treatment* | Day of arrival | Day of randomization | Day −1** | Day 2 | Day 8 | Day 15 |
| Group size: | 10 | 10 | 10 | 10 | 10 | 10 |
| Mean: | 151.3 | 198.8 | 182.2 | 205.4 | 260.5 | 310.0 |
| ±S.D.: | 5.52 | 6.60 | 6.43 | 7.95 | 16.10 | 14.23 |

*Açai fruit pulp (2,000 mg/kg, po.);
**One day prior to treatment

The body weights of female test subjects observed in the 14-day post-treatment observation period is summarized below in Table 44.

TABLE 44

| | FEMALES Body weights [g] | | | | | |
|---|---|---|---|---|---|---|
| Group 1 Treatment* | Day of arrival | Day of randomization | Day −1** | Day 2 | Day 8 | Day 15 |
| Group size: | 10 | 10 | 10 | 10 | 10 | 10 |
| Mean: | 148.9 | 177.6 | 161.2 | 180.4 | 202.6 | 232.8 |
| ±S.D.: | 7.08 | 6.93 | 5.71 | 4.25 | 15.80 | 7.66 |

*Açai fruit pulp (2,000 mg/kg, po.);
**One day prior to treatment

The body weight changes of male test subjects observed in the 14-day post-treatment observation period is summarized below in Table 45.

TABLE 45

| | MALES | | |
|---|---|---|---|
| Groups | Body weight changes [g] | | |
| Treatment* | Day 1 | Days 2-7 | Days 8-14 |
| Group size: | 10 | 10 | 10 |
| Mean: | 182.2 | 205.4 | 260.5 |
| ±S.D.: | 6.43 | 7.95 | 16.10 |

*Açai fruit pulp (2,000 mg/kg, po.)

The body weight changes of female test subjects observed in the 14-day post-treatment observation period is summarized below in Table 46.

TABLE 46

| | FEMALES | | |
|---|---|---|---|
| Groups | Body weight changes [g] | | |
| Treatment* | Day 1 | Days 2-7 | Days 8-14 |
| Group size: | 10 | 10 | 10 |
| Mean: | 19.2 | 22.2 | 30.2 |
| ±S.D.: | 3.34 | 13.00 | 15.73 |

*Açai fruit pulp (2,000 mg/kg, po.)

The individual body weights of male test subjects observed in the 14-day post-treatment observation period is summarized below in Table 47.

TABLE 47

| | MALES Body weights [g] | | | | | |
|---|---|---|---|---|---|---|
| Group Animal code *Group 1: | Day of arrival | Day of randomization | Day −1** | Day 2 | Day 8 | Day 15 |
| 851 | 159.4 | 207.8 | 187.8. | 214.2 | 287.2 | 314.0 |
| 852 | 154.4 | 205.9 | 191.1 | 214.7 | 264.6 | 313.1 |
| 853 | 154.3 | 204.2 | 186.6 | 212.3 | 269.8 | 319.8 |
| 854 | 153.4 | 201.3 | 187.2 | 211.6 | 268.6 | 330.1 |

TABLE 47-continued

MALES

| Group | Body weights [g] | | | | | |
|---|---|---|---|---|---|---|
| Animal code *Group 1: | Day of arrival | Day of random- ization | Day −1** | Day 2 | Day 8 | Day 15 |
| 855 | 153.7 | 200.8 | 182.7 | 209.2 | 268.2 | 323.2 |
| 856 | 147.4 | 199.1 | 177.5 | 200.0 | 242.2 | 308.7 |
| 857 | 156.4 | 197.8 | 184.3 | 203.6 | 261.4 | 292.5 |
| 858 | 145.6 | 192.1 | 178.1 | 196.1 | 265.2 | 286.4 |
| 859 | 143.9 | 191.4 | 175.8 | 197.4 | 232.2 | 316.4 |
| 860 | 144.1 | 187.8 | 170.7 | 194.4 | 245.2 | 295.3 |
| Group size: | 10 | 10 | 10 | 10 | 10 | 10 |
| Mean: | 151.3 | 198.8 | 182.2 | 205.4 | 260.5 | 310.0 |
| ±S.D.: | 5.52 | 6.60 | 6.43 | 7.95 | 16.10 | 14.23 |

*Group 1: Açai fruit pulp (2,000 mg/kg, po.);
**One day prior to treatment

The individual body weights of female test subjects observed in the 14-day post-treatment observation period is summarized below in Table 48.

TABLE 48

FEMALES

| Group | Body weights [g] | | | | | |
|---|---|---|---|---|---|---|
| Animal code *Group 1: | Day of arrival | Day of random- ization | Day −1** | Day 2 | Day 8 | Day 15 |
| 861 | 141.0 | 190.2 | 170.5 | 183.1 | 228.3 | 237.8 |
| 862 | 142.4 | 184.5 | 168.3 | 187.1 | 231.5 | 236.4 |
| 863 | 143.1 | 181.9 | 165.6 | 182.0 | 210.7 | 225.9 |
| 864 | 149.7 | 179.9 | 164.3 | 184.6 | 203.1 | 237.3 |
| 865 | 156.2 | 177.9 | 160.6 | 182.5 | 193.8 | 235.7 |
| 866 | 149.7 | 177.2 | 156.0 | 177.5 | 189.4 | 227.4 |
| 867 | 154.2 | 174.3 | 158.8 | 174.6 | 191.1 | 222.8 |
| 868 | 161.4 | 171.9 | 156.5 | 180.2 | 191.1 | 235.8 |
| 869 | 140.9 | 171.1 | 158.4 | 178.4 | 193.6 | 222.6 |
| 870 | 140.5 | 166.8 | 153.2 | 174.1 | 193.2 | 245.9 |
| Group size: | 10 | 10 | 10 | 10 | 10 | 10 |
| Mean: | 148.9 | 177.6 | 161.2 | 180.4 | 202.6 | 232.8 |
| ±S.D.: | 7.08 | 6.93 | 4.71 | 4.25 | 15.80 | 7.66 |

*Group 1: Açai fruit pulp (2,000 mg/kg, po.);
**One day prior to treatment

The individual body weight changes of male test subjects observed in the 14-day post-treatment observation period is summarized below in Table 49.

TABLE 49

MALES

| | Body weight changes [g]** | | |
|---|---|---|---|
| Animal code* | Day 1 | Days 2-7 | Days 8-14 |
| 851 | 26.4 | 73.0 | 26.8 |
| 852 | 23.6 | 49.9 | 48.5 |
| 853 | 25.7 | 57.5 | 50.0 |
| 854 | 24.4 | 57.0 | 61.5 |
| 855 | 6.5 | 59.0 | 55.0 |
| 856 | 22.5 | 42.2 | 66.5 |
| 857 | 19.3 | 57.8 | 31.1 |
| 858 | 18.0 | 69.1 | 21.2 |
| 859 | 21.6 | 34.8 | 84.2 |
| 860 | 23.7 | 50.8 | 50.1 |

TABLE 49-continued

MALES

| | Body weight changes [g]** | | |
|---|---|---|---|
| Animal code* | Day 1 | Days 2-7 | Days 8-14 |
| Group size: | 10 | 10 | 10 |
| Mean: | 23.2 | 55.1 | 49.5 |
| ±S.D.: | 2:88 | 11.41 | 19.22 |

*Group 1: Açai fruit pulp (2,000 mg/kg, po.);
**Differences calculated from body weights weighed on Days 1 and 2, Days 2 and 8 as well as Days 8 and 15, respectively.

The individual body weight changes of female test subjects observed in the 14-day post-treatment observation period is summarized below in Table 50.

TABLE 50

FEMALES

| | Body weight changes [g]** | | |
|---|---|---|---|
| Animal code* | Day 1 | Days 2-7 | Days 8-14 |
| 861 | 12.6 | 45.2 | 9.5 |
| 862 | 18.8 | 44.4 | 4.9 |
| 863 | 16.4 | 28.7 | 15.2 |
| 864 | 20.3 | 18.5 | 34.2 |
| 865 | 21.9 | 11.3 | 41.9 |
| 866 | 21.5 | 11.9 | 38.0 |
| 867 | 15.8 | 16.5 | 31.7 |
| 868 | 23.7 | 10.9 | 44.7 |
| 869 | 20.0 | 15.2 | 29.0 |
| 870 | 20.9 | 19.1 | 52.7 |
| Group size: | 10 | 10 | 10 |
| Mean: | 19.2 | 22.2 | 30.2 |
| ±S.D.: | 3.34 | 13.00 | 15.73 |

*Group 1: Açai fruit pulp (2,000 mg/kg, po.);
**(1) Differences calculated from body weights weighed on Days 1 and 2, Days 2 and 8 as well as Days 8 and 15, respectively. (2) The body weight and the body weight gain of the animals corresponded to their species and age throughout the study.

D. Gross Pathology

The gross pathology findings for test animals are summarized in Table 51.

TABLE 51

| | Gross pathology finding/number of animals | | | |
|---|---|---|---|---|
| | Group 1 - MALES | | Group 2 - FEMALES | |
| Treatment | External* | Internal** | External | Internal |
| Açai fruit pulp*** | 0/10 | 0/10 | 0/10 | 0/10 |

*External: Animal of average development. Skin, fur, visible mucous membranes are intact;
**Internal: organs are without pathological changes;
***2,000 mg/kg, po.

The gross pathology findings for male test animals are summarized in Table 52.

TABLE 52

MALES

| Group | Day 15 | |
|---|---|---|
| Animal code* | External | Internal |
| 851 | No Finding** | No Finding |
| 852 | No Finding | No Finding |
| 853 | No Finding | No Finding |
| 854 | No Finding | No Finding |

TABLE 52-continued

| MALES | | |
|---|---|---|
| Group | Day 15 | |
| Animal code* | External | Internal |
| 855 | No Finding | No Finding |
| 856 | No Finding | No Finding |
| 857 | No Finding | No Finding |
| 858 | No Finding | No Finding |
| 859 | No Finding | No Finding |
| 860 | No Finding | No Finding |

*Açai fruit pulp 2,000 mg/kg, po.;
**"No Finding" means: External: Animal of average development. Skin, fur, visible mucous membranes are intact; Internal: organs are without pathological changes.

All animals survived until the scheduled autopsy, on day 15 and all proved to be free of toxic pathological changes.

E. Evaluation

No death occurred after single oral application of 2,000 mg/kg 'Açai fruit pulp—Freeze dried' dose. No toxic clinical symptoms occurred. Scheduled autopsy at day 15 revealed no toxic gross pathological changes. It was concluded that no adverse effects were noted at single oral dose of 2,000 mg/kg 'Açai fruit pulp—Freeze dried' in male and female rats.

Example 35

Acute Oral Toxicity Study of Jucara Fruit Pulp 'Freeze-Dried' with 14-Day Posttreatment Observation Period in the Rat (Limit Test)

Studies were conducted to assess the acute oral toxicity of freeze-dried Jucara fruit pulp with a 14-day posttreatment observation period in the rat (limit test) ((Study code: PCDL-0222; Pharmaceutical Control and Development Laboratory Co. Ltd., 9. Mexikoi Street Budapest, H-1149).

I. General Information:

A. Dosage

Single oral limit dose of 2,000 mg/kg body weight of 'Jucara fruit pulp—Freeze dried' (Lot number: 2208) was applied to rats orally by gavage. Animals were observed for lethality and toxic symptoms for 14 days. Gross pathological examination was carried out on the 15th day. The body weight of the animals corresponded to their species and age throughout the study. No death occurred after oral administration of 'Jucara fruit pulp—Freeze dried' at 2,000 mg/kg dose. No toxic clinical symptoms were observed. Scheduled autopsy carried out on day 15 revealed no toxic gross pathological changes. It was concluded that no adverse effects were noted at single oral dose of 2,000 mg/kg 'Jucara fruit pulp—Freeze dried' in male and female rats.

B. Objective

To develop data on the potential toxicological effects of single oral administration of Jucara fruit pulp—Freeze-dried in the rat. The test article is expected to use as dietary supplement.

C. Type of the Study

Preclinical toxicological study in compliance with the principles of the Good Laboratory Practice Regulations for Nonclinical Laboratory Studies of the United States Food and Drug Administration and the Hungarian Act 1998: XXVIII regulating animal protection. Limit test.

D. Deviations from the Study Protocol i. Characteristics of Substance T 61 Used for Extermination Manufacturer:

Original protocol: Hoechst Veterinar GmbH
Final Report: Internet International
Reason: The name of the manufacturer has been changed.

ii. Mortality

Original protocol: Observations are made for 4 hours following treatment and twice daily thereafter.

Final Report: Observations were made for 4 hours following treatment and twice daily thereafter at the beginning and at the end of the working day as well as once at weekends, until the morning of the 15th day.

Reason: Procedures have been described more precisely than originally iii. General state, external appearance, behavior, and clinical symptoms Original protocol: During the post-treatment period, animals are checked daily twice until the morning of the 15th day.

Final Report: During the post-treatment period, animals were checked daily twice until the morning of the 15th day except for weekends when animals were checked once.

Reason: Procedures have been described more precisely than originally

II. Test and Reference Articles

A. Characteristics of the Test Article

The characteristics of the test article are detailed below in Table 53.

TABLE 53

| | |
|---|---|
| Name of the article: | Jucara fruit pulp - Freeze dried |
| Botanical name: | *Euterpe edulis*, Family: Palmae |
| Plant part used: | Fresh Frozen Fruit Pulp |
| Manufacturer: | Greater Continents do Brasil Ltda. Rua Alabastro, 55-112, Aclimacão 01531-010 São Paulo, SP Brasil |
| Lot #: | 2208 |
| Identification number in PCDL: | 2002/22886 |
| Residual moisture: | max. <2% |
| Physical characteristics: | dark purple granular freeze dried powder with characteristic odor and flavor, hygroscopic |
| Storage conditions: | refrigerated according to USP (2-8° C., humidity not controlled), re-sealed quickly if opened |

B. Microbiological Analysis

Microbiological limit test according to c. USP was carried out by the Microbiological Department of PCDL.

C. Characteristics of the Article Used for Suspending the Test Article i. Methylcellulose Methylcellulose (Bach No. 127H1066; Expiration February 2003) was commercially obtained from Sigma and stored at room temperature prior to use.

ii. Distilled Water

Distilled water (Batch No. A0010102; Expiration March 2003) was commercially obtained from PCDL and stored at room temperature prior to use.

iii. Characteristics of Article Used for Overanesthesia Before Necropsy

T 61 (Batch No. 09WO08; Expiration May 2006) containing 0.2 g embutramide, 0.005 g tetrAçaine hydrochloride, and 0.05 g mebezonium iodide per ml was commercially obtained from Intervet International and stored at room temperature, in a safe box for poisonous drugs prior to use.

iv. Formulation of the Test Article

The necessary amount of the test article was weighed and suspended in 1% methylcellulose containing solution not earlier than 30 min before administration.

The following suspension was prepared: Nominal dose 2000 mg/kg: 5.0 g Jucara fruit pulp ad 50 ml of 1% methylcellulose solution. The suspension was then stirred during treatment with a Radelkis magnetic stirrer type OP-951.

v. Concentration Control of the Formulated Test Article

Samples of the formulated test substance were taken for check of the concentration and homogeneity. Concentration and homogeneity check was performed by gravimetry.

The concentration of all three samples measured in triplicates of the upper, intermediate, and lower parts of the suspension (homogeneity check) were within the acceptable ±10% limits i.e., upper: +9.4±4.2%, intermediate: +9.4±4.6%, lower: +6.6±2.0%.

III. Test System

A. Animals

Sprague Dawley rat, Crl:CD BR (6-7 weeks of age at arrival) were used in the present studies. The males had body weights that ranged from 143.8 g to 151.9 g. The females had body weights that ranged from 144.2 g to 161.6 g. A pool of animals ordered: 30 (15 males, 15 females). Number of animals involved in the study: 20 (10 males, 10 females). Rats were commercially obtained from Charles River Hungary Ltd. Animals were SPF at arrival and kept in a conventional environment during the study. The rat is commonly used for toxicological studies in accordance with international recommendations. The Sprague Dawley strain is a well-known laboratory model with sufficient historical data.

The animals were identified by ear numbering technique and housed in cages by five of the same sex. The cages were labeled with tags indicating the I.D. numbers of the rats, the study code, the group identification, route of administration, sex and the starting and ending dates of the experimental period.

The animal housing conditions are summarized below in Table 54.

TABLE 54

| | |
|---|---|
| Hygienic level: | conventional |
| Type of animal cages: | type II macrolone |
| Size of cage: H × W × D: | 17.5 cm × 22.5 cm × 37.5 cm |
| Cleaning: | by changing the bottom of the cages three times a week |
| Number of animals per cage: | 5 |
| Number of animal keeping room: | 123 |

The environmental conditions are summarized below in Table 55.

TABLE 55

| | |
|---|---|
| Air exchange: | approximately 15 times/hour |
| Temperature: | 22 ± 30° C. |
| Relative humidity: | 30-70% |
| Lighting: | artificial, 12 hour light-dark cycles. |

The temperature and the relative humidity were continuously recorded.

The animals were given free access to standardized rat and mouse diet VRF-1 except for the overnight fasting period prior to treatment, during the treatment and for the two first hours of the posttreatment observation. The composition of the diet was controlled by the Manufacturer Altromin GmbH, D-4937 Lage/Lippe Lange Str. 42. The diet was identified by the date of manufacturing (30 Sep. 2002), stability: 4 months. Rats had free access to tap water via drinking bottles. Drinking water is checked monthly by the Microbiological Department of PCDL. The animals were observed for 5 days prior to the treatment. Only healthy animals, free from any clinical symptom were used in the study.

Grouping of the animals was made with a random table generated by a computer. The animals were randomly assigned to groups on the basis of their body weight, so that the distribution of the body weights in the individual groups were similar.

IV. Experimental Design

The dose levels and group division are summarized below in Table 56,

TABLE 56

| Group | | Dose | Number of Animals | | Identification numbers | |
|---|---|---|---|---|---|---|
| Number | Treatment | mg/kg | Males | Females | Males | Females |
| 1 | Jucara fruit pulp | 2,000 | 10 | — | 871-880 | — |
| 2 | Jucara fruit pulp | 2,000 | — | 10 | — | 881-890 | the rational for the dose selection is as follows. The expected human daily dose of Jucara fruit pulp is approx. 1000 mg per day which corresponds to 14 mg/kg body weight of an adult (70 kg) or 50 mg/kg for a 4 years old child (20 kg). The 2000 mg/kg limit dose applied in this study corresponds to 140 times of the daily dose if consumed by an adult or 40 times of it if 5 g is calculated for a child's body weight.

V. Administration

Application was oral by gavage. The route of application was selected in compliance with international guidelines. The oral route is the anticipated route of human exposure to the test article. The application of the test article was given in a single dose. The test article was administered in a volume of 20 ml/kg body weight. The experimental period consisted of 5 days of acclimatization, treatments day, 14 days post-treatment observation period including the treatment's day, and the 15th day: necropsy.

VI. Observations, Examinations

A. Lethality

Observations were made for 4 hours following treatment and twice daily thereafter at the beginning and at the end of working days as well as once at weekends until the morning of the 15th day. The time of death should have been recorded as accurately as possible.

B. General State, External Appearance, Behavior, and Clinical Symptoms

Careful clinical observation of the rats was carried out once before the exposure, then, after the treatment for 6 hours continuously. During the subsequent period, animals were checked daily twice until the morning of the 15th day except for weekends, when animals were checked once. Signs to be observed included changes in skin, fur, eyes and visible mucous membranes; occurrence of secretions and excretions and autonomic activity (e.g., lacrimation, piloerection, diarrhea, pupil size, unusual respiratory pattern). Furthermore, potential changes in gait, posture and response to handling as well as the presence of somnolence, trembling, clonic or tonic movements, stereotypes or bizarre behavior were recorded.

C. Body Weight

Animals were weighed at arrival in the laboratory, on the day of randomization, on the day of treatment, as well as on the 2nd, 8th, and 15th day of the experiment prior to the necropsy.

VII. Necropsy and Histological Examination

A. Necropsy

All surviving rats on completion of the posttreatment observation period were exterminated under T61 overanaesthesia and autopsied. External and internal status were carefully observed and recorded. No microscopic examination of organs was performed.

VIII. Evaluation, Statistical Analysis

Groups of males and females were evaluated separately.

A. Parametric Values

Mean values and standard deviations were calculated of the body weights.

B. Non Parametric Values (Lethality and Clinical Symptoms)

The incidence of lethality, clinical symptoms, and gross findings were tabulated.

IX. Procedures

The experiments were performed according to the current Standard Operating Procedures of the Department of Toxicology of the Pharmaceutical Control and Development Laboratory Co. Ltd.

X. Animal Protection

In the interests of animal welfare the unnecessary use of animals was avoided. To order the mild extermination of unambiguously moribund animals was the responsibility of the study director. The present method (limit test) uses a reduced number of experimental animals in comparison to other known and acknowledged acute toxicity tests.

XI. Data Recording and Archivation

All original data are maintained, as dictated by the Standard Operating Procedures, on appropriate forms as follows:

Test Compound weighing
Animal room logbook
Body weight logbooks
Lethality and Clinical observations logbooks
Postmortem records The data obtained in the course of the study were collected in a Study File. The Study Protocol, all data generated during and as a result of the study, the documents and all information in connection with the study, a control sample of the test article and the Final Report will be stored at least for 15 years in the Archives of the PCDL then offered to the Sponsor.

XII. Results

A. Lethality

The lethality observed in the 14-day post-treatment observation period is summarized below in Table 57.

TABLE 57

| Treatment | death/number of animals | |
|---|---|---|
| | Group 1 - MALES | Group 2 - FEMALES |
| Juçara fruit pulp; 2,000 mg/kg, po. | 0/10 | 0/10 |

Table 58 summarizes the individual lethality data for male test subjects in the acute

TABLE 58

MALES

| Group/ Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| 871 | 0 | 0 | 0 | 0 | 0 | 0 | 0 | 0 | 0 | 0 | 0 | 0 | 0 | 0 | 0 |
| 872 | 0 | 0 | 0 | 0 | 0 | 0 | 0 | 0 | 0 | 0 | 0 | 0 | 0 | 0 | 0 |
| 873 | 0 | 0 | 0 | 0 | 0 | 0 | 0 | 0 | 0 | 0 | 0 | 0 | 0 | 0 | 0 |
| 874 | 0 | 0 | 0 | 0 | 0 | 0 | 0 | 0 | 0 | 0 | 0 | 0 | 0 | 0 | 0 |
| 875 | 0 | 0 | 0 | 0 | 0 | 0 | 0 | 0 | 0 | 0 | 0 | 0 | 0 | 0 | 0 |
| 876 | 0 | 0 | 0 | 0 | 0 | 0 | 0 | 0 | 0 | 0 | 0 | 0 | 0 | 0 | 0 |
| 877 | 0 | 0 | 0 | 0 | 0 | 0 | 0 | 0 | 0 | 0 | 0 | 0 | 0 | 0 | 0 |
| 878 | 0 | 0 | 0 | 0 | 0 | 0 | 0 | 0 | 0 | 0 | 0 | 0 | 0 | 0 | 0 |
| 879 | 0 | 0 | 0 | 0 | 0 | 0 | 0 | 0 | 0 | 0 | 0 | 0 | 0 | 0 | 0 |
| 880 | 0 | 0 | 0 | 0 | 0 | 0 | 0 | 0 | 0 | 0 | 0 | 0 | 0 | 0 | 0 |

*Açai fruit pulp (2,000 mg/kg, po.); Remark: 0 = No Lethality;
*Day 1 = Treatment's day Table 59 summarizes the individual lethality data for female test subjects in the acute oral toxicity study of 'Jucara fruit pulp—Freeze dried' with 14-day posttreatment observation period in the rat (limit test).

TABLE 59

FEMALES

| Group* Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| 881 | 0 | 0 | 0 | 0 | 0 | 0 | 0 | 0 | 0 | 0 | 0 | 0 | 0 | 0 | 0 |
| 882 | 0 | 0 | 0 | 0 | 0 | 0 | 0 | 0 | 0 | 0 | 0 | 0 | 0 | 0 | 0 |
| 883 | 0 | 0 | 0 | 0 | 0 | 0 | 0 | 0 | 0 | 0 | 0 | 0 | 0 | 0 | 0 |
| 884 | 0 | 0 | 0 | 0 | 0 | 0 | 0 | 0 | 0 | 0 | 0 | 0 | 0 | 0 | 0 |
| 885 | 0 | 0 | 0 | 0 | 0 | 0 | 0 | 0 | 0 | 0 | 0 | 0 | 0 | 0 | 0 |

TABLE 59-continued

| | FEMALES | | | | | | | | | | | | | | |
|---|---|---|---|---|---|---|---|---|---|---|---|---|---|---|---|
| Group* | DAYS OF OBSERVATION PERIOD | | | | | | | | | | | | | | |
| Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 886 | 0 | 0 | 0 | 0 | 0 | 0 | 0 | 0 | 0 | 0 | 0 | 0 | 0 | 0 | 0 |
| 887 | 0 | 0 | 0 | 0 | 0 | 0 | 0 | 0 | 0 | 0 | 0 | 0 | 0 | 0 | 0 |
| 888 | 0 | 0 | 0 | 0 | 0 | 0 | 0 | 0 | 0 | 0 | 0 | 0 | 0 | 0 | 0 |
| 889 | 0 | 0 | 0 | 0 | 0 | 0 | 0 | 0 | 0 | 0 | 0 | 0 | 0 | 0 | 0 |
| 890 | 0 | 0 | 0 | 0 | 0 | 0 | 0 | 0 | 0 | 0 | 0 | 0 | 0 | 0 | 0 |

*Açai fruit pulp (2,000 mg/kg, po.); Remark: 0 = No Lethality;
*Day 1 = Treatment's day No death occurred following the single oral administration of 2,000 mg/kg dose of 'Jucara fruit pulp—Freeze dried' to rats. All males and females survived until the end of the 14-day observation period.

B. Clinical Symptoms

The clinical symptoms observed in the 14-day post-treatment observation period are summarized below in Table 60.

TABLE 60

| | death/number of animals | |
|---|---|---|
| Treatment | Group 1 - MALES | Group 2 - FEMALES |
| Juçara fruit pulp; 2,000 mg/kg, po. | 0/10 | 0/10 |

Table 61 summarizes the individual clinical symptoms for male test subjects in the acute oral toxicity study of 'Jucara fruit pulp—Freeze dried' with 14-day posttreatment observation period in the rat (limit test).

TABLE 61

| | MALES | | | | | | | | | | | | | | |
|---|---|---|---|---|---|---|---|---|---|---|---|---|---|---|---|
| Group* | DAYS OF OBSERVATION PERIOD | | | | | | | | | | | | | | |
| Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 871 | SF | SF | SF | SF | SF | SF | SF | SF | SF | SF | SF | SF | SF | SF | SF |
| 872 | SF | SF | SF | SF | SF | SF | SF | SF | SF | SF | SF | SF | SF | SF | SF |
| 873 | SF | SF | SF | SF | SF | SF | SF | SF | SF | SF | SF | SF | SF | SF | SF |
| 874 | SF | SF | SF | SF | SF | SF | SF | SF | SF | SF | SF | SF | SF | SF | SF |
| 875 | SF | SF | SF | SF | SF | SF | SF | SF | SF | SF | SF | SF | SF | SF | SF |
| 876 | SF | SF | SF | SF | SF | SF | SF | SF | SF | SF | SF | SF | SF | SF | SF |
| 877 | SF | SF | SF | SF | SF | SF | SF | SF | SF | SF | SF | SF | SF | SF | SF |
| 878 | SF | SF | SF | SF | SF | SF | SF | SF | SF | SF | SF | SF | SF | SF | SF |
| 879 | SF | SF | SF | SF | SF | SF | SF | SF | SF | SF | SF | SF | SF | SF | SF |
| 880 | SF | SF | SF | SF | SF | SF | SF | SF | SF | SF | SF | SF | SF | SF | SF |

*Açai fruit pulp (2,000 mg/kg, po.); Remarks: SF = Symptom Free;
*Day 1 = Treatment's day Table 62 summarizes the individual clinical symptoms for female test subjects in the acute oral toxicity study of 'Jucara fruit pulp—Freeze dried' with 14-day posttreatment observation period in the rat (limit test).

TABLE 62

| | FEMALES | | | | | | | | | | | | | | |
|---|---|---|---|---|---|---|---|---|---|---|---|---|---|---|---|
| Group* | DAYS OF OBSERVATION PERIOD | | | | | | | | | | | | | | |
| Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 881 | SF | SF | SF | SF | SF | SF | SF | SF | SF | SF | SF | SF | SF | SF | SF |
| 882 | SF | SF | SF | SF | SF | SF | SF | SF | SF | SF | SF | SF | SF | SF | SF |
| 883 | SF | SF | SF | SF | SF | SF | SF | SF | SF | SF | SF | SF | SF | SF | SF |
| 884 | SF | SF | SF | SF | SF | SF | SF | SF | SF | SF | SF | SF | SF | SF | SF |
| 885 | SF | SF | SF | SF | SF | SF | SF | SF | SF | SF | SF | SF | SF | SF | SF |
| 886 | SF | SF | SF | SF | SF | SF | SF | SF | SF | SF | SF | SF | SF | SF | SF |
| 887 | SF | SF | SF | SF | SF | SF | SF | SF | SF | SF | SF | SF | SF | SF | SF |
| 888 | SF | SF | SF | SF | SF | SF | SF | SF | SF | SF | SF | SF | SF | SF | SF |

TABLE 62-continued

FEMALES

| Group* | | | | | | DAYS OF OBSERVATION PERIOD | | | | | | | | |
|---|---|---|---|---|---|---|---|---|---|---|---|---|---|---|
| Animal Code | Day 1* | Day 2 | Day 3 | Day 4 | Day 5 | Day 6 | Day 7 | Day 8 | Day 9 | Day 10 | Day 11 | Day 12 | Day 13 | Day 14 | Day 15 |
| 889 | SF | SF | SF | SF | SF | SF | SF | SF | SF | SF | SF | SF | SF | SF | SF |
| 890 | SF | SF | SF | SF | SF | SF | SF | SF | SF | SF | SF | SF | SF | SF | SF |

*Açaí fruit pulp (2,000 mg/kg, po.); Remarks: SF = Symptom Free;
*Day 1 = Treatment's day No toxic symptoms were observed on the day of application and during the 14-day posttreatment period at any group of the treated animals.

C. Body Weights

The body weights of male test subjects observed in the 14-day post-treatment observation period is summarized below in Table 63.

TABLE 63

MALES

Body weights [g]

| Group 1 Treatment* | Day of arrival | Day of randomization | Day −1 | Day 2 | Day 8 | Day 15 |
|---|---|---|---|---|---|---|
| Group size: | 10 | 10 | 10 | 10 | 10 | 10 |
| Mean: | 148.1 | 198.6 | 181.8 | 195.6 | 255.5 | 313.8 |
| ±S.D.: | 3.37 | 6.33 | 6.84 | 14.97 | 8.98 | 19.09 |

*Juçara fruit pulp (2,000 mg/kg, p.o.);
**One day prior to treatment

The body weights of female test subjects observed in the 14-day post-treatment observation period is summarized below in Table 64.

TABLE 64

FEMALES

Body weights [g]

| Group 1 Treatment | Day of arrival | Day of randomization | Day −1** | Day 2 | Day 8 | Day 15 |
|---|---|---|---|---|---|---|
| Group size: | 10 | 10 | 10 | 10 | 10 | 10 |
| Mean: | 152.6 | 177.8 | 162.7 | 279.9 | 204.9 | 227.2 |
| ±S.D.: | 6.25 | 7.46 | 7.13 | 9.61 | 5.81 | 19.25 |

Juçara fruit pulp (2,000 mg/kg, p.o.);
**One day prior to treatment

The body weight changes of male test subjects observed in the 14-day post-treatment observation period is summarized below in Table 65.

TABLE 65

MALES

Body weight changes [g]

| Groups* | Day 1 | Day 2 | Day 8 |
|---|---|---|---|
| Group size: | 10 | 10 | 10 |
| Mean: | 13.8 | 60.0 | 58.3 |
| ±S.D.: | 10.76 | 10.28 | 20.36 |

*Juçara fruit pulp; 2,000 mg/kg, po.

The body weight changes of female test subjects observed in the 14-day post-treatment observation period is summarized below in Table 66.

TABLE 66

FEMALES

Body weight changes [g]

| Groups* | Day 1 | Days 2-7 | Days 8-14 |
|---|---|---|---|
| Group size: | 10 | 10 | 10 |
| Mean: | 16.9 | 25.4 | 22.3 |
| ±S.D.: | 4.92 | 5.62 | 14.59 |

*Juçara fruit pulp; 2,000 mg/kg, po.

The individual body weights of mate test subjects observed in the 14-day post-treatment observation period is summarized below in Table 67.

TABLE 67

MALES

Body weights [g]

| Group* Animal code | Day of arrival | Day of randomization | Day −1** | Day 2 | Day 8 | Day 15 |
|---|---|---|---|---|---|---|
| 871 | 146.3 | 208.2 | 191.5 | 213.4 | 265.7 | 328.7 |
| 872 | 151.9 | 205.3 | 185.1 | 208.7 | 255.1 | 314.2 |
| 873 | 147.9 | 202.5 | 188.8 | 209.3 | 265.9 | 310.5 |
| 874 | 143.8 | 202.2 | 178.5 | 204.7 | 263.5 | 323.5 |
| 875 | 148.9 | 200.1 | 180.3 | 207.1 | 261.5 | 332.7 |
| 876 | 145.6 | 198.9 | 178.3 | 181.4 | 258.8 | 284.3 |
| 877 | 153.9 | 196.2 | 188.3 | 194.0 | 248.8 | 322.0 |
| 878 | 146.9 | 192.6 | 183.3 | 186.7 | 242.9 | 334.9 |
| 879 | 144.3 | 190.7 | 171.3 | 174.0 | 250.8 | 279.6 |
| 880 | 151.2 | 189.2 | 172.5 | 176.2 | 242.2 | 307.3 |
| Group size: | 10 | 10 | 10 | 10 | 10 | 10 |
| Mean: | 148.1 | 198.6 | 181.8 | 195.6 | 255.5 | 313.8 |
| ±S.D.: | 3.37 | 6.33 | 6.84 | 14.97 | 8.98 | 19.09 |

*Juçara fruit pulp (2,000 mg/kg, po);
**One day prior to treatment

The individual body weights of female test subjects observed in the 14-day post-treatment observation period is summarized below in Table 68.

TABLE 68

FEMALES

| Group* Animal code | Day of arrival | Day of randomization | Day −1** | Day 2 | Day 8 | Day 15 |
|---|---|---|---|---|---|---|
| 881 | 154.2 | 193.4 | 174.4 | 197.1 | 216.0 | 263.8 |
| 882 | 159.9 | 185.6 | 175.0 | 187.4 | 21L4 | 256.3 |
| 883 | 144.2 | 182.0 | 167.0 | 184.4 | 204.0 | 237.1 |
| 884 | 161.6 | 178.1 | 162.9 | 185.4 | 206.5 | 223.1 |
| 885 | 158.6 | 178.1 | 160.0 | 185.1 | 207.2 | 225.5 |
| 886 | 150.3 | 175.9 | 159.4 | 173.4 | 197.0 | 208.9 |
| 887 | 155.7 | 172.3 | 156.3 | 167.6 | 200.4 | 216.2 |
| 888 | 148.8 | 171.4 | 158.6 | 174.1 | 200.2 | 211.5 |
| 889 | 147.5 | 170.7 | 157.5 | 169.7 | 200.2 | 218.1 |
| 890 | 145.3 | 170.5 | 155.8 | 171.5 | 206.5 | 211.5 |
| Group size: | 10 | 10 | 10 | 10 | 10 | 10 |
| Mean: | 152.6 | 177.8 | 162.7 | 179.6 | 204.9 | 227.2 |
| ±S.D.: | 6.25 | 7.46 | 7.13 | 9.61 | 5.81 | 19.25 |

*Juçara fruit pulp (2,000 mg/kg, po);
**One day prior to treatment

The individual body weight changes of male test subjects observed in the 14-day post-treatment observation period is summarized below in Table 69.

TABLE 69

MALES

| Groups* | Body weight changes [g]** | | |
|---|---|---|---|
| Animal code | Day 1 | Days 2-7 | Days 8-14 |
| 871 | 21.9 | 52.3 | 63.0 |
| 872 | 23.6 | 46.4 | 59.1 |
| 873 | 20.5 | 56.6 | 44.6 |
| 874 | 26.2 | 58.8 | 60.0 |
| 875 | 26.8 | 54.4 | 71.2 |
| 876 | 3.1 | 77.4 | 25.5 |
| 877 | 5.7 | 54.8 | 73.2 |
| 878 | 3.4 | 56.2 | 92.0 |
| 879 | 2.7 | 76.8 | 28.8 |
| 880 | 3.7 | 66.0 | 65.1 |
| Group size: | 10 | 10 | 10 |
| Mean: | 13.8 | 60.0 | 58.3 |
| ±S.D.: | 10.76 | 10.28 | 20.36 |

*Juçara fruit pulp (2,000 mg/kg, p.o.);
**Differences calculated from body weights weighed on Days 1 and 2, Days 2 and 8 as well as Days 8 and 15, respectively.

The individual body weight changes of female test subjects observed in the 14-day post-treatment observation period is summarized below in Table 70.

TABLE 70

FEMALES

| Groups* | Body weight changes [g]** | | |
|---|---|---|---|
| Animal code | Day 1 | Days 2-7 | Days 8-14 |
| 881 | 22.7 | 18.9 | 47.8 |
| 882 | 12.4 | 240 | 44.9 |
| 883 | 17.4 | 19.6 | 33.1 |
| 884 | 22.5 | 21.1 | 16.6 |
| 885 | 25.1 | 22.1 | 18.3 |

TABLE 70-continued

FEMALES

| Groups* | Body weight changes [g]** | | |
|---|---|---|---|
| Animal code | Day 1 | Days 2-7 | Days 8-14 |
| 886 | 14.0 | 23.6 | 11.9 |
| 887 | 11.3 | 32.8 | 15.8 |
| 888 | 15.5 | 26.1 | 11.3 |
| 889 | 12.2 | 30.5 | 17.9 |
| 890 | 15.7 | 35.0 | 5.0 |
| Group size: | 10 | 10 | 10 |
| Mean: | 16.9 | 25.4 | 22.3 |
| ±S.D.: | 4.92 | 5.62 | 14.59 |

*Juçara fruit pulp (2,000 mg/kg, p.o.);
**Differences calculated from body weights weighed on Days 1 and 2, Days 2 and 8 as well as Days 8 and 15, respectively.

The body weight and the body weight gain of the animals corresponded to their species and age throughout the study.

D. Gross Pathology

The gross pathology findings for test animals are summarized in Table 71.

TABLE 71

| | finding/number of animals | | | |
|---|---|---|---|---|
| | Group 1 - MALES | | Group 2 - FEMALES | |
| Treatment | External | Internal | External | Internal |
| Juçara fruit pulp; 2,000 mg/kg, po. | 0/10 | 0/10 | 0/10 | 0/10 |

The gross findings for male test animals is summarized in Table 72.

TABLE 72

MALES

| Groups* | Day 15 | |
|---|---|---|
| Animal code | External | Internal |
| 871 | No Finding** | No Finding |
| 872 | No Finding | No Finding |
| 873 | No Finding | No Finding |
| 874 | No Finding | No Finding |
| 875 | No Finding | No Finding |
| 876 | No Finding | No Finding |
| 877 | No Finding | No Finding |
| 878 | No Finding | No Finding |
| 879 | No Finding | No Finding |
| 880 | No Finding | No Finding |

*Juçara fruit pulp; (2,000 mg/kg, po.);
**"No Finding" here means the following: External: Animal of average development. Skin, fur, visible mucous membranes are intact; Internal: organs are without pathological changes The gross findings for female test animals is summarized in Table 73.

TABLE 73

FEMALES

| Groups* | Day 15 | |
|---|---|---|
| Animal code | External | Internal |
| 881 | No Finding** | No Finding |
| 882 | No Finding | No Finding |
| 883 | No Finding | No Finding |

TABLE 73-continued

FEMALES

| Groups* | Day 15 | |
|---|---|---|
| Animal code | External | Internal |
| 884 | No Finding | No Finding |
| 885 | No Finding | No Finding |
| 886 | No Finding | No Finding |
| 887 | No Finding | No Finding |
| 888 | No Finding | No Finding |
| 889 | No Finding | No Finding |
| 890 | No Finding | No Finding |

*Juçara fruit pulp; (2,000 mg/kg, po.);
**"No Finding" here means the following: External: Animal of average development. Skin, fur, visible mucous membranes are intact; Internal: organs are without pathological changes All animals survived until the scheduled autopsy, on day 15 and all proved to be free of toxic pathological changes.

E. Evaluation

No death occurred after single oral application of 2,000 mg/kg 'Jucara fruit pulp-Freeze dried' dose. No toxic clinical symptoms occurred. Scheduled autopsy at day 15 revealed no toxic gross pathological changes. It was concluded that no adverse effects were noted at single oral dose of 2,000 mg/kg 'Jucara fruit pulp-Freeze dried' in male and female rats.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A composition of *Euterpe oleracea* fruit pulp, the composition consisting essentially of:
   freeze-dried *Euterpe oleracea* fruit pulp having a total anthocyanin concentration greater than 1 milligram per gram total weight and
   an $ORAC_{FL}$ value greater than 350 micromole TE per gram total weight; and
   whereby the *Euterpe oleracea* fruit pulp is initially obtained by hulling *Euterpe oleracea* fruits to isolate *Euterpe oleracea* fruit pulp therefrom.

2. The composition of claim 1, wherein the composition further comprises Jucara fruit.

3. The composition of claim 1, wherein the anthocyanin concentration of the composition is from 1 milligram per gram to 100 milligrams per gram total weight of the composition.

4. The composition of claim 2, wherein the anthocyanin concentration of the composition is from 1 milligram per gram to 100 milligrams per gram total weight of the composition.

5. The composition of claim 1, wherein the composition further comprises a pharmaceutically acceptable carrier.

6. A composition of *Euterpe oleracea* fruit pulp, the composition consisting essentially of:
   freeze-dried *Euterpe oleracea* fruit pulp having a cyclooxygenase inhibition value greater than 15 Aspirin® mg equivalent per gram total weight
   a total anthocyanin concentration greater than 1 milligram per gram total weight and an
   $ORAC_{FL}$ value greater than 350 micromole TE per gram total weight; and
   whereby the *Euterpe oleracea* fruit pulp is initially obtained by hulling the *Euterpe oleracea* fruits to isolate *Euterpe oleracea* fruit pulp therefrom.

7. The composition of claim 6, wherein the composition further comprises Jucara fruit.

8. The composition of claim 6, wherein the anthocyanin concentration of the composition is from 1 milligram per gram to 100 milligrams per gram total weight of the composition.

9. The composition of claim 7, wherein the anthocyanin concentration of the composition is from 1 milligram per gram to 100 milligrams per gram total weight of the composition.

10. The composition of claim 6, wherein the composition further comprises a pharmaceutically acceptable carrier.

* * * * *